(12) United States Patent
Jacobson et al.

(10) Patent No.: US 9,181,253 B2
(45) Date of Patent: *Nov. 10, 2015

(54) ADENOSINE RECEPTOR AGONISTS, PARTIAL AGONISTS, AND ANTAGONISTS

(75) Inventors: Kenneth A. Jacobson, Silver Spring, MD (US); Dilip K. Tosh, Rockville, MD (US)

(73) Assignee: The United States of America, as represented by the Secretary, Department of Health and Human Services, Washington, DC (US)

(*) Notice: Subject to any disclaimer, the term of this patent is extended or adjusted under 35 U.S.C. 154(b) by 457 days.

This patent is subject to a terminal disclaimer.

(21) Appl. No.: 13/479,973

(22) Filed: May 24, 2012

(65) Prior Publication Data
US 2012/0252823 A1    Oct. 4, 2012

Related U.S. Application Data

(63) Continuation-in-part of application No. 13/056,997, filed as application No. PCT/US2009/052439 on Jul. 31, 2009.

(60) Provisional application No. 61/085,588, filed on Aug. 1, 2008.

(51) Int. Cl.
C07D 473/34    (2006.01)
A61K 31/52    (2006.01)

(52) U.S. Cl.
CPC .............. *C07D 473/34* (2013.01); *A61K 31/52* (2013.01)

(58) Field of Classification Search
USPC ....................................... 544/277; 514/263.4
See application file for complete search history.

(56) References Cited

U.S. PATENT DOCUMENTS

| | | | |
|---|---|---|---|
| 5,646,156 | A | 7/1997 | Jacobson et al. |
| 5,688,774 | A | 11/1997 | Jacobson et al. |
| 5,773,423 | A | 6/1998 | Jacobson et al. |
| 5,840,728 | A | 11/1998 | Marquez et al. |
| 6,066,642 | A | 5/2000 | Jacobson et al. |
| 6,187,284 | B1 | 2/2001 | Griffiths |
| 6,197,278 | B1 | 3/2001 | Blankenberg et al. |
| 6,211,165 | B1 | 4/2001 | Liang et al. |
| 6,528,516 | B1 | 3/2003 | Civan et al. |
| 6,586,413 | B2 | 7/2003 | Liang et al. |
| 7,087,589 | B2 | 8/2006 | Jacobson et al. |
| 2003/0143282 | A1 | 7/2003 | Fishman |
| 2003/0216412 | A1 | 11/2003 | Jacobson et al. |
| 2004/0132686 | A1 | 7/2004 | Van Tilburg et al. |
| 2006/0040959 | A1 | 2/2006 | Baraldi et al. |
| 2006/0100168 | A1 | 5/2006 | Ravid et al. |
| 2007/0232626 | A1 | 10/2007 | Jacobson et al. |
| 2011/0046166 | A1 | 2/2011 | Jacobson et al. |
| 2011/0171130 | A1 | 7/2011 | Jacobson et al. |
| 2012/0184569 | A1 | 7/2012 | Jacobson et al. |
| 2012/0252823 | A1 | 10/2012 | Jacobson et al. |
| 2012/0264769 | A1 | 10/2012 | Jacobson et al. |
| 2012/0270829 | A1 | 10/2012 | Salvemini |

FOREIGN PATENT DOCUMENTS

| | | |
|---|---|---|
| EP | 1 798 233 A1 | 6/2007 |
| WO | WO 01/51490 A1 | 7/2001 |
| WO | WO 2006/031505 A1 | 3/2006 |
| WO | WO 2006091905 A1 | 8/2006 |

(Continued)

OTHER PUBLICATIONS

MayoClinic: Type 2 Diabetes. Oct. 22, 2011 <http://www.mayoclinic.org/diseases-conditions/type-2-diabetes/in-depth/diabetes-treatment/art-20051004>.*
Baraldi, Pier. Chem. Rev. 2008, 108, 238-263.*
Fredholm, Bertil. Annu. Rev. Pharmacol. Toxicol. 2005. 45:385-412.*
Jacobson, Kenneth. Nature Reviews Drug Discovery 5, 247-264 (2006).*
MedicineNet. Arrhythmia:Treatment and Heart Disease Symptoms. 2015. <http://www.medicinenet.com/arrhythmia_irregular_heartbeat/article.htm#what_are_the_types_of_arrhythmias>.*
Mayo Clinic. Heart Arrhythmia: treatment and drugs. 2014 < http://www.mayoclinic.org/diseases-conditions/heart-arrhythmia/basics/treatment/con-20027707>.*

(Continued)

*Primary Examiner* — Golam M M Shameem
*Assistant Examiner* — Laura Daniel
(74) *Attorney, Agent, or Firm* — Leydig, Voit & Mayer, Ltd.

(57) ABSTRACT

Disclosed are $A_3$ adenosine receptor antagonists and/or partial agonists and $A_1$ adenosine receptor agonists and/or partial agonists of formula (I):

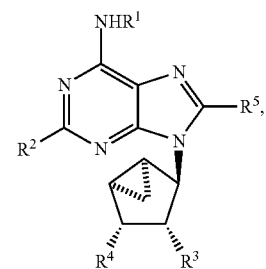

(I)

wherein $R^1$ to $R^5$ are as described herein, as well as pharmaceutical compositions thereof and methods of use thereof. The $A_3$ AR antagonists or partial agonists find use in treating a number of diseases such as cancer, glaucoma, and inflammatory diseases, as well as in preventing cardiac ischemia. Also disclosed are radiolabeled compounds of formula (I) and the use thereof in diagnostic imaging of tissues and organs. The $A_1$ AR agonists and partial agonists find use in treating diseases such as seizures, convulsion, stroke, diabetes, pain, arrhythmias, depression, and anxiety and in cardioprotection or neuroprotection.

12 Claims, 14 Drawing Sheets

(56) References Cited

FOREIGN PATENT DOCUMENTS

| | | |
|---|---|---|
| WO | WO 2006/113204 A2 | 10/2006 |
| WO | WO 2006/125190 A1 | 11/2006 |
| WO | WO 2006/128159 A2 | 11/2006 |
| WO | WO 2007/002139 A2 | 1/2007 |
| WO | WO 2007/009757 A1 | 1/2007 |
| WO | WO 2007/043054 A1 | 4/2007 |
| WO | WO 2007/063538 A1 | 6/2007 |
| WO | WO 2007/086044 A1 | 8/2007 |
| WO | WO 2007/103970 A2 | 9/2007 |
| WO | WO 2007/139775 A2 | 12/2007 |
| WO | WO 2007/139946 A2 | 12/2007 |
| WO | WO 2007/147659 A1 | 12/2007 |
| WO | WO 2008/006369 A1 | 1/2008 |
| WO | WO 2008/023362 A2 | 2/2008 |
| WO | WO 2008/055711 A2 | 5/2008 |
| WO | WO 2008/056361 A1 | 5/2008 |
| WO | WO 2008/058238 A2 | 5/2008 |
| WO | WO 2008/075201 A2 | 6/2008 |

OTHER PUBLICATIONS

Knutsen, Lars. J. Med. Chem. 1999,42:3463-3477.*

Lee, Yen-Mei. Br. J. Pharmacol. 1994, 112: 1031-1036.*

Jain, Nisha. Br. J. Pharmacol. 1995, 116: 2127-2133.*

Elzein et al., "$N^6$-Cycloalkyl-2-substituted adenosine derivaties as selective, high affinity adenosine $A_1$ receptor agonists," *Bioorg. Med. Chem. Lett.* 17, 161-166 (2007).

Tosh et al., "Truncated (N)-Methanocarba Nucleosides as A1 Adenosine Receptor Agonists and Partial Agonists: Overcoming Lack of a Recognition Element,", *ACS Med. Chem. Lett.*, 2, 626-631 (2011) and Supporting Information.

Auchampach et al., "Synthesis and pharmacological characterization of [$^{125}$I]MRS5127, a high affinity, selective agonist radioligand for the $A_3$ adenosine receptor," *Biochem. Pharmacol.*, 79 (7), 967-973 (2010).

Bar-Yehuda et al., "The $A_3$ adenosine receptor agonist CF102 induces apoptosis of hepatocellular carcinoma via de-regulation of the Wnt and NF-κB signal transduction pathways," *Int. J. Oncol.*, 33 (2), 287-295 (2008).

Bradford, "A Rapid and Sensitive Method for the Quantitation of Microgram Quantities of Protein Utilizing the Principle of Protein-Dye Binding," *Anal. Biochem.*, 72, 248-254 (1976).

Cheng et al., "Relationship between the inhibition constant ($K_I$) and the concentration of inhibitor which causes 50 per cent inhibition ($I_{50}$) of an enzymatic reaction," *Biochem. Pharmacol.*, 22, 3099-3108 (1973).

Cordeaux et al., "Agonist-occupied $A_3$ adenosine receptors exist within heterogeneous complexes in membrane microdomains of individual living cells," *FASEB J.*, 22 (3), 850-860 (2008).

Fishman et al., "An agonist to the $A_3$ adenosine receptor inhibits colon carcinoma growth in mice via modulation of GSK-3β and NF-κB," *Oncogene*, 23, 2465-2471 (2004).

Fredholm et al., "International Union of Pharmacology. XXV. Nomenclature and Classification of Adenosine Receptors," *Pharmacol. Rev.*, 53 (4), 527-552 (2001).

Gao et al., "Partial Agonists for $A_3$ Adenosine Receptors," *Curr. Top. Med. Chem.*, 4, 855-862 (2004).

Gao et al., "Structural Determinanats of $A_3$ Adenosine Receptor Activation: Nucleoside Ligands at the Agonist/Antagonist Boundary," *J. Med. Chem.*, 45 (20), 4471-4484 (2002).

Gao et al., "Synthesis and pharmacological characterization of [$^{125}$I]MRS1898, a high-affinity, selective radioligand for the rat $A_3$ adenosine receptor," *Purinergic Signal.*, 5 (1), 31-37 (2009).

Ge et al., "CI-IB-MECA [2-chloro-$N^6$-(3-iodobenzyl)adenosine-5'-N-methylcarboxamide] reduces ischemia/reperfusion injury in mice by activating the $A_3$ adenosine receptor," *J. Pharmacol. Exp. Ther.*, 319 (3), 1200-1210 (2006).

Hofer et al., "Homeostatic Action of Adenosine $A_3$ and $A_1$ Receptor Agonists on proliferation of Hematopoietic Precursor Cells," *Exp. Biol. Med.*, 233 (7), 897-900 (2008).

Jacobson et al., "Semi-rational design of (north)-methanocarba nucleosides as dual acting $A_1$ and $A_3$ adenosine receptor agonists: novel prototypes for cardioprotection," *J. Med. Chem. Letters*, 48 (26), 8103-8107 (2005) (with supporting material).

Joshi et al., "Purine derivatives as ligands for $A_3$ adenosine receptors," *Curr. Top. Med. Chem.*, 5 (13), 1275-1295 (2005).

Joshi et al., "A new synthetic route to (North)-methanocarba nucleosides designed as $A_3$ adenosine receptor agonists," *J. Org. Chem.*, 70 (2), 439-447 (2005).

Kiesewetter et al., "Synthesis and characterization of [$^{76}$Br]-labeled high-affinity $A_3$ adenosine receptor ligands for positron emission tomography," *Nucl. Med. Biol.*, 36 (1), 3-10 (2009).

Kim et al., "2-Substitution of $N^6$-Benzyladenosine-5'-uronarnides Enhances Selectivity for $A_3$ Adenosine Receptors," *J. Med. Chem.*, 37, 3614-3621 (1994).

Kreckler et al., "Adenosine inhibits tumor necrosis factor-α release from mouse peritoneal macrophages via $A_{2A}$ and $A_{2B}$ but not the $A_3$ adenosine receptor," *J. Pharmacol. Exp. Ther.*, 317 (1), 172-180 (2006).

Lasley et al., "The $A_{2a}/A_{2b}$ receptor antagonist ZM-241385 blocks the cardioprotective effect of adenosine agonist pretreatment in in vivo rat myocardium," *Am. J. Physiol. Heart Circ. Physiol.*, 292, H426-H431 (2007).

Lee et al., "Ring-Constrained (N)-Methanocarba Nucleosides as Adenosine Receptor Agonists: Independent 5'-Uronamide and 2'-Deoxy Modifications," *Bioorg. Med. Chem. Lett.*, 11, 1333-1337 (2001).

Liu et al., "Evidence that the adenosine $A_3$ receptor may mediate the protection afforded by preconditioning in the isolated rabbit heart," *Cardiovasc Res.*, 28, 1057-1061 (1994).

Melman et al., "Selective $A_3$ Adenosine Receptor Antagonists Derived from Nucleosides Containing a Bicyclo[3.1.0]hexane Ring System," *Bioorg. Med. Chem.*, 16 (18), 8546-8556 (2008).

Melman et al., "Design of (N)-methanocarba adenosine 5'-uronamides as species—independent $A_3$ receptor-selective agonists," *Bioorg. Med. Chem. Lett.*, 18 (9), 2813-2819 (2008).

Morello et al., "CI-IB-MECA inhibits human thyroid cancer cell proliferation independently of A3 adenosine receptor activation," *Cancer Biol. Ther.*, 7 (2), 278-284 (2008).

Ohta et al., "Role of G-protein-coupled adenosine receptors in downregulation of inflammation and protection from tissue damage," *Nature*, 414, 916-920 (2001).

Pedata et al., "The role of ATP and adenosine in the brain under normoxic and ischemic conditions," *Purinergic Signal.*, 3 (4), 299-310 (2007).

Ramkumar et al., "The $A_3$ Adenosine Receptor Is the Unique Adenosine Receptor Which Facilitates Release of Allergic Mediators in Mast Cells," *J. Biol. Chem.*, 268 (23), 16887-16890 (1993).

Strickler et al., "Direct Preconditioning of Cultured Chick Ventricular Myocytes," *J. Clin. Invest.*, 98, 1773-1779 (1996).

Takahashi et al., "Effects of adenosine on adhesion molecule expression and cytokine production in human PBMC depend on the receptor subtype activated," *Br. J. Pharmacol.*, 150 (6), 816-822 (2007).

Tchilibon et al., "(N)-methanocarba 2,$N^6$-Disubstituted Adenine Nucleosides as Highly Potent and Selective $A_3$ Adenosine Receptor Agonists," *J. Med. Chem.*, 48, 1745-1758 (2005).

Von Lubitz et al., "Adenosine $A_3$ receptor stimulation and cerebral ischemia," *Eur. J. Pharmacol.*, 263, 59-67 (1994).

Wan et al., "The $A_3$ adenosine receptor agonist CP-532,903 [$N^6$-(2,5-dichlorobenzyl)-3'-aminoadenosine-5'-N-methylcarboxamide]protects against myocardial ischemia/reperfusion injury via the sarcolemmal ATP-sensitive potassium channel," *J. Pharmacol. Exp. Ther.*, 324 (1), 234-243 (2008).

Wunderlich et al., "Dual purinergic synaptic transmission in the human enteric nervous system," *Am. J. Physiol. Gastrointest. Liver Physiol.*, 294 (2), G554-G566 (2008).

Zheng et al., "Protective roles of adenosine $A_1$, $A_{2A}$, and $A_3$ receptors in skeletal muscle ischemia and reperfusion injury," *Am. J. Physiol. Heart Circ. Physiol.*, 293 (6), H3685-H3691 (2007).

PCT/US09/38026 International Search Report dated Jul. 8, 2009.

(56) References Cited

OTHER PUBLICATIONS

PCT/US09/52439 International Search Report dated Aug. 3, 2010.
Tosh, "2-Dialkynyl derivatives of (N)-methanocarba nucleosides: Clickable" $A_3$ adenosine receptor-selective agonists,*Bioorganic & Medicinal Chemistry*, 18(2), 508-517 (2010).
Wermuth, "Molecular Variations Based on Isosteric Replacements," The Practice of Medicinal Chemistry, *Academic Press*, 203-237 (1996).
Baraldi et al., "Adenosine Receptor Antagonists: Translating Medicinal Chemistry and Pharmacology into Clinical Utility,": *Chem. Rev.*, 108, 238-263 (2008).

\* cited by examiner

ADENOSINE RECEPTOR AGONISTS, PARTIAL AGONISTS, AND ANTAGONISTS

CROSS-REFERENCE TO RELATED APPLICATIONS

This application is a continuation-in-part of co-pending U.S. patent application Ser. No. 13/056,997, filed Mar. 18, 2011, which is the United States national stage application of International Patent Application No. PCT/US09/052,439, filed Jul. 31, 2009, claiming the benefit of U.S. Provisional Patent Application No. 61/085,588, filed Aug. 1, 2008. The disclosures of the '997, the '439, and the '588 applications are incorporated by reference.

BACKGROUND OF THE INVENTION

There are four subtypes of receptors for adenosine, designated $A_1$, $A_{2A}$, $A_{2B}$, and $A_3$. The $A_3$ adenosine receptor is found primarily in the central nervous system, brain, testes, and the immune system, where it appears to be involved in the modulation of release from mast cells of mediators of the immediate hypersensitivity reaction (Ramkumar et al., *J. Biol. Chem.*, 268, 16887-16890 (1993)).

It is believed that $A_3$ adenosine receptor selective antagonists should serve as cerebroprotective, antiasthmatic, or anti-inflammatory agents. It is also believed that $A_3$ adenosine receptor selective antagonists should serve in the treatment of glaucoma, for example, in reducing intraocular pressure. Research activity is evident in the area of $A_3$ adenosine receptor antagonists; see, for example, U.S. Pat. Nos. 6,066,642 and 6,528,516 and WO 2008/055711. Accordingly, there is a desire to find new $A_3$ adenosine receptor antagonists.

Further, $A_3$ adenosine receptor partial agonists, are advantageous in cardioprotection and produce anti-ischemic effects. Partial agonists also tend to have less side effects than full agonists. In addition, partial agonists are less likely to produce desensitization of the receptor as compared to full agonists. Accordingly, partial agonists can activate the receptor for a longer duration and achieve longer lasting response. Accordingly, there is a desire to find new $A_3$ adenosine receptor partial agonists.

In addition, full or partial agonists of the $A_1$ AR are being considered for treatment of various conditions: seizures, stroke, diabetes, pain, cardioprotection and arrhythmias. $A_1$ AR agonists are highly neuroprotective in ischemic and epileptic models. $A_1$ AR agonists are also being explored for antidepressant, antianxiety, and other neuropsychiatric effects, due to their presynaptic action to decrease the release of excitatory amino acids in the brain. However, peripheral cardiovascular side effects have prevented the introduction of $A_1$ AR agonist for treating disorders of the central nervous system (CNS). Accordingly, there is a desire to find new $A_1$ adenosine receptor full and partial agonists.

BRIEF SUMMARY OF THE INVENTION

The invention provides compounds, pharmaceutical compositions, and methods of use of the compounds. Embodiments of the compounds of the invention are antagonists, or partial agonists, of the $A_3$ adenosine receptor and are purine analogs having substituents at the $N^6$-, 2-, and 9-, and optionally at the 8-position, of the purine core. The compounds have a constrained ring or a rigid bicyclo[3.1.0]hexane ring at the 9-position of the purine core, which provides high potency and selectivity to the $A_3$ adenosine receptor and at the same time lack a substituent on the 4'-position of the bicyclo hexane ring. The absence of a 4'-substituent in many of the compounds leads to lack of activation of the $A_3$ adenosine receptor. Many of the compounds act as $A_3$ adenosine receptor partial agonists.

In addition, the invention provides compounds that are full or partial agonists of the $A_1$ adenosine receptor. The invention also provides pharmaceutical compositions and methods of use of these compounds in treating diseases or conditions in a mammal wherein the diseases or conditions are amenable to treatment by activating, fully or partially, the $A_1$ adenosine receptor of the mammal.

DETAILED DESCRIPTION OF THE INVENTION

Figure 1:
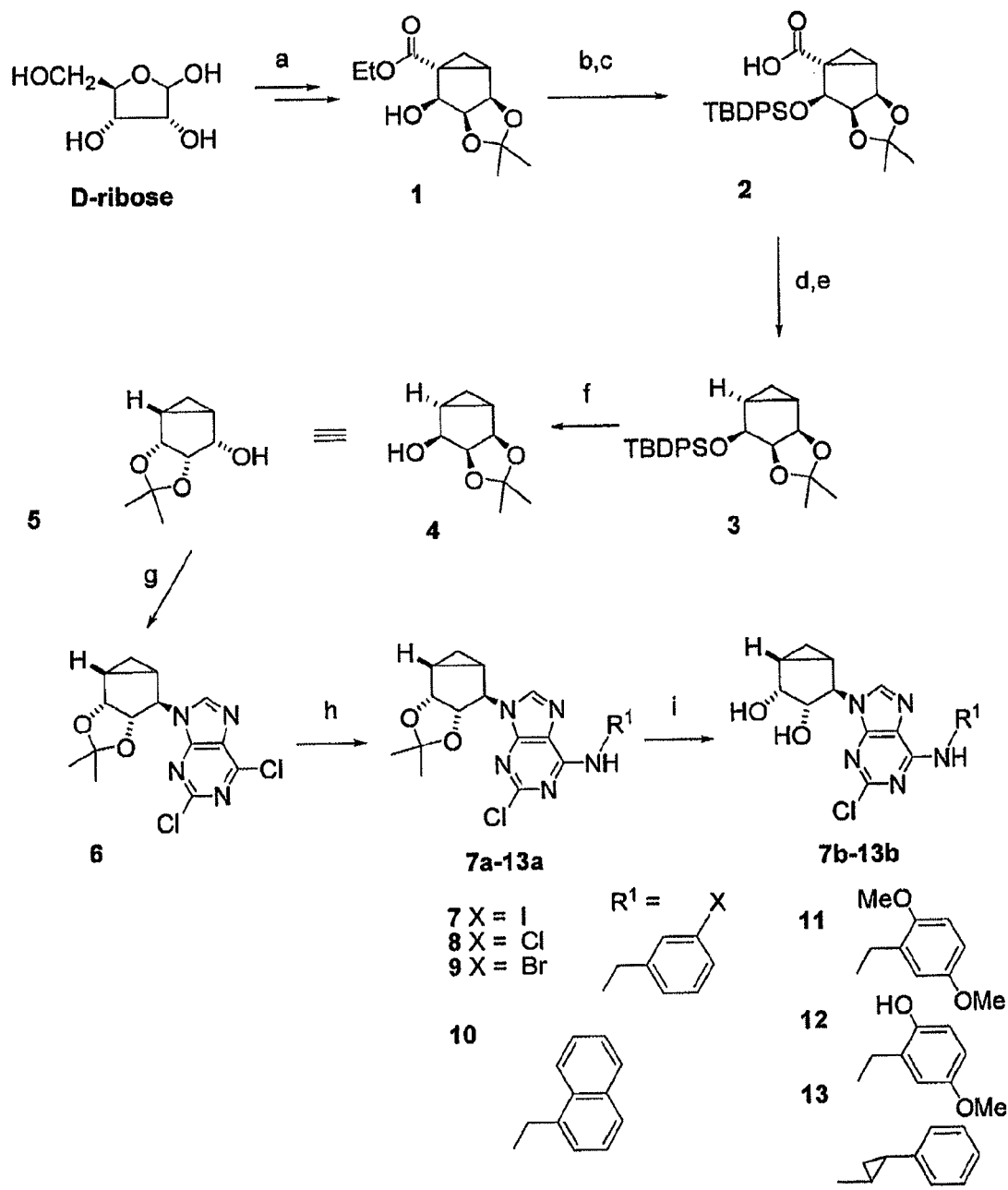
FIG. 1 depicts a reaction scheme to prepare compounds 7b-13b in accordance with an embodiment of the invention. a) 7 steps (see Joshi et al. *Nucleosides, Nucleotides, and Nucleic Acids* 2008, 27, 279 and Joshi et al. *J. Org. Chem.* 2005, 70, 439); b) TBDPS-Cl, imidazole, DMF; c) NaOH, $H_2O$, MeOH, reflux; d) 2-mercaptopyridine N-oxide, DCC, toluene; e) $(Me_3Si)_3SiH$, AIBN, toluene; f) $Bu_4NF$, THF; g) 2,6-dichloropurine, $PPh_3$, DIAD, THF; h) $RNH_2$, EtOH; i) TFA/$H_2O$/MeOH.

The present invention is predicated on the concept that compounds, in accordance with an embodiment, having a ring constrained substituent or a rigid bicyclo[3.1.0]hexane ring at the 9-position which provides high potency as an antagonist and selectivity to the $A_3$ adenosine receptor, or as a partial agonist of the $A_3$ adenosine receptor, and at the same time lack a substituent on the 4'-position of the bicycle hexane ring.

Accordingly, the present invention provides a compound of Formula I:

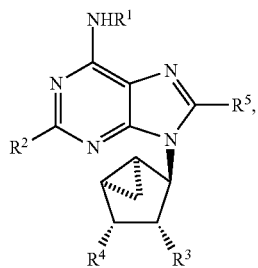

(I)

wherein $R^1$ is selected from the group consisting of hydrogen, $C_1$-$C_6$ alkyl, $C_1$-$C_6$ alkoxy, hydroxyl, $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkoxy, $C_1$-$C_6$ alkyl carbonyl, sulfonyl, $C_1$-$C_6$ alkyl sulfonyl, $C_6$-$C_{14}$ aryl sulfonyl, heterocyclyl $C_1$-$C_6$ alkyl, heterocyclyl, heteroaryl $C_1$-$C_6$ alkyl, 4-[[[4-[[[(2-amino $C_1$-$C_6$ alkyl)amino]-carbonyl]-$C_1$-$C_6$ alkyl]aniline]carbonyl]$C_1$-$C_6$ alkyl]$C_6$-$C_{14}$ aryl, and $C_6$-$C_{14}$ aryl $C_3$-$C_8$ cycloalkyl, wherein the aryl or heterocyclyl portion of $R^1$ is optionally substituted with one or more substituents selected from the group consisting of halo, amino, hydroxyl, carboxy, $C_1$-$C_6$ alkoxycarbonyl, aminocarbonyl, $C_1$-$C_6$ alkylaminocarbonyl, $C_1$-$C_6$ dialkyl aminocarbonyl, $C_1$-$C_6$ alkyl, $C_2$-$C_6$ alkenyl, $C_2$-$C_6$ alkynyl, $C_1$-$C_6$ alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, carboxy $C_1$-$C_6$ alkyl, carboxy $C_2$-$C_6$ alkenyl, carboxy $C_2$-$C_6$ alkynyl, aminocarbonyl $C_1$-$C_6$ alkyl, aminocarbonyl $C_2$-$C_6$ alkenyl, aminocarbonyl $C_2$-$C_6$ alkynyl, and $C\equiv C-(CH_2)_n-COR^7$ wherein $R^7$ is selected from the group consisting of OH, $OR^8$, and $NR^9R^{10}$, wherein $R^8$ is selected from the group consisting of $C_1$-$C_6$ alkyl, $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ and diaryl $C_1$-$C_6$ alkyl; and $R^9$ and $R^{10}$ are independently selected from the group consisting of hydrogen, $C_1$-$C_6$ alkyl, and $(CH_2)_nR^{11}$ wherein $R^{11}$ is $NR^{12}R^{13}$, wherein $R^{12}$ and $R^{13}$ are independently selected from the group consisting of hydrogen, $C_1$-$C_6$ alkyl, and $COR^{14}$ wherein $R^{14}$ is hydrogen or $C_1$-$C_6$ alkyl; wherein n is an integer from 1 to 10; and the alkyl or cycloalkyl portion of $R^1$ is optionally substituted with one or more substituents selected from the group consisting of halo, amino, $C_1$-$C_6$ alkyl, $C_1$-$C_6$ alkoxy, $C_6$-$C_{14}$ aryloxy, $C_1$-$C_6$ hydroxyalkyl, $C_2$-$C_6$ hydroxyalkenyl, $C_2$-$C_6$ hydroxy alkynyl, aminocarbonyl $C_1$-$C_6$ alkoxy, and $C_6$-$C_{14}$ aryl $C_1$-$C_6$ alkoxy;

$R^2$ is selected from the group consisting of hydrogen, halo, amino, hydrazido, mercapto, $C_1$-$C_{20}$ alkylamino, $C_6$-$C_{14}$ aryl amino, $C_6$-$C_{14}$ aryloxy, $C_1$-$C_{20}$ alkyl, $C_1$-$C_{20}$ alkoxy, $C_1$-$C_{20}$ thioalkoxy, pyridylthio, $C_7$-$C_{12}$ cycloalkyl $C_1$-$C_{20}$ alkyl, $C_7$-$C_{12}$ bicycloalkyl $C_1$-$C_{20}$ alkyl, $C_7$-$C_{12}$ bicycloalkenyl $C_1$-$C_{20}$ alkyl, $C_6$-$C_{14}$ aryl $C_1$-$C_{20}$ alkyl, $C_2$-$C_{20}$ alkenyl, $C_7$-$C_{12}$ cycloalkyl $C_2$-$C_{20}$ alkenyl, $C_7$-$C_{12}$ bicycloalkyl $C_2$-$C_{20}$ alkenyl, $C_7$-$C_{12}$ bicycloalkenyl $C_2$-$C_{20}$ alkenyl, $C_6$-$C_{14}$ aryl $C_2$-$C_{20}$ alkenyl, $C_2$-$C_{20}$ alkynyl, $-C\equiv C-(CH_2)_m-C(=O)-O-C_1$-$C_6$ alkyl, $-C\equiv C-(CH_2)_m-C(=O)-NH-(CH_2)_n-NH_2$, $-C\equiv C-(CH_2)_m-C_1$-$C_6$ alkyl, $-C\equiv C-(CH_2)_m$-aryl, wherein m and n are independently 1 to 10, $C_7$-$C_{12}$ cycloalkyl $C_2$-$C_{20}$ alkynyl, $C_7$-$C_{12}$ bicycloalkyl $C_2$-$C_{20}$ alkynyl, $C_7$-$C_{12}$ bicycloalkenyl $C_2$-$C_{20}$ alkynyl, $C_6$-$C_{14}$ aryl $C_2$-$C_{20}$ alkynyl, and the alkyl, cycloalkyl, or aryl portion of $R^2$ is optionally substituted with one or more substituents selected from the group consisting of halo, hydroxyl, amino, alkylamino, dialkylamino, sulfur, carboxy, alkoxycarbonyl, aminocarbonyl, alkylaminocarbonyl, dialkyl aminocarbonyl, aminoalkyl aminocarbonyl, and trialkylsilyl;

$R^3$ and $R^4$ are independently selected from the group consisting of hydroxyl, amino, thiol, ureido, $C_1$-$C_6$ alkyl carbonylamino, hydroxy $C_1$-$C_6$ alkyl, and hydrazinyl; and $R^5$ is selected from the group consisting of hydrogen, $C_1$-$C_6$ alkyl, $C_2$-$C_6$ alkenyl, $C_2$-$C_6$ alkynyl, heteroaryl, and $C_1$-$C_6$ aminoalkyl;

or a pharmaceutically acceptable salt thereof.

In embodiments described above, and in embodiments described below, the following definitions apply.

The term "aryl" refers to aromatic moieties such as phenyl, naphthyl, anthracenyl, and biphenyl. The term "heterocyclyl" refers to 3-7 membered rings which can be saturated or unsaturated or heteroaromatic, comprising carbon and one or more heteroatoms such as O, N, and S, and optionally hydrogen; optionally in combination with one or more aromatic rings. Examples of heterocyclyl groups include pyridyl, piperidinyl, piperazinyl, pyrazinyl, pyrrolyl, pyranyl, tetrahydropyranyl, tetrahydrothiopyranyl, pyrrolidinyl, furanyl, tetrahydrofuranyl, thienyl, furyl, thiophenyl, tetrahydrothiophenyl, purinyl, pyrimidinyl, thiazolyl, thiazolidinyl, thiazolinyl, oxazolyl, pyrazolyl, tetrazolyl, tetrazinyl, benzoxazolyl, morpholinyl, thiomorpholinyl, quinolinyl, and isoquinolinyl. Examples of heteroaryl alkyl include heteroaryl methyl such as 2- or 3-methyl substituted groups, e.g., thienylmethyl, pyridylmethyl, and furylmethyl.

The alkyl, alkoxy, and alkylamino groups can be linear or branched. When an aryl group is substituted with a substituent, e.g., halo, amino, alkyl, hydroxyl, alkoxy, and others, the aromatic ring hydrogen is replaced with the substituent and this can take place in any of the available hydrogens, e.g., 2, 3, 4, 5, and/or 6-position wherein the 1-position is the point of attachment of the aryl group in the compound of the present invention.

The term "halo" refers to fluorine, chlorine, bromine, and iodine.

Examples of bicycloalkyls include norbornyl, s-endonorbornyl, carbamethylcylopentyl, and bicyclohexyl. An example of a tricycloalkyl is adamantyl.

The phrase "salt" or "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media such as ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p. 1445, and *Journal of Pharmaceutical Science,* 66, 2-19 (1977). For example, they can be a salt of an alkali metal (e.g., sodium or potassium), alkaline earth metal (e.g., calcium), or ammonium of salt.

Examples of pharmaceutically acceptable salts for use in the present inventive pharmaceutical composition include those derived from mineral acids, such as hydrochloric, hydrobromic, phosphoric, metaphosphoric, nitric and sulphuric acids, and organic acids, such as tartaric, acetic, citric, malic, lactic, fumaric, benzoic, glycolic, gluconic, succinic, maleic and arylsulfonic, for example, benzenesulfonic and p-toluenesulfonic, acids.

In accordance with an embodiment of the invention, $R^1$ is selected from the group consisting of $C_6$-$C_{14}$ aryl $C_1$-$C_6$ alkyl and $C_6$-$C_{14}$ aryl $C_3$-$C_8$ cycloalkyl, wherein the aryl portion of $R^1$ is optionally substituted with one or more substituents selected from the group consisting of halo, amino, $C_1$-$C_6$ alkyl, $C_1$-$C_6$ alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, aminocarbonyl $C_1$-$C_6$ alkoxy, and $C_6$-$C_{14}$ aryl $C_1$-$C_6$ alkoxy; and in a particular embodiment, $R^1$ is selected from the group consisting of benzyl, phenyl cyclopropyl, or 1-naphthyl methyl, wherein the phenyl or naphthyl portion of $R^1$ is optionally substituted with one or more substituents selected from the group consisting of halo, amino, hydroxyl, carboxy, alkoxycarbonyl, aminocarbonyl, alkylaminocarbonyl, dialkyl aminocarbonyl, $C_1$-$C_6$ alkyl, $C_1$-$C_6$ alkoxy, phenoxy, hydroxy $C_1$-$C_6$ alkyl, hydroxy $C_2$-$C_6$ alkenyl, and hydroxy $C_2$-$C_6$ alkynyl.

In a specific embodiment of the invention, $R^1$ is benzyl, phenyl cyclopropyl, or 1-naphthyl methyl, wherein the phenyl or naphthyl portion of $R^1$ is optionally substituted with one or more substituents selected from the group consisting of halo, hydroxyl, and alkoxy. Examples of $R^1$ are benzyl and benzyl substituted with one or more substituents selected from the group consisting of halo and $C_1$-$C_6$ alkoxy.

In any of the embodiments above, $R^1$ is selected from the group consisting of 3-chlorobenzyl, 3-bromobenzyl, 3-iodobenzyl, 2-hydroxy-5-methoxy-benzyl, and 2,5-dimethoxybenzyl. In an embodiment, the phenyl cyclopropyl is trans-2-phenyl-1-cyclopropyl.

In any of the embodiments above, $R^2$ is halo, specifically chloro, bromo, or iodo, or $R^2$ is —C≡C—$(CH_2)_m$—$CH_3$, —C≡C—$(CH_2)_m$-aryl, —$(CH_2)$, —C≡C—C(=O)—O—$CH_3$, —C≡C—$(CH_2)_m$—C(=O)—NH—$(CH_2)_n$—$NH_2$, wherein m and n are independently 1 to 10, where in certain embodiments m and n are 2 to 6, and in certain other embodiments m and n are 3 to 5, and wherein the $CH_3$ or aryl group is optionally substituted with one or more substituents selected from the group consisting of halo, hydroxyl, amino, alkylamino, dialkylamino, sulfur, carboxy, alkoxycarbonyl, aminocarbonyl, alkylaminocarbonyl, dialkyl aminocarbonyl, aminoalkyl aminocarbonyl, and trialkylsilyl; or a pharmaceutically acceptable salt thereof.

In any of the embodiments above, $R^3$ and $R^4$ are particularly hydroxyl.

In any of the embodiments above, $R^5$ is particularly hydrogen.

The term "one or more substituents" in any of the embodiments of the invention refers to 1, 2, 3, 4, or more substituents.

Particular examples of compounds of the invention are those wherein $R^2$ is chloro, $R^1$ is 3-chlorobenzyl, 3-iodobenzyl, 3-bromobenzyl, 1-naphthylmethyl, 2,5-dimethoxybenzyl, 2-hydroxy-5-methoxybenzyl, or trans-2-phenyl-cyclopropyl, $R^3$ and $R^4$ are hydroxyl, and $R^5$ is hydrogen.

Many of the compounds described above have antagonistic as well as partial agonistic properties at the $A_3$ adenosine receptor, depending upon the parameter studied. The definition of antagonist or agonist is highly dependent upon the cell system and the parameter studied, receptor density, species, and the like.

Figure 2:
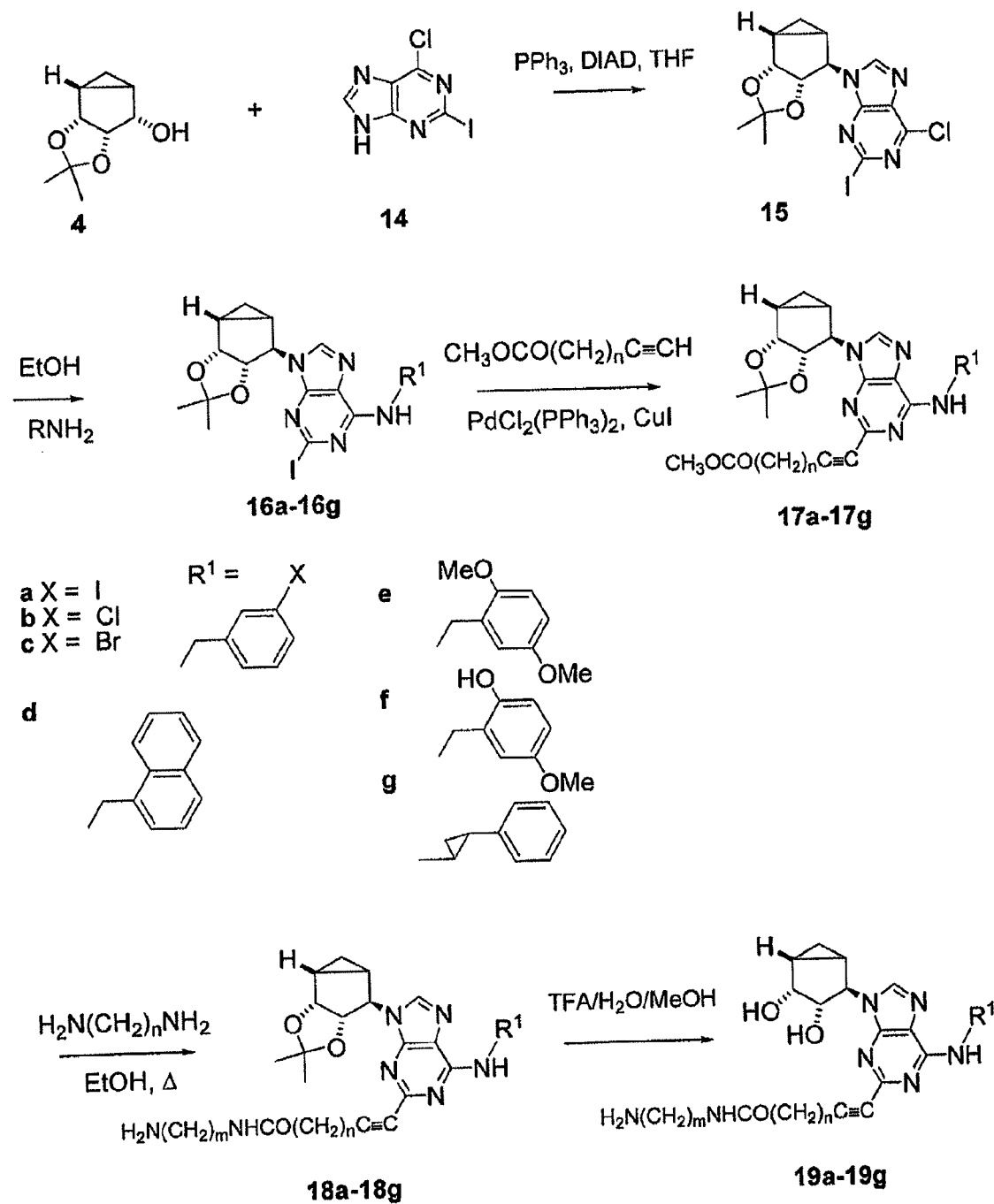
FIG. 2 depicts a reaction scheme to prepare compounds 19a-19g in accordance with an embodiment of the invention.
Figure 3:
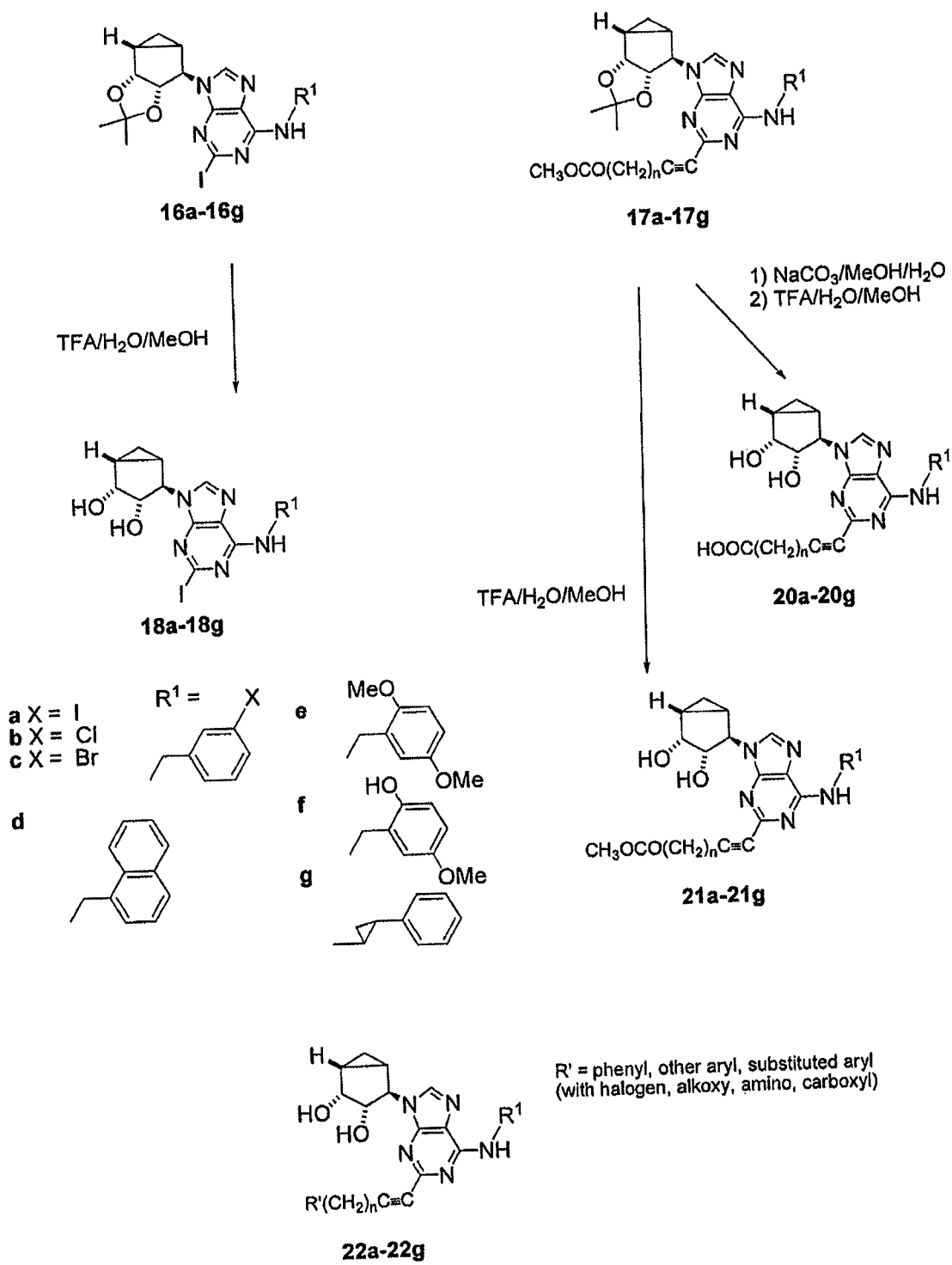
FIG. 3 depicts compounds 22a-22g in accordance with an embodiment of the invention and reaction schemes to prepare compounds 20a-20g and 21a-21g.
Figure 4:
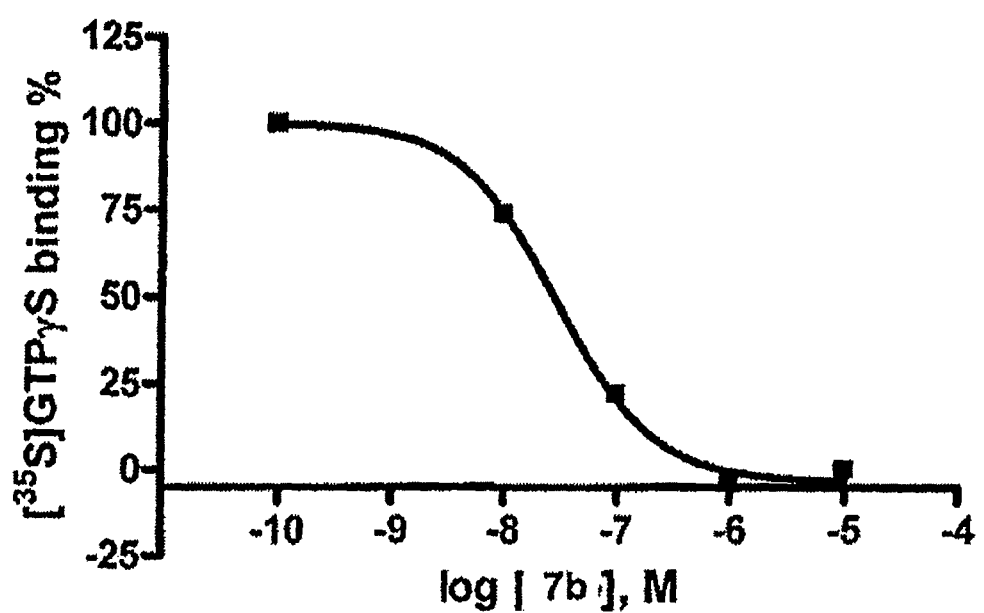
FIG. 4 depicts functional antagonism by the compound 7b of the invention in the guanine nucleotide binding assay ($[^{35}S]GTP\gamma S$) in membranes of CHO cells expressing human $A_3AR$.
Figure 5:
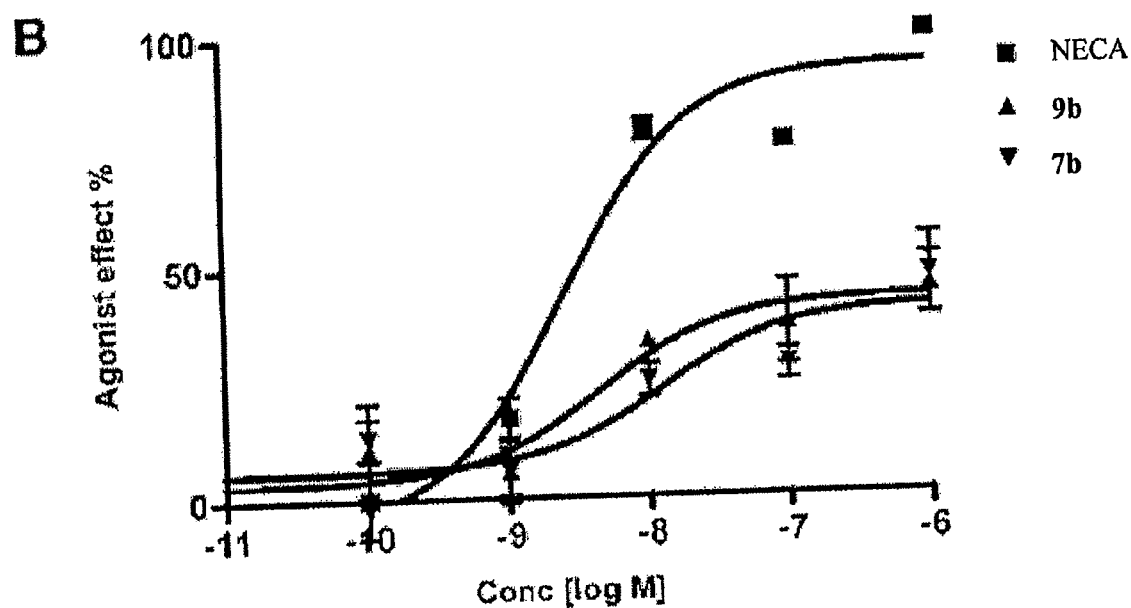
FIG. 5 depicts functional agonism of compounds 7b and 9b in accordance with an embodiment of the invention in an assay of adenylate cyclase membranes of CHO cells expressing $hA_3AR$. The full agonist NECA (5'-N-ethylcarboxamidoadenosine), representing 100% efficiency, is shown comparison.

The compounds of the invention can be prepared by any suitable method. For example, FIG. 1 illustrates a method of preparing compounds 7b-13b. FIG. 2 illustrates a method of preparing compounds 19a-19g. FIG. 3 illustrates a method of preparing compounds 20a-20g and 21a-21g.

In accordance with another embodiment, the invention provides compounds that are agonists or partial agonists of the $A_1$ adenosine receptor. Thus, the invention provides a compound of formula (I):

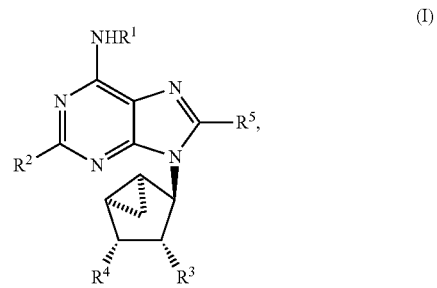

wherein $R^1$ is selected from the group consisting of hydrogen, $C_1$-$C_6$ alkyl, $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, —CH($R^a$)($R^b$), $C_6$-$C_{14}$ aryl, $C_6$-$C_{14}$ aryl $C_1$-$C_6$ alkyl, $C_6$-$C_{14}$ diaryl $C_1$-$C_6$ alkyl, and $C_6$-$C_{14}$ aryl $C_1$-$C_6$ alkoxy, wherein $R^a$ and $R^b$ are independently selected from the group consisting of $C_1$-$C_6$ alkyl, $C_3$-$C_8$ cycloalkyl, and $C_6$-$C_{14}$ aryl, wherein the aryl portion of $R^1$ is optionally substituted with one or more substituents selected from the group consisting of halo, amino, hydroxyl, carboxy, $C_1$-$C_6$ alkoxycarbonyl, aminocarbonyl, $C_1$-$C_6$ alkylaminocarbonyl, $C_1$-$C_6$ dialkyl aminocarbonyl, $C_1$-$C_6$ alkyl, $C_2$-$C_6$ alkenyl, $C_2$-$C_6$ alkynyl, $C_1$-$C_6$ alkoxy, halo $C_1$-$C_6$ alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, carboxy $C_1$-$C_6$ alkyl, carboxy $C_2$-$C_6$ alkenyl, carboxy $C_2$-$C_6$ alkynyl, aminocarbonyl $C_1$-$C_6$ alkyl, aminocarbonyl $C_2$-$C_6$ alkenyl, aminocarbonyl $C_2$-$C_6$ alkynyl, and C≡C—$(CH_2)_n$—$COR^7$ wherein $R^7$ is selected from the group consisting of OH, $OR^8$, and $NR^9R^{10}$, wherein $R^8$ is selected from the group consisting of $C_1$-$C_6$ alkyl, $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ and diaryl $C_1$-$C_6$ alkyl; and $R^9$ and $R^{10}$ are independently selected from the group consisting of hydrogen, $C_1$-$C_6$ alkyl, and $(CH_2)_n R^{11}$ wherein $R^{11}$ is $NR^{12}R^{13}$, wherein $R^{12}$ and $R^{13}$ are independently selected from the group consisting of hydrogen, $C_1$-$C_6$ alkyl, and $COR^{14}$ wherein $R^{14}$ is hydrogen or $C_1$-$C_6$ alkyl; wherein n is an integer from 1 to 10; and the alkyl or cycloalkyl portion of $R^1$ is optionally substituted with one or more substituents selected from the group consisting of halo, amino, $C_1$-$C_6$ alkyl, $C_1$-$C_6$ alkoxy, $C_6$-$C_{14}$ aryloxy, $C_1$-$C_6$ hydroxyalkyl, $C_2$-$C_6$ hydroxyalkenyl, $C_2$-$C_6$ hydroxy alkynyl, aminocarbonyl $C_1$-$C_6$ alkoxy, and $C_6$-$C_{14}$ aryl $C_1$-$C_6$ alkoxy;

$R^2$ is selected from the group consisting of hydrogen, halo, amino, hydrazido, mercapto, $C_1$-$C_{20}$ alkylamino, $C_6$-$C_{14}$ aryl amino, $C_6$-$C_{14}$ aryloxy, $C_1$-$C_{20}$ alkyl, $C_1$-$C_{20}$ alkoxy, $C_1$-$C_{20}$ thioalkoxy, pyridylthio, heterocyclyl, $C_7$-$C_{12}$ cycloalkyl $C_1$-$C_{20}$ alkyl, $C_7$-$C_{12}$ bicycloalkyl $C_1$-$C_{20}$ alkyl, $C_7$-$C_{12}$ bicycloalkenyl $C_1$-$C_{20}$ alkyl, $C_6$-$C_{14}$ aryl $C_1$-$C_{20}$ alkyl, $C_2$-$C_{20}$ alkenyl, $C_7$-$C_{12}$ cycloalkyl $C_2$-$C_{20}$ alkenyl, $C_7$-$C_{12}$ bicycloalkyl $C_2$-$C_{20}$ alkenyl, $C_7$-$C_{12}$ bicycloalkenyl $C_2$-$C_{20}$ alkenyl, $C_6$-$C_{14}$ aryl $C_2$-$C_{20}$ alkenyl, $C_2$-$C_{20}$ alkynyl, carboxy alkyl $C_2$-$C_{20}$ alkynyl, —C≡C—$(CH_2)_m$—C(=O)—O—$C_1$-$C_6$ alkyl, —C≡C—$(CH_2)_m$—C(=O)—NH—$(CH_2)$, —$NH_2$, —C≡C—$(CH_2)_m$—$C_1$-$C_6$ alkyl, —C≡C—$(CH_2)_m$-aryl, wherein m and n are independently 1 to 10, $C_7$-$C_{12}$ cycloalkyl $C_2$-$C_{20}$ alkynyl, $C_7$-$C_{12}$ bicycloalkyl $C_2$-$C_{20}$ alkynyl, $C_7$-$C_{12}$ bicycloalkenyl $C_2$-$C_{20}$ alkynyl, $C_6$-$C_{14}$ aryl $C_2$-$C_{20}$ alkynyl, and the alkyl, cycloalkyl, heterocyclyl, or aryl portion of $R^2$ is optionally substituted with one or more substituents selected from the group consisting of halo, hydroxyl, amino, alkylamino, dialkylamino, sulfur, carboxy, alkoxycarbonyl, aminocarbonyl, alkylaminocarbonyl, dialkyl aminocarbonyl, aminoalkyl aminocarbonyl, pyridyl, alkyl pyridyl, haloalkyl pyridyl, trihaloalkyl pyridyl, carboxy pyridyl, pyrazinyl, quinolinyl, quinazolinyl, and trialkylsilyl, or wherein the heterocyclyl is optionally substituted with an optionally substituted alkyl, optionally substituted aryl, optionally substituted heteroaryl, carboxyl, sulfonyl, —C(O)OR$^e$, —CH(OH)R$^e$, or C(O)NR$^e$R$^f$, wherein R$^e$ or R$^f$ is hydrogen, optionally substituted alkyl, optionally substituted cycloalkyl, optionally substituted aralkyl, optionally substituted aryl, or optionally substituted heteroaryl;

$R^3$ and $R^4$ are independently selected from the group consisting of hydroxyl, amino, thiol, ureido, $C_1$-$C_6$ alkyl carbonylamino, hydroxy $C_1$-$C_6$ alkyl, and hydrazinyl; and $R^5$ is selected from the group consisting of hydrogen, $C_1$-$C_6$ alkyl, $C_2$-$C_6$ alkenyl, $C_2$-$C_6$ alkynyl, heteroaryl, and $C_1$-$C_6$ aminoalkyl;

or a pharmaceutically acceptable salt thereof.

In a specific embodiment of the above $A_1$ AR agonists or partial agonists, $R^1$ is selected from the group consisting of hydrogen, $C_1$-$C_6$ alkyl, $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{14}$ tricycloalkyl $C_1$-$C_6$ alkyl, —CH(R$^a$)(R$^b$), and $C_6$-$C_{14}$ aryl $C_1$-$C_6$ alkyl, wherein R$^a$ and R$^b$ are independently selected from the group consisting of $C_1$-$C_6$ alkyl, $C_3$-$C_8$ cycloalkyl, and $C_6$-$C_{14}$ aryl, wherein the aryl portion of $R^1$ is optionally substituted with one or more substituents selected from the group consisting of halo, $C_1$-$C_6$ alkoxy, and halo $C_1$-$C_6$ alkoxy.

In an embodiment of the above $A_1$ AR agonists or partial agonists, $R^2$ is heterocyclyl, e.g., pyrazolyl or tetrazolyl, optionally substituted with one or more substituents selected from the group consisting of pyridyl, alkyl pyridyl, haloalkyl pyridyl, trihaloalkyl pyridyl, carboxy pyridyl, quinolinyl, quinazolinyl; and in certain embodiments, $R^2$ is pyrazolyl, optionally substituted with one or more substituents selected from the group consisting of 4-pyridyl, 4-alkyl-2-pyridyl, 4-trihaloalkyl-2-pyridyl, 4-carboxy-2-pyridyl, 2-pyrazinyl, 2-quinolinyl, and 2-quinazolinyl. An example of an 4-alkyl-2-pyridyl is 4-methyl pyridyl. An example of a 4-trihaloalkyl pyridyl is 4-trifluoromethyl pyridyl.

In an embodiment, $R^2$ is a heterocyclyl group selected from the group consisting of:

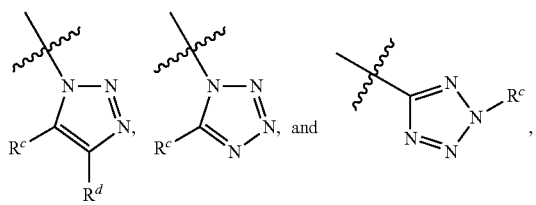

wherein R$^c$ and R$^d$ are independently chosen from hydrogen, optionally substituted alkyl, optionally substituted aryl, optionally substituted heteroaryl, —$CO_2H$, —$SO_3H$, —C(O)OR$^e$, —CH(OH)R$^e$, or C(O)NR$^e$R$^f$, wherein R$^e$ or R$^f$ is hydrogen, optionally substituted alkyl, optionally substituted cycloalkyl, optionally substituted aralkyl, optionally substituted aryl, or optionally substituted heteroaryl.

In any of the above $A_1$ AR agonists or partial agonists, $R^3$ and $R^4$ are particularly hydroxyl.

In any of the above $A_1$ AR agonists or partial agonists, $R^5$ is particularly hydrogen.

In any of the above $A_1$ AR agonists or partial agonists, $R^2$ is halo, preferably chloro.

In any of the above $A_1$ AR agonists or partial agonists, wherein $R^1$ is selected from the group consisting of:

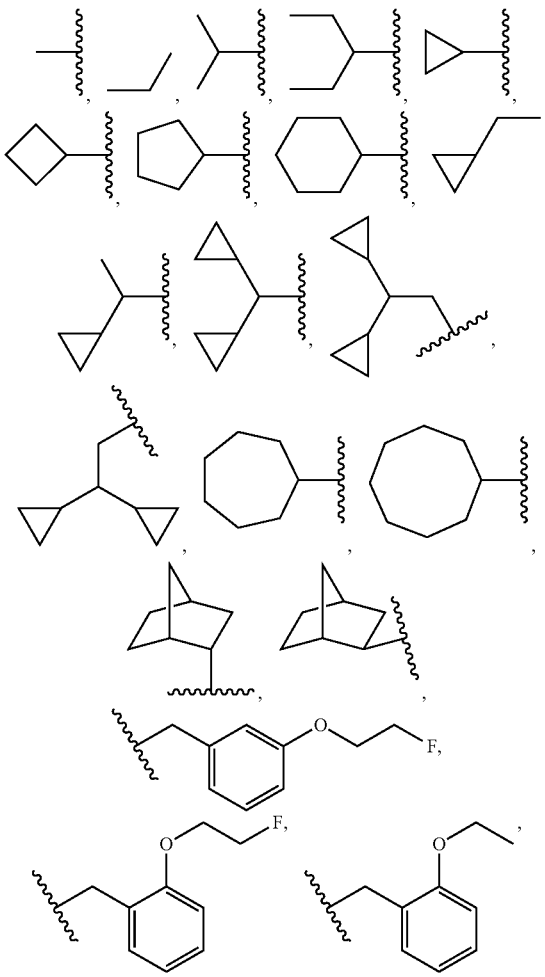

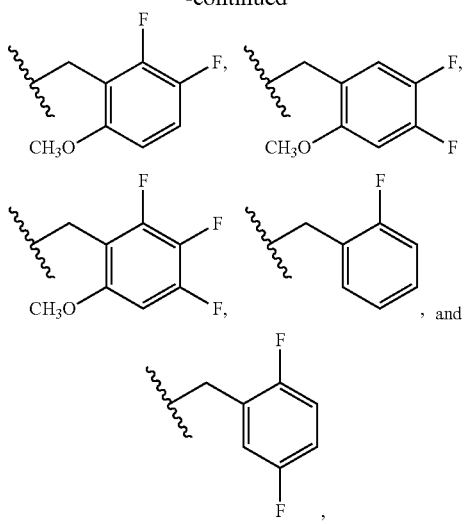

$R^2$ is chloro, $R^3$ and $R^4$ are hydroxyl, and $R^5$ is hydrogen.

Specific examples of above $A_1$ AR agonists or partial agonists include compounds of the formula (Ia):

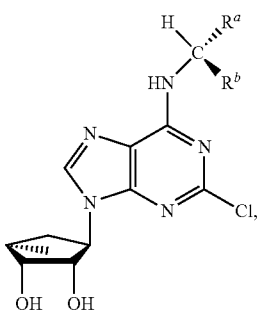

(Ia)

wherein:

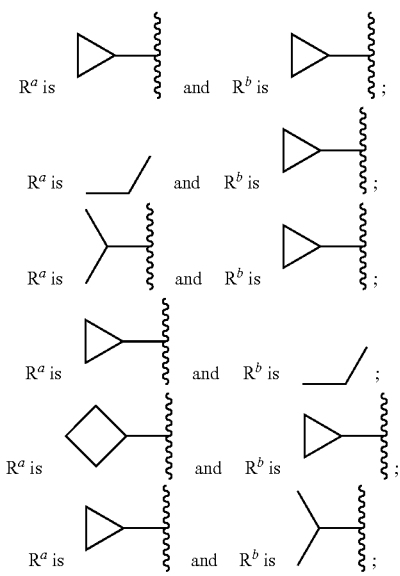

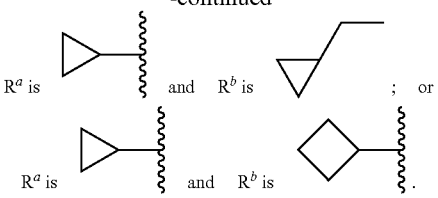

The present invention further provides a pharmaceutical composition comprising a compound as described above in any of the embodiments and a pharmaceutically acceptable carrier. The present invention provides a pharmaceutical composition comprising a pharmaceutically acceptable carrier and an effective amount, e.g., a therapeutically effective amount, including a prophylactically effective amount, of one or more of the aforesaid compounds, or salts thereof, of the present invention.

The pharmaceutically acceptable carrier can be any of those conventionally used and is limited only by chemico-physical considerations, such as solubility and lack of reactivity with the compound, and by the route of administration. It will be appreciated by one of skill in the art that, in addition to the following described pharmaceutical compositions; the compounds of the present invention can be formulated as inclusion complexes, such as cyclodextrin inclusion complexes, or liposomes.

The pharmaceutically acceptable carriers described herein, for example, vehicles, adjuvants, excipients, or diluents, are well known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be deter mined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The present invention also provides a method of treating a disease in an animal, e.g., a mammal, comprising administering to the animal an effective amount of a compound or a pharmaceutically acceptable salt of the invention, wherein the disease is selected from the group consisting of cancer, glaucoma, inflammatory diseases, asthma, stroke, myocardial infarction, allergic reactions, rhinitis, poison ivy induced responses, urticaria, scleroderma, arthritis, brain arteriole diameter constriction, bronchoconstriction, and myocardial ischemia. The invention also provides, in an embodiment, a method for selectively inactivating an $A_3$ adenosine receptor, or partially activating an $A_3$ adenosine receptor, in as animal in need thereof, comprising administering to the mammal an effective amount of a compound or pharmaceutically acceptable salt of the invention. The methods of the invention can be applied to any suitable mammal, particularly human.

The present invention further provides a method of treating a disease in a mammal comprising administering to the mammal an effective amount of any of the above agonists or partial agonists of the $A_1$ AR or a pharmaceutically acceptable salt thereof, wherein the disease is selected from the group consisting of seizures, convulsions, stroke, diabetes, pain, arrhythmias, depression, and anxiety.

The present invention further provides a method of cardioprotecting or neuroprotecting a mammal in need thereof comprising administering to the mammal an effective amount of any of the above agonists or partial agonists of the $A_1$ AR or a pharmaceutically acceptable salt thereof, wherein in the cardioprotection is in ischemia and the neuroprotection is in ischemia, seizure, or epilepsy.

The present invention further provides a method for partially or fully activating an $A_1$ adenosine receptor in a mammal in need thereof comprising administering to the mammal an effective amount of any of the above agonists or partial agonists of the $A_1$ AR or a pharmaceutically acceptable salt thereof.

The term "animal" refers to any member of the animal kingdom. In embodiments, "animal" refers to a human at any stage of development. In embodiments, "animal" includes mammals, birds, reptiles, amphibians, fish, and worms. In certain embodiments, the non-human animal is a mammal, e.g., a rodent, a mouse, a rat, a rabbit, a monkey, a dog, a cat, a sheep, cattle, a primate, or a pig. The animal may also be a transgenic animal, genetically engineered animal, or a clone.

The present invention further provides a method for inactivating $A_3$ adenosine receptors, or partially activating such a receptor, in a cell comprising contacting the cell with an effective amount of one or more of the inventive compounds or a pharmaceutically acceptable salt thereof. The contacting can be in vitro or in vivo. When the contacting is done in vitro, the contacting can be done by any suitable method, many of which are known in the art. For example, the cell can be provided in a culture medium and the inventive compound introduced into the culture medium per se, or as a solution of the compound in an appropriate solvent.

The present invention further provides a method of cardio-protection for preventing or reducing ischemic damage to the heart in an animal in need thereof comprising administering to the animal a compound or salt as described above, particularly, a compound or salt of formula I, wherein $R^1$ is 3-bromobenzyl or 3-iodobenzyl, $R^2$ is halo, $R^3$ and $R^4$ are hydroxyl, and $R^5$ is hydrogen.

The compounds or salts thereof can be used in any suitable dose. Suitable doses and dosage regimens can be determined by conventional range finding techniques. Generally treatment is initiated with smaller dosages, which are less than the optimum dose. Thereafter, the dosage is increased by small increments until optimum effect under the circumstances is reached. For convenience, the total daily dosage may be divided and administered in portions during the day if desired. In proper doses and with suitable administration of certain compounds, the present invention provides for a wide range of responses. Typically the dosages range from about 0.001 to about 1000 mg/kg body weight of the animal being treated/day. For example, in embodiments, the compounds or salts may be administered from about 100 mg/kg to about 300 mg/kg, from about 120 mg/kg to about 280 mg/kg, from about 140 mg/kg to about 260 mg/kg, from about 150 mg/kg to about 250 mg/kg, from about 160 mg/kg to about 240 mg/kg, of subject body weight per day, one or more times a day, to obtain the desired therapeutic effect.

In accordance with another embodiment, the invention provides isotopically labeled compounds described above, for example, compounds labeled with a radioactive or non-radioactive isotope, for use in the determination of drug/tissue distribution assays, in the manipulation of oxidative metabolism via the primary kinetic isotope effect, in identifying potential therapeutic agents for the treatment of diseases or conditions associated with target-receptor mediation. The compounds of the invention can be prepared with a radioactive isotope. Any suitable atom can be replaced with a radioactive isotope, for example, a carbon atom, hydrogen atom, a halogen atom, a sulfur atom, nitrogen atom, or an oxygen atom can be replaced with a corresponding isotope. Thus, for example, a halogen atom can be replaced with $^{18}F$, $^{36}Cl$, $^{75}Br$, $^{76}Br$, $^{77}Br$, $^{82}Br$, $^{122}I$, $^{123}I$, $^{125}I$, or $^{131}I$. The use of radiolabeled compounds that may be detected using imaging techniques, such as the Single Photon Emission Computerized Tomography (SPECT), Magnetic Resonance Spectroscopy (MRS), or the Positron Emission Tomography (PET), are known in the art. See, for example, U.S. Pat. Nos. 6,395,742 and 6,472,667.

In accordance with a further embodiment, the invention provides a radiolabeled compound of Formula I:

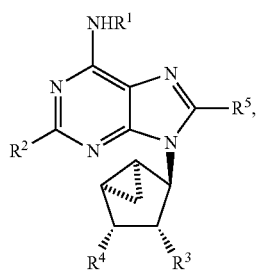

(I)

wherein $R^1$ is selected from the group consisting of $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkoxy, $C_6$-$C_{14}$ aryl sulfonyl, heterocyclyl $C_1$-$C_6$ alkyl, heterocyclyl, heteroaryl $C_1$-$C_6$ alkyl, 4-[[[4-[[[(2-amino $C_1$-$C_6$ alkyl)amino]-carbonyl]-$C_1$-$C_6$ alkyl]aniline] carbonyl]$C_1$-$C_6$ alkyl]$C_6$-$C_{14}$ aryl, and $C_6$-$C_{14}$ aryl $C_3$-$C_8$ cycloalkyl, wherein the aryl or heterocyclyl portion of $R^1$ is substituted with one or more halogen atoms that are radioactive;

$R^2$ is selected from the group consisting of hydrogen, halo, amino, hydrazido, mercapto, $C_1$-$C_{20}$ alkylamino, $C_6$-$C_{14}$ aryl amino, $C_6$-$C_{14}$ aryloxy, $C_1$-$C_{20}$ alkyl, $C_1$-$C_{20}$ alkoxy, $C_1$-$C_{20}$ thioalkoxy, pyridylthio, $C_7$-$C_{12}$ cycloalkyl $C_1$-$C_{20}$ alkyl, $C_7$-$C_{12}$ bicycloalkyl $C_1$-$C_{20}$ alkyl, $C_7$-$C_{12}$ bicycloalkenyl $C_1$-$C_{20}$ alkyl, $C_6$-$C_{14}$ aryl $C_1$-$C_{20}$ alkyl, $C_2$-$C_{20}$ alkenyl, $C_7$-$C_{12}$ cycloalkyl $C_2$-$C_{20}$ alkenyl, $C_7$-$C_{12}$ bicycloalkyl $C_2$-$C_{20}$ alkenyl, $C_7$-$C_{12}$ bicycloalkenyl $C_2$-$C_{20}$ alkenyl, $C_6$-$C_{14}$ aryl $C_2$-$C_{20}$ alkenyl, $C_2$-$C_{20}$ alkynyl, carboxy alkyl $C_2$-$C_{20}$ alkynyl, $(CH_2)_m$—C(=O)—O—$C_1$-$C_6$ alkyl, —C≡C—$(CH_2)_m$—C(=O)—NH—$(CH_2)_n$—$NH_2$, —C≡C—$(CH_2)_m$—$C_1$-$C_6$ alkyl, —C≡C—$(CH_2)_m$-aryl, wherein m and n are independently 1 to 10, $C_7$-$C_{12}$ cycloalkyl $C_2$-$C_{20}$ alkynyl, $C_7$-$C_{12}$ bicycloalkyl $C_2$-$C_{20}$ alkynyl, $C_7$-$C_{12}$ bicycloalkenyl $C_2$-$C_{20}$ alkynyl, $C_6$-$C_{14}$ aryl $C_2$-$C_{20}$ alkynyl, and the alkyl, cycloalkyl, or aryl portion of $R^2$ is optionally substituted with one or more substituents selected from the group consisting of halo, hydroxyl, amino, alkylamino, dialkylamino, sulfur, carboxy, alkoxycarbonyl, aminocarbonyl, alkylaminocarbonyl, dialkyl aminocarbonyl, aminoalkyl aminocarbonyl, and trialkylsilyl;

$R^3$ and $R^4$ are independently selected from the group consisting of hydroxyl, amino, thiol, ureido, $C_1$-$C_6$ alkyl carbonylamino, hydroxy $C_1$-$C_6$ alkyl, and hydrazinyl; and $R^5$ is selected from the group consisting of hydrogen, $C_1$-$C_6$ alkyl, $C_2$-$C_6$ alkenyl, $C_2$-$C_6$ alkynyl, heteroaryl, and $C_1$-$C_6$ aminoalkyl;

or a pharmaceutically acceptable salt thereof.

The halogen atom of the radiolabeled compound or salt in $R^1$ of the invention can be any suitable isotope, for example, $^{18}F$, $^{76}Br$, or $^{125}I$, preferably $^{76}Br$ or $^{125}I$.

In a particular embodiment, the invention provides radiolabeled compounds or salts wherein $R^1$ is 3-bromobenzyl or 3-iodobenzyl, $R^2$ is halo, $R^3$ and $R^4$ are hydroxyl, and $R^5$ is hydrogen.

Accordingly, the present invention further provides a method of diagnostic imaging of an $A_3$ adenosine receptor in a tissue or organ of an animal comprising administering an effective amount of a radiolabeled compound or salt as described above to the animal and obtaining an image of the organ or tissue of the animal. The image can be obtained by any suitable imaging technique, for example, SPECT, MRS, and/or PET.

The present invention also provides a diagnostic method for determining a treatment of a patient for a possible agonist or antagonist of the $A_3$ adenosine receptors, the treatment comprising:

(a) administering a radiolabeled compound or salt as described above;

(b) obtaining a biological sample from the patient;

(c) determining the level of expression of the $A_3$ adenosine receptor;

(d) comparing the level of expression of the receptor to that of a normal population; and (e) if the patient's level of expression is higher than that of the normal population, determining a treatment regimen comprising administering an agonist or antagonist of the adenosine receptor whose expression was higher in the patient than that of the normal population.

The following examples further illustrate the invention but, of course, should not be construed as in any way limiting its scope.

EXAMPLE 1

This example demonstrates a method of preparing compounds in accordance with an embodiment of the invention. D-ribose was protected with TBDPS-Cl followed by alkaline hydrolysis, thus providing acid 2. Reductive decarboxylation of acid 2 was carried out using non-toxic tris(trimethylsilyl) silane as a hydrogen donor and produced the silyl ether 3 in 40% yield. The silyl ether 3 was deprotected with TBAF. The resultant alcohol 4 was converted into a key dichloropurine derivative 6 through a Mitsonobu reaction (FIG. 1). Derivative 6 reacted with an excess of the corresponding primary amine to give the $N^6$ substituted and 2',3'-isopropylidene protected derivatives compounds 7a-13a, followed by acid catalyzed deprotection to give the $N^6$-3-halobenzyl and related arylmethyl derivatives 7b-13b.

(1R,2S,3R,4R,5R)-3,4-O-(Isopropylidene)-2-O-(tert-butyldiphenylsilyl)-2,3,4-trihydroxybicyclo[3.1.0]hexane-1-carboxylic acid (2)

tert-Butyldiphenylsilyl chloride (2.70 g, 10 mmol) and triethylamine (2.0 g, 20 mmol) were added to a solution of alcohol 1 (prepared from D-ribose following the standard procedure (Joshi et al. supra) 1.22 g, 5 mmol) and imidazole (140 mg, 2 mmol) in DMF (3 mL) while stirring at room temperature. The solution was stirred at 60° C. for 16 h. The reaction mixture was cooled to room temperature and diluted with a 4:1 ethyl acetate-hexane mixture (50 mL), washed with water, dried, and solvent was evaporated. The residue was purified by flash chromatography (0 to 10% ethyl-acetate-hexane) to give ethyl (1R,2S,3R,4R,5R)-2,3-O-(isopropylidene)-4-O-(tert-butyldiphenylsilyl)-2,3,4-trihydroxybicyclo[3.1.0]hexane-1-carboxylate. The compound was dissolved in MeOH (5 mL), 2N aq. NaOH (5 mL) was added, and the reaction mixture was refluxed for 2 h. The reaction mixture was neutralized with $NaH_2PO_4$, and extracted with DCM. The combined DCM solutions were dried and evaporated, and the residue was purified by flash chromatography to give title compound 2 (1.65 g, 73%). $^1$H NMR (CDCl$_3$), δ: 7.72 (d, 4H, J=7.8 Hz), 7.39 (m, 6H), 5.05 (d, 1H, J=6.3 Hz), 4.43 (t, 1H, J=6.0 Hz), 4.08 (t, 1H, J=6.6 Hz), 2.26 (m, 1H), 1.97 (s, 3H), 1.56 (s, 3H), 1.52 (m, 1H), 1.21 (s, 3H), 1.08 (s, 9H).

(1S,2S,3R,4R,5R)-3,4-O-(Isopropylidene)-2-O-(tert-butyldiphenylsilyl)-2,3,4-trihydroxybicyclo[3.1.0]hexane (3)

A 1M solution of DCC in oxygen-free toluene (0.96 mL) was added to a solution of acid 2 (363 mg, 0.80 mmol), 2-mercaptopyridine N-oxide (112 mg, 0.88 mmol), and AIBN (40 mg, 0.24 mmol) in dry oxygen-free toluene (4 mL). The reaction mixture was stirred for 4 h at 25° C., tris(trimethylsilyl)silane (0.50 mL, 1.6 mmol) was added, and the reaction mixture was heated at 85° C. for 4 h. The reaction mixture was evaporated, and the residue was separated by flash chromatography (0 to 10% ethyl acetate-hexane mixture) to afford the title compound 3 (121 mg, 40%). $^1$H NMR (CDCl$_3$), δ: 7.76 (d, 4H, J=7.8 Hz), 7.39 (m, 6H), 4.66 (t, 1H, J=6.0 Hz), 4.44 (t, 1H, J=6.6 Hz), 4.03 (t, 1H, J=6.6 Hz), 1.6 (m, 1H), 1.57 (s, 3H), 1.45 (m, 1H), 1.33 (s, 1H), 1.20 (s, 3H), 1.09 (s, 9H), 0.58 (m, 1H).

(1R,2R,3S,4S,5S)-2.3-O-(Isopropylidene)-2,3,4-trihydroxybicyclo[3.1.0]hexane (4), Method B A 1M solution of tert-butylammonium fluoride in THF (1 mL) was added to a solution of silylether 3 (102 mg, 0.25 mmol) in THF (1 mL). The reaction mixture was left at 20° C. for 16 h and evaporated. The residue was diluted with ethyl acetate (20 mL) and washed with a small amount of brine. The ethyl acetate solution was dried and evaporated, and the residue was purified by flash chromatography to afford the title compound 4 (33 mg, 84%). $^1$H NMR and MS are provided under Method A.

General Procedure for Preparation of Compounds 7b-13b.

An amine ($RNH_2$ in Scheme 3, 0.5 mmol) was added to a solution of 6 (20 mg, 0.06 mmol) in DCM (0.1 mL). The reaction mixture was stirred at room temperature for 16 h. The solvent was removed under vacuum, and the residue was separated by flash chromatography (30 to 100% ethyl acetate-hexane) to afford the corresponding 6-alkylaminopurine derivative that was dissolved in a mixture of MeOH (4 mL), TFA (0.2 mL) and water (2 mL). The reaction mixture was stirred at 70° C. for 16 h, and then evaporated. The residue was evaporated twice with water, and the residue was purified by flash chromatography (50 to 100% ethyl acetate).

(1'R,2'R,3'S,4'R,5'S)-4'-[2-Chloro-6-(3-iodobenzylamino)purine]-2',3'-O-dihydroxybicyclo-[3.1.0]hexane (7b)

Yield 15 mg (51% $^1$H NMR (CD$_3$OD), δ: 8.16 (s, 1H), 7.49 (s, 1H), 7.60 (d, 1H, 8.5 Hz), 7.40 (d, 1H, 8.5 Hz), 7.10 (t, 1H, 8.5 Hz), 4.71 (s, 2H), 3.90 (d, 3.3 Hz, 1H), 3.65 (s, 1H), 2.05-1.95 (m, 1H), 1.67-1.63 (m, 1H), 1.36 (s, 1H), 1.31-1.27 (m, 1H), 0.95-0.87 (m, 1H), 0.77-0.75 (m, 1H). HRMS calculated for $C_{18}H_{18}ClIN_5O_2^+$ (M+H)$^+$: 498.0194. found, 498.0194. HPLC: RT 21.6 min (98%) in solvent system A, 17.0 min (98%) in system B.

(1'R,2'R,3'S,4'R,5'S)-4'-[2-Chloro-6-(3-chlorobenzylamino)purine]-2',3'-O-dihydroxybicyclo-[3.1.0]hexane (8b)

Yield 58%. $^1$H NMR (CD$_3$OD), δ: 8.16 (br.s., 1H), 7.41 (s, 1H), 7.29 (m, 3H), 4.79 (s, 1H), 4.75 (br. s, 2H), 4.70 (br. t., 1H, J=5.4 Hz), 3.86 (d, 1H, J=6.6 Hz), 1.97 (m, 1H), 1.65 (m, 1H), 1.30 (m, 1H), 0.75 (m, 1H). HRMS (ESI MS m/z): calculated for $C_{18}H_{18}Cl_2N_5O_2^+$ (M+H)$^+$, 406.0832. found, 406.0825. HPLC RT 20.3 min (98%) in solvent system A, 15.6 min (98%) in system B.

(1'R,2'R,3'S,4'R,5'S)-4'-[2-Chloro-6-(3-bromobenzylamino)purine]-2',3'-O-dihydroxybicyclo-[3.1.0]hexane (9b)

Yield 65%. $^1$H NMR (CD$_3$OD): 8.03 (s, 1H), 7.45 (s, 1H), 7.29 (m, 2H), 7.12 (t, 1H, J=7.8 Hz), 4.68 (s, 1H), 4.63 (br. s, 2H), 4.59 (br. t., 1H, J=5.4 Hz), 3.79 (d, 1H, J=6.6 Hz), 1.86 (m, 1H), 1.55 (m, 1H), 1.20 (m, 1H), 0.64 (m, 1H). HRMS (ESI MS m/z) calculated for $C_{18}H_{18}BrClN_5O_2^+$ (M+H)$^+$, 450.0327. found 450.0315. HPLC RT 20.74 min (98%) in solvent system A, 16.1 min (99%) in system B.

(1'R,2'R,3'S,4'R,5'S)-4'-[2-Chloro-6-(1-naphthylamino)purine]-2',3'-O-dihydroxybicyclo[3.1.0]hexane (10b)

Yield 48%. $^1$H NMR (CD$_3$OD): 8.13 (br. d., 2H, J=7.8 Hz), 7.84 (m, 2H), 7.49 (m, 4H), 5.21 (s, 1H), 4.79 (br. s, 1H), 4.78

(br. s, 2H), 4.67 (br. t., 1H, J=5.1 Hz), 3.88 (d, 1H, J=6.6 Hz), 1.93 (m, 1H), 1.62 (m, 1H), 1.25 (m, 1H), 0.73 (m, 1H). HRMS (ESI MS m/z) calculated for $C_{22}H_{25}ClN_5O_2^+$ (M+H)$^+$, 422.1378. found 422.1385. HPLC RT 21.5 min (97%) in solvent system A, 17.0 min (98%) in system B.

(1'R,2'R,3'S,4'R,5'S)-4'-[2-Chloro-6-(2,5-dimethoxybenzylamino)purine]-2',3'-O-dihydroxybicyclo-[3.1.0]hexane (11b)

Yield 44%. $^1$H NMR (CD$_3$OD): 8.4 (very br. s, 1H), 6.95 (s, 1H, J=2.7 Hz), 6.89 (d, 1H, J=9.3 Hz), 6.78 (dd, 1H, J=2.7, 9.0 Hz), 4.80 (s, 1H), 4.75 (br. m, 3H), 3.87 (d, 1H, J=6.3 Hz), 3.83 (s, 3H), 3.71 (s, 3H), 1.95 (m, 1H), 1.64 (m, 1H), 1.29 (m, 1H), 0.74 (m, 1H). HRMS (ESI MS m/z) calculated for $C_{20}H_{23}ClN_5O_4^+$ (M+H)$^+$, 432.1433. found 432.1439. HPLC RT 18.7 min (98%) in solvent system A, 16.6 min (98%) in system B.

(1'R,2'R,3'S,4'R,5'S)-4'-[2-Chloro-6-(2-hydroxy-5-methoxybenzylamino)purine]-2',3'-O-dihydroxybicyclo-[3.1.0]hexane (12b)

Yield 39%. $^1$H NMR (CD$_3$OD): 8.07 (s, 1H), 6.60-6.82 (m, 3H), 4.69 (s, 1H), 4.59 (br. t., 1H, J=6.0 Hz), 4.56 (br. s, 2H), 3.79 (d, 1H, J=6.6 Hz), 3.61 (s, 3H) 1.86 (m, 1H), 1.55 (m, 1H), 1.20 (m, 1H), 0.65 (m, 1H). HRMS (ESI MS m/z) calculated for $C_{19}H_{21}ClN_5O_4^+$ (M+H)$^+$, 418.1277. found, 418.1277. HPLC RT 16.0 min (100%) in solvent system A, 11.0 min (98%) in system B.

(1'R,2'R,3'S,4'R,5'S)-4'-[2-Chloro-6-(trans-2-phenylcyclopropylamino)purine]-2',3'-O-dihydroxybicyclo-[3.1.0]hexane (13b)

Yield 52%. $^1$H NMR (CD$_3$OD): 8.16 (very br.s., 1H), 7.0-7.48 (m, 5H), 4.79 (s, 1H), 4.68 (br. s, 2H), 3.88 (d, 1H, J=5.7 Hz), 2.17 (m, 1H) 1.97 (m, 1H), 1.65 (m, 1H), 1.29 (m, 2H), 0.74 (m, 1H). HRMS (ESI MS m/z) calculated for $C_{20}H_{21}ClN_5O_2^+$ (M+H)$^+$, 398.1378. found, 398.1372. HPLC RT 20.3 min (99%) in solvent system A, 15.6 min (98%) in system B.

EXAMPLE 2

This Example illustrates the ability of the compounds in accordance with an embodiment of the invention to bind to A$_3$ adenosine receptors. The binding affinity values are set forth in Table 1.

Receptor Binding and Functional Assays

[$^{125}$I]N$^6$-(4-Amino-3-iodobenzyl)adenosine-5'-N-methyluronamide (I-AB-MECA; 2000 Ci/mmol), [$^3$H]cyclic AMP (40 Ci/mmol), and other radioligands were purchased from Perkin-Elmer Life and Analytical Science (Boston, Mass.). [$^3$H]CCPA (2-chloro-N$^6$-cyclopentyladenosine) was a custom synthesis product (Perkin Elmer). Test compounds were prepared as 5 mM stock solutions in DMSO and stored frozen.

Cell culture and membrane preparation: CHO (Chinese hamster ovary) cells expressing the recombinant human A$_3$AR were cultured in DMEM (Dulbecco's modified Eagle's medium) supplemented with 10% fetal bovine serum, 100 units/mL penicillin, 100 μg/mL streptomycin, 2 μmol/mL glutamine and 800 μg/mL geneticin. The CHO cells expressing rat A$_3$ARs were cultured in DMEM and F12 (1:1). Cells were harvested by trypsinization. After homogenization and suspension, cell membranes were centrifuged at 500 g for 10 min, and the pellet was re-suspended in 50 mM Tris.HCl buffer (pH 8.0) containing 10 mM MgCl$_2$, 1 mM EDTA and 0.1 mg/mL CHAPS (3[(3-cholamidopropyl)dimethylammonio]-propanesulfonic acid). The suspension was homogenized with an electric homogenizer for 10 sec, and was then re-centrifuged at 20,000 g for 20 min at 4° C. The resultant pellets were resuspended in buffer in the presence of adenosine deaminase (3 Units/mL), and the suspension was stored at −80° C. until the binding experiments. The protein concentration was measured using the Bradford assay. Bradford, M. M. *Anal. Biochem.* 1976, 72, 248.

Binding assays at the A$_1$ and A$_{2A}$ receptors: For binding to human A$_1$ receptors, see (a) Schwabe, U.; Trost, T. *Naunyn-Schmiedeberg's Arch. Pharmacol.* 1980, 313, 179. (b) Pereira, M.; Jiang, J. K.; Klutz, A. M.; Gao, Z. G.; Shainberg, A.; Lu, C.; Thomas, C. J.; Jacobson, KA. *J. Med. Chem.* 2005, 48, 4910.

[$^3$H]R-PIA (N$^6$-[(R)-phenylisopropyl]adenosine, 2 nM) or [$^3$H]CCPA (0.5 nM) was incubated with membranes (40 μg/tube) from CHO cells stably expressing human A$_1$ receptors at 25° C. for 60 min in 50 mM Tris.HCl buffer (pH 7.4; MgCl$_2$, 10 mM) and increasing concentrations of the test ligand in a total assay volume of 200 μl. Nonspecific binding was determined using 10 μM of CPA (N$^6$-cyclopentyladenosine). For human A$_{2A}$ receptor binding (Jarvis, M. F.; Schutz, R.; Hutchison, A. J.; Do, E.; Sills, M. A.; Williams, M. *J. Pharmacol. Exp. Ther.* 1989, 251, 888-893) membranes (20 μg/tube) from HEK-293 cells stably expressing human A$_{2A}$ receptors were incubated with [$^3$H]CGS21680 (2-[p-(2-carboxyethyl)phenyl-ethylamino]-5'-N-ethylcarboxamido-adenosine, 15 nM) and increasing concentrations of the test ligand at 25° C. for 60 min in 200 μl 50 mM Tris.HCl, pH 7.4, containing 10 mM MgCl$_2$. NECA (10 μM) was used to define nonspecific binding. The reaction was terminated by filtration with GF/B filters.

Binding assay at the human A$_3$ receptor: For the competitive binding assay, each tube contained 50 μL membrane suspension (20 μg protein), 25 μL of [$^{125}$I]I-AB-MECA (1.0 nM), Olah, M. E., Gallo-Rodriguez, C., Jacobson, K. A., Stiles, G. L. *Mol. Pharmacol.* 1994, 45, 978, and 25 μL of increasing concentrations of the test ligands in Tris.HCl buffer (50 mM, pH 8.0) containing 10 mM MgCl$_2$, 1 mM EDTA. Nonspecific binding was determined using 10 μM of Cl-IB-MECA in the buffer. The mixtures were incubated at 37° C. for 60 min. Binding reactions were terminated by filtration through Whatman GF/B filters under reduced pressure using a MT-24 cell harvester (Brandell, Gaithersburgh, Md., USA). Filters were washed three times with 9 mL ice-cold buffer. Radioactivity was determined in a Beckman 5500B γ-counter. IC$_{50}$ values were converted to K$_i$ values as described in Cheng, Y.; Prusoff, W. H. *Biochem. Pharmacol.* 1973, 22, 3099.

Cyclic AMP accumulation assay: Intracellular cyclic AMP levels were measured with a competitive protein binding method. Nordstedt, C.; Fredholm, B. B. *Anal. Biochem.* 1990, 189, 231; Post, S. R.; Ostrom, R. S.; Insel, P. A. *Methods Mol. Biol.* 2000, 126, 363.

CHO cells that expressed the recombinant human or rat A$_3$AR or the human A$_1$ or A$_{2B}$AR were harvested by trypsinization. After centrifugation and resuspended in medium, cells were planted in 24-well plates in 1.0 mL medium. After 24 h, the medium was removed and cells were washed three times with 1 mL DMEM, containing 50 mM HEPES, pH 7.4. Cells were then treated with the agonist NECA and/or test compound (e.g. 7b) in the presence of rolipram (10 μM) and adenosine deaminase (3 units/mL).

After 45 min forskolin (10 μM) was added to the medium, and incubation was continued for an additional 15 min. The reaction was terminated by removing the supernatant, and cells were lysed upon the addition of 200 μL of 0.1 M ice-cold HCl. The cell lysate was resuspended and stored at −20° C. For determination of cyclic AMP production, protein kinase A (PKA) was incubated with [$^3$H]cyclic AMP (2 nM) in $K_2HPO_4$/EDTA buffer ($K_2HPO_4$, 150 mM; EDTA, 10 mM), 20 μL of the cell lysate, and 30 μL 0.1 M HCl or 50 μL of cyclic AMP solution (0-16 pmol/200 μL for standard curve). Bound radioactivity was separated by rapid filtration through Whatman GF/C filters and washed once with cold buffer. Bound radioactivity was measured by liquid scintillation spectrometry.

[$^{35}$S]GTPγS binding assay: [$^{35}$S]GTPγS binding was measured by a variation of the method described. (a) Lorenzen, A.; Lang H.; Schwabe U. *Biochem. Pharmacol.* 1998, 56, 1287. (b) Jacobson, K. A.; Ji, X.-d.; Li, A. H.; Melman, N.; Siddiqui, M. A.; Shin, K. J.; Marquez, V. E.; Ravi, R. G. *J. Med. Chem.* 2000, 43, 2196. Each assay tube consisted of 200 μL buffer containing 50 mM Tris HCl (pH 7.4), 1 mM EDTA, 1 mM $MgCl_2$, 1 μM GDP, 1 mM dithiothreitol, 100 mM NaCl, 3 U/ml ADA, 0.2 nM [$^{35}$S]GTPγS, 0.004% 3-[(3-cholamidopropyl)dimethylammonio]propanesulfonate (CHAPS), and 0.5% bovine serum albumin. Incubations were started upon addition of the membrane suspension (CHO cells stably expressing either the native human $A_1$AR or $A_3$AR, 5 μg protein/tube) to the test tubes, and they were carried out in duplicate for 30 min at 25° C. The reaction was stopped by rapid filtration through Whatman GF/B filters, pre-soaked in 50 mM Tris HCl, 5 mM $MgCl_2$ (pH 7.4) containing 0.02% CHAPS. The filters were washed twice with 3 mL of the same buffer, and retained radioactivity was measured using liquid scintillation counting. Non-specific binding of [$^{35}$S]GTPγS was measured in the presence of 10 μM unlabelled GTPγS. None of the compounds >10% stimulation; thus, they are antagonists of the $A_3$ adenosine receptor.

$A_{2A}$AR, respectively). The most $A_3$AR selective compound was the 3-chloro analogue 8b with 2900-fold and 4250-fold selectivity in comparison to the $A_1$ and $A_{2A}$AR, respectively. The SAR of substitution of the $N^6$-benzyl group further showed that dimethoxy substitution (11b), fusion of the phenyl ring to a second ring (10b), and extension by one carbon (i.e., in the rotationally constrained 2-phenylcyclopropyl analogue, 13b) were all tolerated with nanomolar binding affinity at the $A_3$AR. Compound 12b, a demethylated analogue of 11b, was slightly less potent in binding to the $A_3$AR.

In a functional assay of [$^{35}$S]GTPγS binding induced by $A_3$AR activation, 7b completely inhibited stimulation by 1 μM NECA (5'-N-ethylcarboxamidoadenosine) with an $IC_{50}$ of 29.8 nM (FIG. 1). Schild analysis of the right shifts by 7b of the response curves in the inhibition of adenylate cyclase by NECA provided a $K_B$ value of 8.9 nM.

When compared in the ability to stimulate the $A_3$AR using multiple functional criteria, different results were obtained. In the cAMP assays, compounds 7b and 9b exhibited partial agonism at $A_3$AR with percent relative efficacies of 44±6 and 46±4, respectively, and the $EC_{50}$ values were respectively, 12±1 and 4.2±0.6 nM.

EXAMPLE 3

Figure 6:
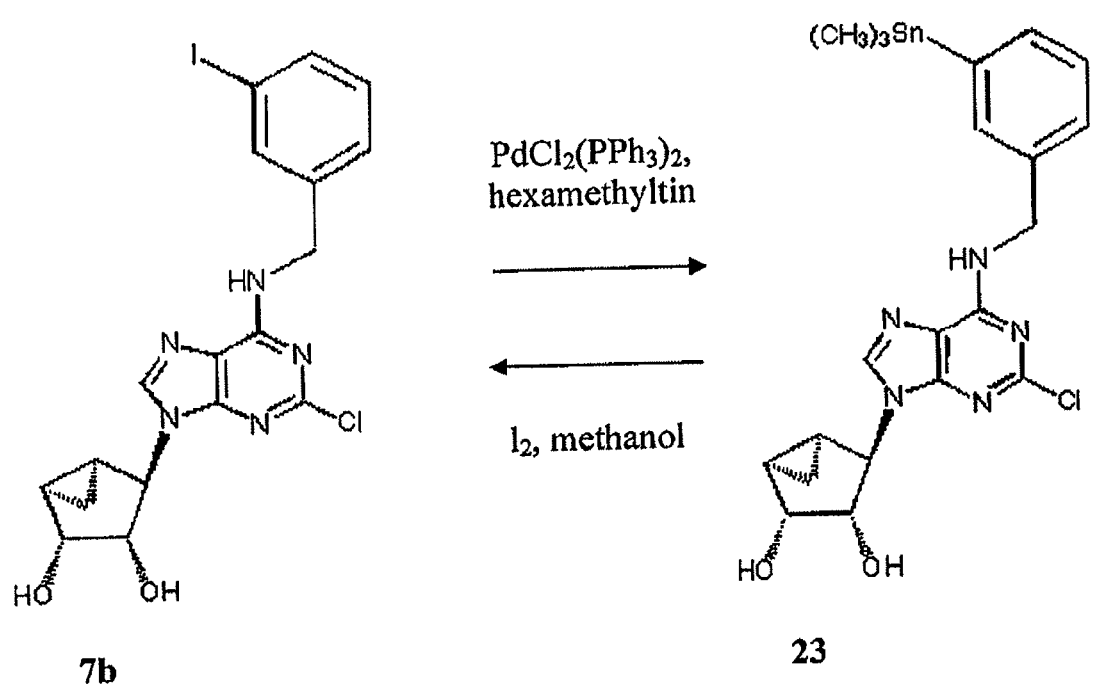
FIG. 6 depicts the (radio)iodination of compound 7b on its $N^6$-3-iodobenzyl substituent via iododestannylation of a 3-(trimethylstannyl)benzyl precursor through a "cold" iodination reaction.

This example illustrates a method of preparing a radioiodinated compound in accordance with an embodiment of the invention. Compound 7b having $^{125}$I was prepared as follows. The (radio)iodination of compound 7b on its $N^6$-3-iodobenzyl substituent was accomplished in high yield by iododestannylation of a 3-(trimethylstannyl)benzyl precursor through a "cold" iodination reaction as shown in FIG. 6.

Materials and Instrumentation.

Hexamethyltin and other reagents, including pharmacological agents, were purchased from Sigma-Aldrich Chemical Company, except where noted. Sodium [$^{125}$I]iodide (17.4 Ci/mg) in NaOH ($1.0 \times 10^{-5}$ M) was supplied by Perkin-Elmer Life and Analytical Science. $^1$H NMR spectra were obtained with a Varian Gemini 300 spectrometer using $CDCl_3$ and $CD_3OD$ as solvents. Chemical shifts are expressed in δ values

TABLE 1

Affinity data for compounds in accordance with an embodiment of the invention.

| | In Formula I, $R^2$ = Cl, $R^3$ and $R^4$ = OH and $R^5$ = H | Affinity ($K_i$, nM) or % inhibition[a] | | | % Efficacy[b] |
|---|---|---|---|---|---|
| Compound | $R^1$ | $A_1$ | $A_{2A}$ | $A_3$ | $A_3$ |
| 7b | 3-I-Phenyl-$CH_2$ | 3040 ± 610 | 1080 ± 310 | 1.44 ± 0.60 | 1.0 ± 3.2 |
| 8b | 3-Cl-Phenyl-$CH_2$ | 3070 ± 1500 | 4510 ± 910 | 1.06 ± 0.36 | 2.9 ± 3.7 |
| 9b | 3-Br-Phenyl-$CH_2$ | 1760 ± 1010 | 1600 ± 480 | 0.73 ± 0.30 | 5.8 ± 0.8 |
| 10b | 1-Naphthyl-$CH_2$ | 1120 ± 640 | 1530 ± 350 | 1.42 ± 0.12 | 3.1 ± 0.3 |
| 11b | 2,5-diMeO—Ph—$CH_2$ | 3000 ± 1260 | 2620 ± 730 | 1.58 ± 0.56 | 4.6 ± 3.8 |
| 12b | 2-OH-5-MeO—Ph—$CH_2$ | 1110 ± 300 | 6870 ± 1440 | 4.06 ± 0.35 | 0.4 ± 1.3 |
| 13b | trans-2-Ph-cyclopropyl | 1790 ± 1430 | 2010 ± 890 | 1.30 ± 0.39 | 9.7 ± 4.1 |

[a]All experiments were done on CHO or HEK ($A_{2A}$ only) cells stably expressing one of four subtypes of human ARs. The binding affinity for $A_1$, $A_{2A}$ and $A_3$ARs was expressed as $K_i$ values (n = 3-5) and was determined by using agonist radioligands ([$^3$H]CCPA or ([$^3$H]R-PIA), ([$^3$H]CGS21680), [$^{125}$I]I-AB-MECA, respectively. The potency at the $A_{2B}$AR was expressed as $EC_{50}$ values and was determined by stimulation of cyclic AMP production in AR-transfected CHO cells. A percent in parentheses refers to inhibition of radioligand binding at 10 μM.
[b]measured by [$^{35}$S]GTPγS binding assay.

In accordance with one method of biological assay, compounds 7b-9b (3-halobenzyl) in the (N)-methanocarba series were potent $A_3$ AR antagonists with binding $K_i$ values of 0.7-1.4 nM. Compound 9b (3-bromobenzyl analogue) proved to be the most potent $A_3$AR antagonist of this series in binding with a $K_i$ value of 0.73 nM, and it displayed high selectivity (2400-fold and 2190-fold in comparison to the $A_1$ and (ppm) with tetramethylsilane (δ 0.00) for $CDCl_3$ and water (δ 3.30) for $CD_3OD$. TLC analysis was carried out on aluminum sheets precoated with silica gel $F_{254}$ (0.2 mm) from Aldrich. HPLC mobile phases consisted of $CH_3CN$/tetrabutyl ammonium phosphate (5 mM) from 20/80 to 60/40 in 20 min, flow rate 1.0 ml/min. High-resolution mass measurements were performed on Micromass/Waters LCT Premier Electrospray Time of Flight (TOF) mass spectrometer coupled with a Waters HPLC system.

Preparation of 23: (1'R,2'R,3'S,4'R,5'S)-4'-[2-Chloro-6-(3-trimethylstannylbenzylamino)purine]-2',3'-O-dihydroxybicyclo-[3.1.0]hexane (1)

7b (8.95 mg, 0.018 mmol), $PdCl_2(PPh_3)_2$ (2.7 mg), and hexamethyltin (11 μL, 0.054 mmol) were mixed together in anhydrous dioxane (2 ml), and the resulting reaction mixture was stirred at 70° C. for 2 h. The mixture was concentrated under reduced pressure. The product was purified by flash chromatography by using $CHCl_3$: MeOH (10:1) as the eluant to afford the stannyl derivative 23 (9.3 mg, 90%) as an oil. $^1$H NMR (300 MHz, $CDCl_3$), 7.81 (s, 1H), 7.53 (s, 1H), 7.34 (m, 2H), 7.33 (m, 1H), 6.49 (br s, 1H), 4.88 (br s, 2H), 4.00 (m, 2H), 3.71 (s, 1H), 3.65 (m, 1H), 3.47 (m, 1H), 2.02 (m, 1H), 1.96 (s, 1H), 1.64 (m, 1H), 1.28 (m, 2H), 0.81 (m, 1H), 0.29 (s, 9H). HRMS (M+1)$^+$: calculated for $C_{21}H_{27}ClN_5O_2Sn^+$ (M+H)$^+$535.6338. found 536.0823 HPLC: $R_f$=22.1 min. HPLC system: 5 mM TBAP/$CH_3CN$ from 80/20 to 60/40 in 25 min, then isocratic for 2 min; flow rate of 1 ml/min.

The trimethylstannyl intermediate 23 (0.1 mg) was reacted sodium [$^{125}$I] iodide in NaOH (1.0×10$^{-5}$ M) to obtain [$^{125}$I] 7b, following the procedure disclosed in Vaidyanathan G., et al., *Nat. Protocols* 1: 707-713 (2006).

Figure 7A:
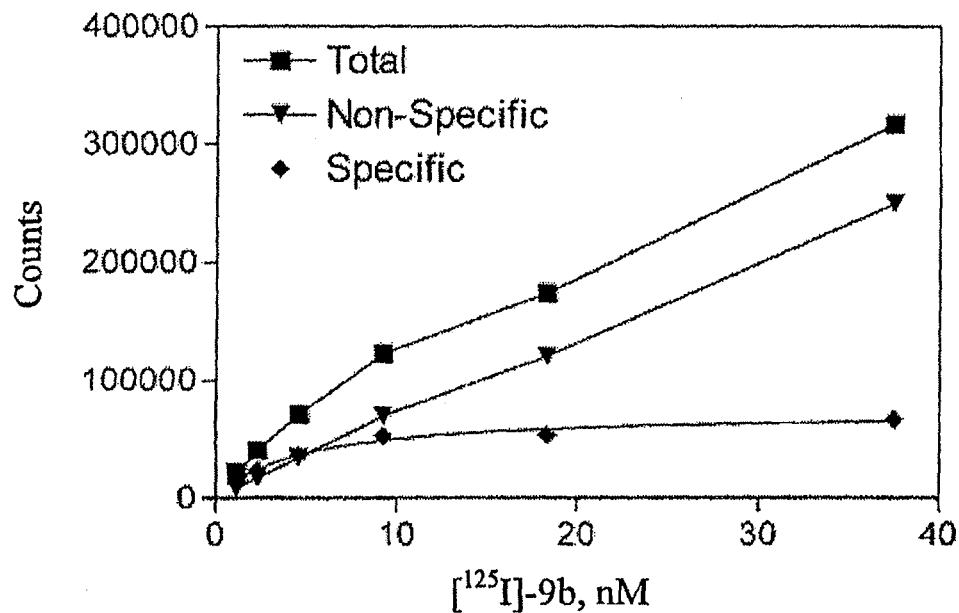
FIG. 7A depicts the non-specific, specific, and total binding of $[^{125}I]$ 7b on mouse $A_3$ adenosine receptor.
Figure 7B:
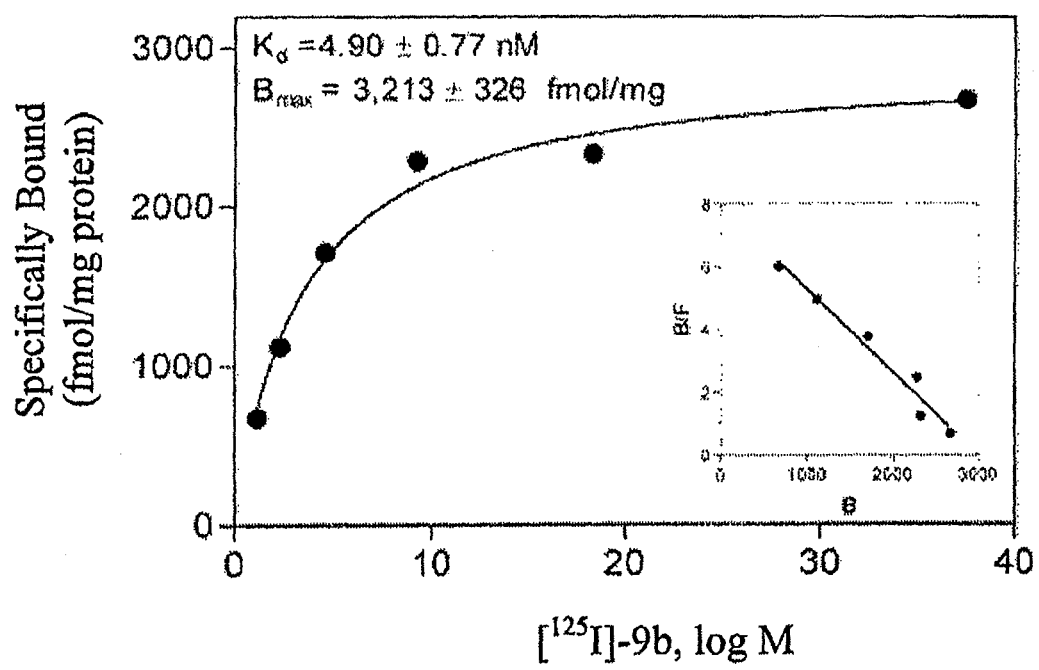
FIG. 7B depicts the extent of specific binding as a function of the concentration of the compound.

FIG. 7A depicts the non-specific, specific, and total binding of [$^{125}$I] 7b on mouse $A_3$ adenosine receptor. FIG. 7B depicts the extent of specific binding as a function of the concentration of the compound. The compound was an agonist of the mouse $A_3$ adenosine receptor.

EXAMPLE 4

This example illustrates a method of preparing a radiolabeled ligand, that is $^{76}$Br-labeled compound 9b in accordance with an embodiment of the invention. Bromine-76 was prepared from an arsenic metal target using the $^{75}$As ($^3$He, 2n) yielding $^{76}$Br nuclear reaction. The $^{76}$Br was processed after allowing for the decay of the simultaneously produced Br-75 ($t_{1/2}$=1.6 h).

An aliquot of the aqueous solution of Br-76 (about 10-20 μl, 18.5-37.0 MBq) is added to a 1-mL reaction vial and the solvent evaporated with argon flow. Trimethylstannyl intermediate 23 in acetonitrile is added to the vial containing the Br-76 radioactivity and followed by adding 37% peracetic acid in acetonitrile. The vial is sealed and placed on an 80° C. heating block and heated for 30 min. At the end of the reaction, the reaction mixture is loaded onto a Phenomenex Luna C18 (2) column (250×4.6 mm) and eluted with 100 mM ammonium acetate/acetonitrile (60/40) at a flow rate of 1.2 mL/min. The radioactivity peak containing the desired product ($t_R$=10 min) is collected and analyzed on a separate HPLC system for determination of purity and specific activity.

Figure 8:
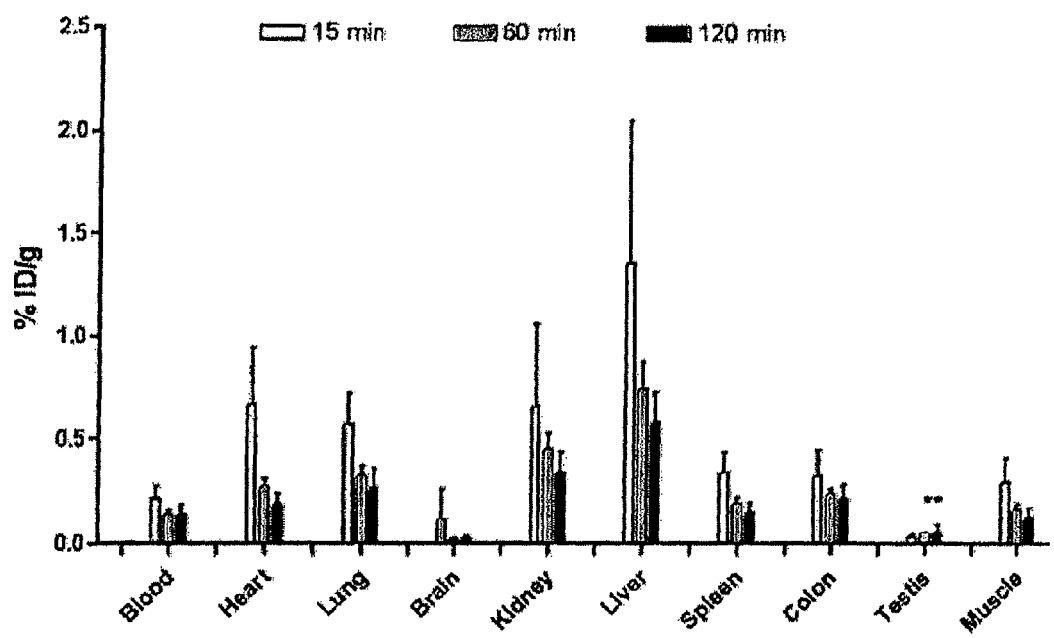
FIG. 8 depicts the biodistribution of Br-76 labeled compound 9b at 15, 60, and 120 min post injection in rats. The Y-axis represents % Initial Dose per gram and X-axis shows various organs.

In vivo biodistribution of compound Br-76 labeled compound 9b was carried out in rats. All studies in live animals were conducted under protocol approved by the NIH Animal Care and Use Committee. The biodistribution was evaluated after intravenous administration to adult Sprague-Dawley rats. The animals were sacrificed at 15, 30, 60, and 120 min and various tissues were harvested for gamma counting. The data are reported in units of percentage of injected dose per gram in FIG. 8. The compound exhibited antagonistic properties to the $A_3$ adenosine receptor albeit at a low magnitude of uptake. The low uptake may be due to the lower age of the animals. The uptake in the $A_3$AR-containing testes continued to increase with time after injection (0.09% ID/g at 15 min to 0.18% ID/g at 2 h). Blood continued to provide an input function over 2 h. In spite of a potential testes-blood barrier, uptake of the antagonist increased with time, which indicates that the compound may be a viable molecular imaging probe for pathological conditions with elevated $A_3$AR.

EXAMPLE 5

Figure 9:
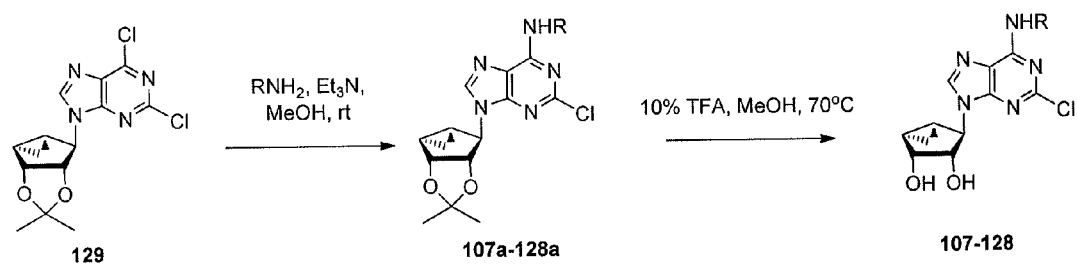
FIG. 9 depicts a reaction scheme to prepare compounds in accordance with an embodiment of the invention.
Figure 10:
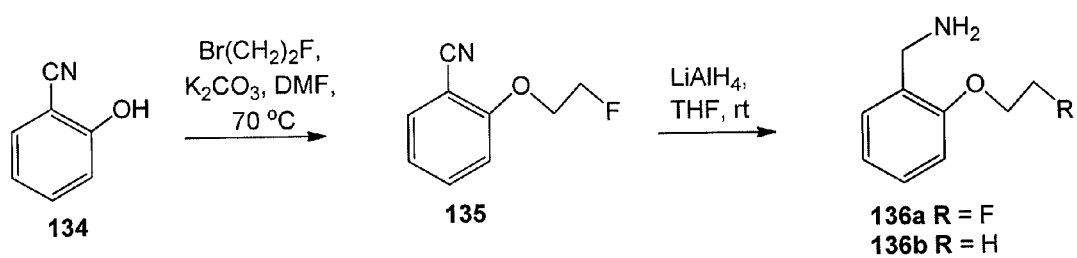
FIG. 10 depicts a reaction scheme to prepare intermediates needed for preparing compounds 136a and 136b.

This Example illustrates a method of preparing compounds in accordance with another embodiment of the invention. See also FIG. 9-10.

Materials and Instrumentation

Synthetic reagents and solvents were purchased from Sigma-Aldrich (St. Louis, Mo.). $^1$H NMR spectra were obtained with a Bruker 400 spectrometer. When using $D_2O$ was used as a solvent, the chemical shifts are expressed as relative ppm from HOD (4.80 ppm).

The purity of the final nucleotide derivatives were determined using a Hewlett-Packard 1100 HPLC equipped with a Zorbax Eclipse 5 mm XDB-C18 analytical column (250×4.6 mm; Agilent Technologies Inc, Palo Alto, Calif.), using a linear gradient solvent system: 5 mM TBAP (tetrabutylammonium dihydrogenphosphate)-$CH_3CN$ from 80:20 to 40:60 in 20 min with a flow rate of 1 mL/min. Peaks were detected by UV absorption (254 nm) using a diode array detector. All derivatives tested for biological activity were shown to be at least 97% pure using this analytical HPLC system.

High-resolution mass measurements were performed on a Micromass/Waters LCT Premier Electrospray Time of Flight (TOF) mass spectrometer coupled with a Waters HPLC system. Unless noted otherwise, reagents and solvents were purchased from Sigma-Aldrich (St. Louis, Mo.). Solutions of the nucleoside analogues in DMSO (5 mM) were prepared for biological testing and stored at −20° C.

(1R,2R,3S,4R,5S)-4-(2-Chloro-6-(cyclopropylamino)-9H-purin-9-yl)-2',3'-O-(isopropylidene)-bicyclo[3.1.0]hexane (108a)

Cyclopropylamine (0.05 mL, 0.42 mmol) and triethylamine (0.16 mL, 1.1 mmol) was added to a solution of compound 129 (29.25 mg, 0.42 mmol) in methanol (1.5 mL) and stirred at room temperature for overnight. The reaction mixture was evaporated under vacuum and the residue was purified on flash column chromatography (hexane:ethyl acetate=1:1) to give the desired product 108a (26 mg, 86%) as a syrup. $^1$H NMR ($CDCl_3$, 400 MHz) δ 7.76 (s, 1H), 5.93 (br s, 1H), 5.36 (t, J=6.0 Hz, 1H), 4.99 (s, 1H), 4.65 (d, J=7.2 Hz, 1H), 3.14 (br s, 1H), 2.14-2.08 (m, 1H), 1.69-1.63 (m, 1H), 1.56 (s, 3H), 1.26 (s, 3H), 1.00-0.91 (m, 4H), 0.69-0.67 (m, 2H). HRMS calculated for $C_{17}H_{21}ClN_5O_2$ (M+H)$^+$: 362.1384. found 362.1375.

(1R,2R,3S,4R,5S)-4-(2-Chloro-6-(cyclobutylamino)-9H-purin-9-yl)-2',3'-O-(isopropylidene)-bicyclo[3.1.0]hexane (109a)

Compound 109a (82%) was prepared from compound 129 following the same method for compound 108a. $^1$H NMR ($CD_3OD$, 400 MHz) δ 8.13 (s, 1H), 5.37 (t, J=6.8 Hz, 1H), 4.96 (s, 1H), 4.70 (d, J=6.8 Hz, 1H), 2.45-2.43 (m, 2H), 2.12-2.03 (m, 3H, 1.84-1.82 (m, 2H), 1.74-1.70 (m, 1H), 1.51 (s, 3H), 1.25 (s, 3H), 0.95-0.90 (m, 2H). HRMS calculated for $C_{18}H_{23}ClN_5O_2$ (M+H)$^+$: 376.1540. found 376.1528.

(1R,2R,3S,4R,5S)-4-(2-Chloro-6-(cyclohexy-lamino)-9H-purin-9-yl)-2',3'-O-(isopropylidene)-bicyclo[3.1.0]hexane (110a)

Compound 110a (79%) was prepared from compound 129 following the same method for compound 108a. $^1$H NMR (CD$_3$OD, 400 MHz) δ 8.12 (s, 1H), 5.36 (t, J=6.0 Hz, 1H), 4.96 (s, 1H), 4.70 (d, J=6.8 Hz, 1H), 4.14-4.09 (m, 1H), 2.07-2.04 (m, 2H), 1.84-1.81 (m, 2H), 1.75-1.68 (m, 2H), 1.51 (s, 3H), 1.47-1.34 (m, 6H), 1.25 (s, 3H), 0.95-0.88 (m, 2H). HRMS calculated for C$_{20}$H$_{27}$ClN$_5$O$_2$ (M+H)$^+$: 404.1853. found 404.1842.

(1R,2R,3S,4R,5S)-4-(2-Chloro-6-(cyclohepty-lamino)-9H-purin-9-yl)-2',3'-O-(isopropylidene)-bicyclo[3.1.0]hexane (111a)

Compound 111a (88%) was prepared from compound 129 following the same method for compound 108a. $^1$H NMR (CD$_3$OD, 400 MHz) δ 8.13 (s, 1H), 5.36 (t, J=6.4 Hz, 1H), 4.96 (s, 1H), 4.70 (d, J=6.8 Hz, 1H), 4.31 (br s, 1H), 2.09-2.03 (m, 3H), 1.77-75 (m, 12H), 1.52 (s, 3H), 1.27 (s, 3H), 0.95-0.90 (m, 2H). HRMS calculated for C$_{21}$H$_{29}$ClN$_5$O$_3$ (M+H)$^+$: 418.2010. found 418.2017.

(1R,2R,3S,4R,5S)-4-(2-Chloro-6-(cyclooctylamino)-9H-purin-9-yl)-2',3'-O-(isopropylidene)-bicyclo[3.1.0]hexane (112a)

Compound 112a (85%) was prepared from compound 29 following the same method for compound 108a. $^1$H NMR (CD$_3$OD, 400 MHz) δ 8.13 (s, 1H), 5.36 (t, J=5.6 Hz, 1H), 4.96 (s, 1H), 4.70 (d, J=7.2 Hz, 1H), 4.36 (br s, 1H), 2.07-2.03 (m, 1H), 1.99-1.93 (m, 2H), 1.80-1.74 (m, 4H), 1.71-1.63 (m, 10H), 1.51 (s, 3H), 1.30 (s, 3H), 0.95-0.88 (m, 1H). HRMS calculated for C$_{22}$H$_{31}$ClN$_5$O$_2$ (M+H)$^+$: 432.2166. found 432.2168.

(1R,2R,3S,4R,5S)-4-(2-Chloro-6-(endo-norbornyl)-9H-purin-9-yl)-2',3'-O-(isopropylidene)-bicyclo[3.1.0]hexane (113a)

Compound 113a (92%) was prepared from compound 129 following the same method for compound 108a. $^1$H NMR (CD$_3$OD, 400 MHz) δ 8.16 (s, 1H), 5.36 (t, J=6.0 Hz, 1H), 4.97 (s, 1H), 4.70 (d, J=6.8 Hz, 1H), 4.42 (br s, 1H), 2.62 (br s, 1H), 2.29 (br s, 1H), 2.21-2.09 (m, 1H), 2.07-2.03 (m, 1H), 1.76-1.57 (m, 4H), 1.52 (s, 3H), 1.45-1.41 (m, 3H), 1.25 (s, 3H), 1.07-1.04 (m, 1H), 0.95-0.89 (m, 2H). HRMS calculated for C$_{21}$H$_{27}$ClN$_5$O$_2$ (M+H)$^+$: 416.1853. found 416.1837.

(1R,2R,3S,4R,5S)-4-(2-Chloro-6-(exo-norbornyl)-9H-purin-9-yl)-2',3'-O-(isopropylidene)-bicyclo[3.1.0]hexane (114a)

Compound 114a (89%) was prepared from compound 129 following the same method for compound 108a. $^1$H NMR (CD$_3$OD, 400 MHz) δ 8.13 (s, 1H), 5.36 (t, J=6.4 Hz, 1H), 4.97 (s, 1H), 4.70 (d, J=6.8 Hz, 1H), 4.03 (br s, 1H), 2.35 (br s, 2H), 2.09-2.03 (m, 1H), 1.93-1.87 (m, 1H), 1.75-1.70 (m, 1H), 1.61-1.59 (m, 2H), 1.52 (s, 3H), 1.48-1.27 (m, 4H), 1.25 (s, 3H), 0.95-0.89 (m, 2H). HRMS calculated for C$_{21}$H$_{27}$ClN$_5$O$_2$ (M+H)$^+$: 416.1853. found 416.1849.

(1R,2R,3S,4R,5S)-4-(2-Chloro-6-(ethylamino)-9H-purin-9-yl)-2',3'-O-(isopropylidene)-bicyclo[3.1.0]hexane (115a)

Compound 115a (78%) was prepared from compound 129 following the same method for compound 108a. $^1$H NMR (CD$_3$OD, 400 MHz) δ 8.12 (s, 1H), 5.36 (t, J=6.4 Hz, 1H), 4.96 (s, 1H), 4.70 (d, J=6.8 Hz, 1H), 3.6 (br s, 2H), 2.17-2.03 (m, 1H), 1.56-1.38 (m, 1H), 1.52 (s, 3H), 1.31-1.25 (m, 6H), 0.95-0.88 (m, 2H). HRMS calculated for C$_{15}$H$_{25}$ClN$_5$O$_2$ (M+H)$^+$: 350.1370. found 350.1377.

(1R,2R,3S,4R,5S)-4-(2-Chloro-6-(3-fluoropropy-lamino)-9H-purin-9-yl)-2',3'-O-(isopropylidene)-bicyclo[3.1.0]hexane (116a)

Compound 116a (80%) was prepared from compound 129 following the same method for compound 108a. $^1$H NMR (CD$_3$OD, 400 MHz) δ 8.12 (s, 1H), 5.38 (t, J=6.0 Hz, 1H), 4.97 (s, 1H), 4.71 (d, J=7.2 Hz, 1H), 4.65 (t, J=5.6 Hz, 1H), 4.52 (t, J=5.6 Hz, 1H), 3.70 (br s, 2H), 2.14-2.01 (m, 3H), 1.75-1.70 (m, 1H), 1.51 (s, 3H), 1.25 (s, 3H), 0.95-0.90 (m, 2H). HRMS calculated for C$_{17}$H$_{22}$ClN$_5$O$_2$ (M+H)$^+$: 382.1446. found 382.1442.

(1R,2R,3S,4R,5S)-4-(2-Chloro-6-(isopropylamino)-9H-purin-9-yl)-2',3'-O-(isopropylidene)-bicyclo[3.1.0]hexane (117a)

Compound 117a (75%) was prepared from compound 29 following the same method for compound 108a. $^1$H NMR (CDCl$_3$, 400 MHz) δ 7.74 (s, 1H), 5.37 (t, J=6.8 Hz, 1H), 4.98 (s, 1H), 4.65 (d, J=6.8 Hz, 1H), 2.13-2.08 (m, 1H), 1.69-1.64 (m, 1H), 2.13-2.08 (m, 1H), 1.69-1.64 (m, 1H), 1.60-1.59 (m, 4H), 1.33 (d, J=6.4 Hz, 6H), 1.26 (s, 3H), 1.01-0.90 (m, 1H). HRMS calculated for C$_{17}$H$_{23}$ClN$_5$O$_2$ (M+H)$^+$: 364.1540. found 364.1543.

(1R,2R,3S,4R,5S)-4-(2-Chloro-6-(pentan-3-ylamino)-9H-purin-9-yl)-2',3'-O-(isopropylidene)-bicyclo[3.1.0]hexane (118a)

Compound 118a (77%) was prepared from compound 129 following the same method for compound 108a. $^1$H NMR (CD$_3$OD, 400 MHz) δ 8.13 (s, 1H), 5.36 (t, J=6.0 Hz, 1H), 4.97 (s, 1H), 4.70 (d, J=6.8 Hz, 1H), 4.19 (br s, 1H), 2.09-2.03 (m, 1H), 1.75-1.70 (m, 2H), 1.62-1.55 (m, 2H), 1.52 (s, 3H), 1.27-1.25 (m, 4H), 0.99-0.95 (m, 8H). HRMS calculated for C$_{19}$H$_{27}$ClN$_5$O$_2$ (M+H)$^+$: 392.1853. found 392.1857.

(1R,2R,3S,4R,5S)-4-(2-Chloro-6-(cyclopropylm-ethylamino)-9H-purin-9-yl)-2',3'-O-(isopropy-lidene)-bicyclo[3.1.0]hexane (119a)

Compound 119a (83%) was prepared from compound 129 following the same method for compound 108a. $^1$H NMR (CD$_3$OD, 400 MHz) δ 8.13 (s, 1H), 5.38 (t, J=6.4 Hz, 1H), 4.97 (s, 1H), 4.71 (d, J=7.2 Hz, 1H), 3.42 (s, 2H), 2.09-2.03 (m, 1H), 1.75-1.71 (m, 1H), 1.52 (s, 3H), 1.25 (s, 3H), 1.21-1.14 (m, 1H), 0.96-0.89 (m, 2H), 0.59-0.54 (m, 2H), 0.36-0.33 (m, 2H). HRMS calculated for C$_{18}$H$_{23}$ClN$_5$O$_2$ (M+H)$^+$: 376.1540. found 376.1538.

(1R,2R,3S,4R,5S)-4-(2-Chloro-6-(1-cyclopropyl-ethylamino)-9H-purin-9-yl)-2',3'-O-(isopropy-lidene)-bicyclo[3.1.0]hexane (120a)

Compound 120a (85%) was prepared from compound 129 following the same method for compound 108a. $^1$H NMR (CD$_3$OD, 400 MHz) δ 8.13 (s, 1H), 5.36 (t, J=5.6 Hz, 1H), 4.96 (s, 1H), 4.70 (d, J=6.8 Hz, 1H), 3.24-3.18 (m, 1H), 2.07-2.04 (m, 2H), 1.74-1.72 (m, 1H), 1.52 (s, 3H), 1.37 (d, J=6.8, 3H), 1.27 (s, 3H), 1.06-1.04 (m, 1H), 0.95-0.90 (m, 2H), 0.57-0.44 (m, 3H), 0.33-0.31 (m, 1H). HRMS calculated for $C_{19}H_{25}ClN_5O_2$ (M+H)$^+$: 390.1697. found 390.1703.

(1R,2R,3S,4R,5S)-4-(2-Chloro-6-(dicyclopropylmethylamino)-9H-purin-9-yl)-2',3'-O-(isopropylidene)-bicyclo[3.1.0]hexane (121a)

Compound 121a (86%) was prepared from compound 129 following the same method for compound 108a. $^1$H NMR (CD$_3$OD, 400 MHz) δ 8.13 (s, 1H), 5.36 (t, J=6.0 Hz, 1H), 4.96 (s, 1H), 4.70 (d, J=6.8 Hz, 1H), 3.48 (br s, 1H), 2.08-2.03 (m, 1H), 1.75-1.71 (m, 1H), 1.51 (s, 3H), 1.25 (s, 3H), 1.16-1.11 (m, 2H), 0.95-0.90 (m, 2H), 0.60-0.58 (m, 2H), 0.46-0.41 (m, 6H). HRMS calculated for $C_{21}H_{27}ClN_5O_2$ (M+H)$^+$: 416.1840. found 416.1839.

(1R,2R,3S,4R,5S)-4-(2-Chloro-6-(2-(2-fluoroethoxy)benzylamino)-9H-purin-9-yl)-2',3'-O-(isopropylidene)-bicyclo[3.1.0]hexane (123a)

Triethylamine (0.08 mL, 0.6 mmol) and 2-fluoroethoxy-benzylamine (0.01 mL, 0.105 mmol) was added to a solution of compound 129 (15 mg, 0.043 mmol) in anhydrous methanol (1.5 mL) and stirred for overnight at room temperature. Solvent was evaporated and the residue was purified on flash silica gel column chromatography (hexane:ethyl acetate=2:1) to give the fluoro reduced product 128a (7 mg, 35%) and further elution with same solvent gave the desired compound 123a (11 mg, 52%) as a syrup. Data for compound 123a: $^1$H NMR (CD$_3$OD, 300 MHz) δ 8.10 (s, 1H), 7.35 (d, J=9.0 Hz, 1H), 7.22-7.28 (m, 1H), 6.98 (d, J=8.1 Hz, 1H), 6.91 (t, J=7.5 Hz, 1H), 5.34 (t, J=5.1 Hz, 1H), 4.95 (s, 1H), 4.79-4.82 (m, 2H), 4.68 (d, J=6.9 Hz, 2H), 4.32 (t, J=3.9 Hz, 1H), 4.23 (t, J=4.2 Hz, 1H), 2.01-2.06 (m, 1H), 1.69-1.72 (m, 1H), 1.49 (s, 3H), 1.23 (s, 3H), 0.87-0.93 (m, 2H). HRMS calculated for $C_{23}H_{26}ClFN_5O_3$ (M+H)$^+$: 474.1708. found 474.1696.

Data for compound 128a: $^1$H NMR (CD$_3$OD, 300 MHz) δ 8.11 (s, 1H), 7.33 (d, J=7.5 Hz, 1H), 7.21 (t, J=6.6 Hz, 1H), 6.95 (d, J=8.1 Hz, 1H), 6.87 (t, J=6.9 Hz, 1H), 5.34 (t, J=5.4 Hz, 1H), 4.95 (s, 1H), 4.76 (s, 2H), 4.68 (d, J=7.2 Hz, 1H), 4.10 (q, J$_1$=6.9 Hz, J$_2$=7.2 Hz, 2H), 2.01-2.06 (m, 1H), 1.68-1.72 (m, 1H), 1.50 (s, 3H), 1.39 (t, J=6.9 Hz, 3H), 1.23 (s, 3H), 0.87-0.93 (m, 2H). HRMS calculated for $C_{23}H_{27}ClN_5O_3$ (M+H)$^+$: 456.1802. found 456.1827.

(1R,2R,3S,4R,5S)-4-(2-Chloro-6-(3-(2-fluoroethoxy)benzylamino)-9H-purin-9-yl)-2',3'-O-(isopropylidene)-bicyclo[3.1.0]hexane (124a)

Compound 124a (84%) was prepared from compound 129 following the same method for compound 23a. $^1$H NMR (CD$_3$OD, 400 MHz) δ 8.11 (s, 1H), 7.26 (t, J=8.0 Hz, 1H), 6.99-7.02 (m, 2H), 6.84-6.86 (m, 1H), 5.35 (t, J=6.8 Hz, 1H), 4.96 (s, 1H), 4.77-4.74 (m, 3H), 4.69-4.71 (m, 1H), 4.63-4.65 (m, 1H), 4.23 (t, J=4.4 Hz, 1H), 4.17 (t, J=5.2 Hz, 1H), 2.08-2.04 (m, 1H), 1.75-1.70 (m, 1H), 1.51 (s, 3H), 1.24 (s, 3H), 0.95-0.87 (m, 2H). HRMS calculated for $C_{23}H_{26}ClFN_5O_3$ (M+H)$^+$: 474.1708. found 474.1716.

(1R,2R,3S,4R,5S)-4-(2-Chloro-6-(2,5-difluorobenzylamino)-9H-purin-9-yl)-2',3'-O-(isopropylidene)-bicyclo[3.1.0]hexane (125a)

Compound 125a (79%) was prepared from compound 129 following the same method for compound 108a. $^1$H NMR (CDCl$_3$, 300 MHz) δ 7.76 (s, 1H), 6.93-7.24 (m, 3H), 6.20 (br s, 1H), 5.35 (t, J=5.1 Hz, 1H), 4.87-4.98 (m, 3H), 4.64 (d, J=6.6 Hz, 1H), 2.05-2.16 (m, 1H), 1.61-1.71 (m, 1H), 1.54 (s, 3H), 1.25 (s, 3H), 0.89-0.98 (m, 2H). HRMS calculated for $C_{21}H_{21}ClF_2N_5O_2$ (M+H)$^+$: 448.1352. found 448.1339.

(1R,2R,3S,4R,5S)-4-(2-Chloro-6-(2,3-difluoro-6-methoxybenzylamino)-9H-purin-9-yl)-2',3'-O-(isopropylidene)-bicyclo[3.1.0]hexane (126a)

Compound 126a (77%) was prepared from compound 29 following the same method for compound 108a. $^1$H NMR (CD$_3$OD, 300 MHz) δ 8.14 (s, 1H), 7.14-7.24 (m, 1H), 6.78-6.83 (m, 1H), 5.36 (t, J=5.4 Hz, 1H), 4.97 (s, 1H), 4.81-4.83 (m, 2H), 4.69 (d, J=7.2 Hz, 1H), 3.89 (s, 3H), 2.02-2.08 (m, 1H), 1.69-1.74 (m, 1H), 1.51 (s, 3H), 1.25 (s, 3H), 0.87-0.95 (m, 2H). HRMS calculated for $C_{22}H_{23}ClF_2N_5O_3$ (M+H)$^+$: 478.1457. found 478.1469.

(1R,2R,3S,4R,5S)-4-(2-Chloro-6-(4,5-difluoro-2-methoxybenzylamino)-9H-purin-9-yl)-2',3'-O-(isopropylidene)-bicyclo[3.1.0]hexane (127a)

Compound 127a (71%) was prepared from compound 129 following the same method for compound 108a. $^1$H NMR (CD$_3$OD, 300 MHz) δ 8.14 (s, 1H), 7.22-7.29 (m, 1H), 6.93-6.99 (m, 1H), 5.36 (t, J=5.7 Hz, 1H), 4.97 (s, 1H), 4.69-4.71 (m, 3H), 3.89 (s, 3H), 2.02-2.08 (m, 1H), 1.72-1.74 (m, 1H), 1.51 (s, 3H), 1.25 (s, 3H), 0.89-0.95 (m, 2H). HRMS calculated for $C_{22}H_{23}ClF_2N_5O_3$ (M+H)$^+$: 478.1457. found 478.1449.

(1R,2R,3S,4R,5S)-4-(6-Amino-2-chloro-9H-purin-9-yl)-bicyclo[3.1.0]hexane-2,3-diol (107)

10% Trifluoroacetic acid (2 mL) was added to a solution of compound 121a (25 mg, 0.06 mmol) in methanol (2 mL) and heated at 70° C. for 6 h. The reaction mixture was evaporated and the residue was purified on flash silica gel column chromatography to give the compound 107 (12 mg, 71%) as syrup instead of giving the desired product 121. $^1$H NMR (CD$_3$OD, 400 MHz) δ 8.20 (s, 1H), 4.80 (s, 1H), 4.72 (t, J=6.4 Hz, 1H), 3.91 (d, J=6.4 Hz, 1H), 2.02-1.97 (m, 1H), 1.70-1.66 (m, 1H), 1.34-1.31 (m, 1H), 0.80-0.75 (m, 1H). HRMS calculated for $C_{11}H_{13}ClN_5O_2$ (M+H)$^+$: 282.0758. found 282.0758.

(1R,2R,3S,4R,5S)-4-(2-Chloro-6-(cyclopropylamino)-9H-purin-9-yl)bicyclo[3.1.0]hexane-2,3-diol (108)

Dowex 50 resin (20 mg) was added to a solution of compound 108a (10 mg, 0.03 mmol) in methanol (0.5 mL) and water (0.5 mL) and stirred at room temperature for overnight. After completion of reaction, the reaction mixture was filtered on a celite bed and filtrate was evaporated under vacuum and the residue was purified on flash silica gel column chromatography to give the desired compound 108 (7.1 mg, 80%) as a syrup. $^1$H NMR (CD$_3$OD, 400 MHz) δ 8.14 (s, 1H), 4.80 (s, 1H), 4.71 (t, J=6.0 Hz, 1H), 3.90 (d, J=6.4 Hz, 1H), 2.00-1.97 (m, 1H), 1.69-1.64 (m, 1H), 1.34-1.30 (m, 4H), 0.90-0.89 (m, 1H), 0.80-0.74 (m, 1H), 0.67-0.63 (m, 2H). HRMS calculated for $C_{14}H_{17}ClN_5O_2$ (M+H)$^+$: 322.1071. found 322.1067.

(1R,2R,3S,4R,5S)-4-(2-Chloro-6-(cyclobutylamino)-9H-purin-9-yl)bicyclo[3.1.0]hexane-2,3-diol (109)

A solution of compound 109a (20 mg, 0.053 mmol) in methanol (1 mL) and 10% trifluoroacetic acid (1 mL) was heated at 70° C. for 6 h. Solvent was evaporated and the residue was purified on flash silica gel column chromatography (hexane: ethyl acetate=1:1) to yield compound 109 (15 mg, 87%). $^1$H NMR (CD$_3$OD, 400 MHz) δ 8.14 (s, 1H), 4.79 (s, 1H), 4.72 (t, J=5.6 Hz, 1H), 3.89 (d, J=6.4 Hz, 1H), 2.45-2.40 (m, 2H), 2.12-2.05 (m, 2H), 2.01-1.95 (m, 1H), 1.84-1.82 (m, 2H), 1.69-1.64 (m, 1H), 1.34-1.27 (m, 2H), 0.79-0.74 (m, 1H). HRMS calculated for C$_{15}$H$_{19}$ClN$_5$O$_2$ (M+H)$^+$: 336.1227. found 336.1216.

(1R,2R,3S,4R,5S)-4-(2-Chloro-6-(cyclohexylamino)-9H-purin-9-yl)bicyclo[3.1.0]hexane-2,3-diol (110)

Compound 110 (84%) was prepared from compound 110a following the same method for compound 109. $^1$H NMR (CD$_3$OD, 400 MHz) δ 8.14 (s, 1H), 4.79 (s, 1H), 4.70 (t, J=5.6 Hz, 1H), 4.12 (br s, 1H), 3.89 (d, J=6.4 Hz, 1H), 2.05-1.96 (m, 2H), 1.84-1.81 (m, 2H), 1.68-1.67 (m, 2H), 1.50-1.25 (m, 7H), 0.79-0.74 (m, 1H). HRMS calculated for C$_{17}$H$_{23}$ClN$_5$O$_2$ (M+H)$^+$: 364.1540. found 364.1534.

(1R,2R,3S,4R,5S)-4-(2-Chloro-6-(cycloheptylamino)-9H-purin-9-yl)bicyclo[3.1.0]hexane-2,3-diol (111)

Compound 111 (79%) was prepared from compound 111a following the same method for compound 109. $^1$H NMR (CD$_3$OD, 400 MHz) δ 8.14 (s, 1H), 4.79 (s, 1H), 4.70 (t, J=5.6 Hz, 1H), 4.31 (br s, 1H), 3.88 (d, J=6.8 Hz, 1H), 2.07-1.96 (m, 2H), 1.71-1.64 (m, 12H), 1.34-1.31 (m, 1H), 0.79-0.74 (m, 1H). HRMS calculated for C$_{18}$H$_{25}$ClN$_5$O$_2$ (M+H)$^+$: 378.1697. found 378.1690.

(1R,2R,3S,4R,5S)-4-(2-Chloro-6-(cyclooctylamino)-9H-purin-9-yl)bicyclo[3.1.0]hexane-2,3-diol (112)

Compound 112 (75%) was prepared from compound 112a following the same method for compound 109. $^1$H NMR (CD$_3$OD, 400 MHz) δ 8.15 (s, 1H), 4.79 (s, 1H), 4.72 (t, J=5.6 Hz, 1H), 4.36 (br s, 1H), 3.89 (d, J=6.8 Hz, 1H), 2.00-1.93 (m, 3H), 1.80-1.78 (m, 4H), 1.67-1.65 (m, 9H), 1.34-1.32 (m, 1H), 0.79-0.74 (m, 1H). HRMS calculated for C$_{19}$H$_{27}$ClN$_5$O$_2$ (M+H)$^+$: 392.1853. found 392.1851.

(1R,2R,3S,4R,5S)-4-(2-Chloro-6-(endo-norbornyl)-9H-purin-9-yl)bicyclo[3.1.0]hexane-2,3-diol (113)

Compound 113 (85%) was prepared from compound 113a following the same method for compound 109. $^1$H NMR (CD$_3$OD, 400 MHz) δ 8.18 (s, 1H), 4.80 (s, 1H), 4.72 (t, J=6.0 Hz, 1H), 4.40 (br s, 1H), 3.90 (d, J=6.2 Hz, 1H), 2.62 (br s, 1H), 2.29 (br s, 1H), 2.21-2.15 (m, 1H), 1.99-1.97 (m, 1H), 1.76-1.57 (m, 4H), 1.45-1.41 (m, 2H), 1.34-1.32 (m, 2H), 1.07-1.04 (m, 1H), 0.80-0.76 (m, 1H). HRMS calculated for C$_{18}$H$_{23}$ClN$_5$O$_2$ (M+H)$^+$: 376.1540. found 376.1545.

(1R,2R,3S,4R,5S)-4-(2-Chloro-6-(exo-norbornyl)-9H-purin-9-yl)bicyclo[3.1.0]hexane-2,3-diol (114)

Compound 114 (89%) was prepared from compound 114a following the same method for compound 109. $^1$H NMR (CD$_3$OD, 400 MHz) δ 8.1.5 (s, 1H), 4.79 (s, 1H), 4.72 (t, J=5.2 Hz, 1H), 4.02 (br s, 1H), 3.90 (d, J=6.4 Hz, 1H), 2.34 (br s, 2H), 2.01-1.87 (m, 2H), 1.69-1.55 (m, 4H), 1.47-1.21 (m, 5H), 0.79-0.74 (m, 1H). HRMS calculated for C$_{18}$H$_{23}$ClN$_5$O$_2$ (M+H)$^+$: 376.1540. found 376.1534.

(1R,2R,3S,4R,5S)-4-(2-Chloro-6-(ethylamino)-9H-purin-9-yl)bicyclo[3.1.0]hexane-2,3-diol (115)

Compound 115 (76%) was prepared from compound 115a following the same method for compound 109. $^1$H NMR (CD$_3$OD, 400 MHz) δ 8.13 (s, 1H), 4.79 (s, 1H), 4.74 (t, J=5.6 Hz, 1H), 3.90 (d, J=6.4 Hz, 1H), 3.61 (br s, 2H), 2.01-1.96 (m, 1H), 1.69-1.64 (m, 1H), 1.34-1.28 (m, 4H), 0.79-0.74 (m, 1H). HRMS calculated for C$_{13}$H$_{17}$ClN$_5$O$_2$ (M+H)$^+$: 310.1071. found 310.1080.

(1R,2R,3S,4R,5S)-4-(2-Chloro-6-(3-fluoropropylamino)-9H-purin-9-yl)bicyclo[3.1.0]hexane-2,3-diol (116)

Compound 116 (77%) was prepared from compound 116a following the same method for compound 109. $^1$H NMR (CD$_3$OD, 400 MHz) δ 8.14 (s, 1H), 4.80 (s, 1H), 4.71 (t, J=5.6 Hz, 1H), 4.63 (t, J=6.0 Hz, 1H), 4.53 (t, J=6.0 Hz, 1H), 3.90 (d, J=6.4 Hz, 1H), 3.70 (br s, 2H), 2.14-1.96 (m, 3H), 1.69-1.65 (m, 1H), 1.34-1.31 (m, 1H), 0.80-0.74 (m, 1H). HRMS calculated for C$_{14}$H$_{18}$ClFN$_5$O$_2$ (M+H)$^+$: 342.1133. found 342.1137.

(1R,2R,3S,4R,5S)-4-(2-Chloro-6-(isopropylamino)-9H-purin-9-yl)bicyclo[3.1.0]hexane-2,3-diol (117) MRS5464

Compound 117 (75%) was prepared from compound 111a following the same method for compound 109. $^1$H NMR (CD$_3$OD, 400 MHz) δ 8.14 (s, 1H), 4.79 (s, 1H), 4.71 (t, J=6.0 Hz, 1H), 3.90 (d, J=6.2 Hz, 1H), 2.01-1.95 (m, 1H), 1.69-1.65 (m, 1H), 1.32-1.30 (m, 8H), 0.79-0.74 (m, 1H). HRMS calculated for C$_{14}$H$_{19}$ClN$_5$O$_2$ (M+H)$^+$: 324.1227. found 324.1226.

(1R,2R,3S,4R,5S)-4-(2-Chloro-6-(pentan-3-ylamino)-9H-purin-9-yl)bicyclo[3.1.0]hexane-2,3-diol (118)

Compound 118 (76%) was prepared from compound 118a following the same method for compound 109. $^1$H NMR (CD$_3$OD, 400 MHz) δ 8.15 (s, 1H), 4.79 (s, 1H), 4.71 (t, J=5.6 Hz, 1H), 4.19 (s, 1H), 3.91 (d, J=6.4 Hz, 1H), 2.02-1.96 (m, 1H), 1.75-1.65 (m, 2H), 1.62-1.55 (m, 2H), 1.34-1.30 (m, 2H), 0.97 (t, J=7.2 Hz, 6H), 0.80-0.74 (m, 1H). HRMS calculated for C$_{16}$H$_{23}$ClN$_5$O$_2$ (M+H)$^+$: 352.1540. found 352.1541.

(1R,2R,3S,4R,5S)-4-(2-Chloro-6-(cyclopropylmethylamino)-9H-purin-9-yl)bicyclo[3.1.0]hexane-2,3-diol (119)

Compound 119 (85%) was prepared from compound 119a following the same method for compound 108. $^1$H NMR (CD$_3$OD, 400 MHz) δ 8.15 (s, 1H), 4.80 (s, 1H), 4.72 (t, J=5.6 Hz, 1H), 3.90 (d, J=6.8 Hz, 1H), 3.44 (br s, 2H), 2.01-1.96 (m, 1H), 1.69-1.65 (m, 1H), 1.34-1.30 (m, 1H), 1.20-1.14 (m, 1H), 0.80-0.74 (m, 1H), 0.58-0.55 (m, 2H), 0.35-0.34 (m, 2H). HRMS calculated for C$_{15}$H$_{19}$ClN$_5$O$_2$ (M+H)$^+$: 336.1227. found 336.1236.

(1R,2R,3S,4R,5S)-4-(2-Chloro-6-(1-cyclopropylethylamino)-9H-purin-9-yl)bicyclo[3.1.0]hexane-2,3-diol (120)

Compound 120 (79%) was prepared from compound 120a following the same method for compound 108. $^1$H NMR (CD$_3$OD, 400 MHz) δ 8.14 (s, 1H), 4.79 (s, 1H), 4.71 (t, J=5.6 Hz, 1H), 3.90 (d, J=6.4 Hz, 1H), 2.00-1.97 (m, 1H), 1.69-1.65 (m, 1H), 1.38 (d, J=6.4 Hz, 3H), 1.23-1.19 (m, 1H), 1.08-1.02 (m, 1H), 0.93-0.90 (m, 1H), 0.79-0.74 (m, 1H), 0.59-0.43 (m, 3H), 0.34-0.30 (m, 1H). HRMS calculated for C$_{16}$H$_{21}$ClN$_5$O$_2$ (M+H)$^+$: 350.1384. found 350.1378.

(1R,2R,3S,4R,5S)-4-(2-Chloro-6-(dicyclopropylmethylamino)-9H-purin-9-yl)bicyclo[3.1.0]hexane-2,3-diol (121)

Compound 121 (81%) was prepared from compound 121a following the same method for compound 108. $^1$H NMR (CD$_3$OD, 400 MHz) δ 8.15 (s, 1H), 4.79 (s, 1H), 4.71 (t, J=5.6 Hz, 1H), 3.90 (d, J=6.8 Hz, 1H), 3.48 (br s, 1H), 2.01-1.96 (m, 1H), 1.69-1.65 (m, 1H), 1.34-1.31 (m, 2H), 1.18-1.09 (m, 2H), 0.79-0.74 (m, 1H), 0.59-0.55 (m, 2H), 0.47-0.41 (m, 6H). HRMS calculated for C$_{18}$H$_{23}$ClN$_5$O$_2$ (M+H)$^+$: 376.1540. found 376.1539.

(1R,2R,3S,4R,5S)-4-(2-Chloro-6-(2-fluorobenzylamino)-9H-purin-9-yl)bicyclo[3.1.0]hexane-2,3-diol (122)

2-Fluoro-benzyl amine (0.04 mL, 0.34 mmol) and triethylamine (0.13 mL, 0.84 mmol) was added to a solution of compound 129 (23.2 mg, 0.06 mmol) in methanol (1.5 mL) and stirred at room temperature for overnight. The reaction mixture was evaporated under vacuum and the residue was roughly purified on flash column chromatography. The product was dissolved in methanol (2 mL) and 10% trifluoroacetic acid (2 mL) and heated at 70° C. for 6 h. The reaction mixture was evaporated under vacuum and the residue was purified on flash silica gel column chromatography (hexane:ethyl acetate=1:1) to give the desired compound 122 (19 mg, 75%) as a syrup. $^1$H NMR (CD$_3$OD, 400 MHz) δ 8.16 (s, 1H), 7.47 (t, J=8.0 Hz, 1H), 7.29-7.34 (m, 1H), 7.09-7.16 (m, 2H), 4.83 (br s, 2H), 4.80 (s, 1H), 4.71 (t, J=5.6 Hz, 1H), 1.97-1.99 (m, 1H), 1.63-1.72 (m, 1H), 0.90-0.91 (m, 1H), 0.74-0.79 (m, 1H). HRMS calculated for C$_{18}$H$_{18}$ClFN$_5$O$_2$ (M+H)$^+$: 390.1133. found 390.1145.

(1R,2R,3S,4R,5S)-4-(2-chloro-6-(2-(2-fluoroethoxy)benzylamino)-9H-purin-9-yl)bicyclo[3.1.0]hexane-2,3-diol (123)

Compound 123 (87%) was prepared from compound 123a following the same method for compound 109. $^1$H NMR (CD$_3$OD, 300 MHz) δ 8.12 (s, 1H), 7.35 (d, J=7.8 Hz, 1H), 7.26 (t, J=7.8 Hz, 1H), 6.93-7.00 (m, 2H), 4.79 (s, 2H), 4.64-4.68 (m, 1H), 4.31-4.33 (m, 1H), 4.22-4.24 (m, 1H), 3.87 (d, J=6.6 Hz, 1H), 1.90-2.05 (m, 1H), 1.61-1.72 (m, 1H), 1.23-1.38 (m, 1H), 0.72-0.81 (m, 1H). HRMS calculated for C$_{20}$H$_{22}$ClFN$_5$O$_3$ (M+H)$^+$: 434.1395; found 434.1385.

(1R,2R,3S,4R,5S)-4-(2-chloro-6-(3-(2-fluoroethoxy)benzylamino)-9H-purin-9-yl)bicyclo[3.1.0]hexane-2,3-diol (124)

Compound 124 (91%) was prepared from compound 124a following the same method for compound 109. $^1$H NMR (CD$_3$OD, 400 MHz) δ 8.03 (s, 1H), 7.21 (t, J=8.0 Hz, 1H), 6.98 (m, 2H), 6.83 (d, J=6.4 Hz, 1H), 4.72-4.74 (m, 4H), 4.67 (t, J=6.0 Hz, 1H), 4.63 (t, J=4.0 Hz, 1H), 4.21 (t, J=4.0 Hz, 1H), 4.13 (t, J=4.0 Hz, 1H), 3.89 (d, J=6.4 Hz, 1H), 1.99-1.93 (m, 1H), 1.66-1.62 (m, 1H), 1.32-1.29 (m, 1H), 0.77-0.72 (m, 1H). HRMS calculated for C$_{20}$H$_{22}$ClFN$_5$O$_3$ (M+H)$^+$: 434.1395. found 434.1399.

(1R,2R,3S,4R,5S)-4-(2-chloro-6-(2,5-difluorobenzylamino)-9H-purin-9-yl)bicyclo[3.1.0]hexane-2,3-diol (125) MRS5227

Compound 125 (81%) was prepared from compound 125a following the same method for compound 109. $^1$H NMR (CD$_3$OD, 300 MHz) δ 8.17 (s, 1H), 6.99-7.22 (m, 3H), 4.81-4.85 (m, 3H), 4.72 (t, J=5.1 Hz, 1H), 3.91 (d, J=6.6 Hz, 1H), 1.95-2.02 (m, 1H), 1.65-1.70 (m, 1H), 1.30-1.34 (m, 1H), 0.73-0.80 (m, 1H). HRMS calculated for C$_{18}$H$_{17}$ClF$_2$N$_5$O$_2$ (M+H)$^+$: 408.1039. found 408.1017.

(1R,2R,3S,4R,5S)-4-(2-chloro-6-(2,3-difluoro-6-methoxybenzylamino)-9H-purin-9-yl)bicyclo[3.1.0]hexane-2,3-diol (126) MRS5230

Compound 126 (86%) was prepared from compound 126a following the same method for compound 109. $^1$H NMR (CD$_3$OD, 300 MHz) δ 8.15 (s, 1H), 7.14-7.23 (m, 1H), 6.77-6.81 (m, 1H), 4.79-4.86 (m, 3H), 4.70 (t, J=5.1 Hz, 1H), 3.89 (s, 4H), 1.94-2.00 (m, 1H), 1.63-1.69 (m, 1H), 1.28-1.34 (m, 1H), 0.72-0.80 (m, 1H). HRMS calculated for C$_{19}$H$_{19}$ClF$_2$N$_5$O$_3$ (M+H)$^+$: 438.1144. found 438.1138.

(1R,2R,3S,4R,5S)-4-(2-chloro-6-(4,5-difluoro-2-methoxybenzylamino)-9H-purin-9-yl)bicyclo[3.1.0]hexane-2,3-diol (127) MRS5231

Compound 127 (77%) was prepared from compound 127a following the same method for compound 109. $^1$H NMR (CD$_3$OD, 300 MHz) δ 8.15 (s, 1H), 7.21 (m, 1H), 6.91-6.97 (m, 1H), 4.79 (s, 1H), 4.68-4.72 (m, 3H), 3.98 (s, 4H), 1.94-2.02 (m, 1H), 1.64-1.69 (m, 1H), 1.29-1.34 (m, 1H), 0.72-0.80 (m, 1H). HRMS calculated for C$_{19}$H$_{19}$ClF$_2$N$_5$O$_3$ (M+H)$^+$: 438.1144. found 438.1143.

2-(2-Fluoroethoxy)benzonitrile (135)

K$_2$CO$_3$ (1.74 g, 12.5 mmol) and 1-bromo-2-fluoro ethane (0.78 mL, 10.47 mmol) were added to a solution of 2-cyanophenol 134 (0.5 g, 4.19 mmol) in anhydrous DMF (10 mL), and heated at 70° C. for 45 min. After completion, the reaction mixture was cooled to room temperature and water (10 mL) was added and the mixture extracted with diethyl ether. The combined organic layer was washed with brine, dried (Na$_2$SO$_4$), filtered and evaporated. The residue was purified on flash silica gel column chromatography (hexane:ethyl acetate=2:1) to give the compound 135 (0.586 g, 84%) as a white solid. $^1$H NMR (CDCl$_3$, 300 MHz) d 7.51-7.58 (m, 2H), 6.98-7.07 (m, 2H), 4.89 (t, J=3.9 Hz, 1H), 4.73 (t, J=4.2 Hz, 1H), 4.40 (t, J=3.9 Hz, 1H), 4.31 (t, J=3.9 Hz, 1H). HRMS calculated for C$_8$H$_7$NOF (M+H)$^+$: 152.0513. found 152.0539.

(2-(2-Fluoroethoxy)phenyl)methanamine (136a)

LiAlH$_4$ (3.4 mL, 2M solution in THF) was added to a solution of compound 135 (114 mg, 0.69 mmol) at 0° C. and then the mixture was brought to room temperature and stirred for 4.5 h. After completion of reaction, the reaction mixture was cooled to 0° C. and carefully quenched the reaction with a saturated solution of potassium-sodium tartarate tetrahydrate by dropwise addition. The reaction mixture was filtered on a Celite bed and the filtrate was dried (Na$_2$SO$_4$) filtered and evaporated. The residue was purified on flash silica gel column chromatography (CH$_2$Cl$_2$:MeOH:NH$_4$OH=25:1:0.1) to yield the compound 136a (which was contaminated minor amount of fluorine reduced product), yield 86 mg (74%) as a colorless syrup. $^1$H NMR (CD$_3$OD, 300 MHz) δ 7.19-7.25 (m, 2H), 6.87-6.97 (m, 2H), 4.66-4.69 (m, 1H), 4.29-4.32 (m, 1H), 4.20-4.22 (m, 1H), 4.02-4.11 (m, 1H), 3.75-3.79 (m, 2H). HRMS calculated for $C_9H_{13}NOF$ $(M+H)^+$: 170.0981. found 170.0982.

Compound 136b was prepared in a similar manner.

EXAMPLE 6

This Example illustrates methods of evaluating pharmacological properties of compounds illustrated in Example 5.

Pharmacology

Cell Culture and Membrane Preparation.

Chinese hamster ovary (CHO) cells stably expressing either the recombinant $hA_1$ or $hA_3AR$ and human embryonic kidney (HEK) 293 cells stably expressing the human (h) $A_{2A}AR$ were cultured in DMEM and F12 (1:1), supplemented with 10% fetal bovine serum, 100 units/mL penicillin, 100 µg/mL streptomycin, and 2 µmol/mL glutamine. In addition, 800 µg/mL Geneticin and 500 µg/mL hygromycin were added to the $A_{2A}$ media and to the $A_1$ and $A_3$ media, respectively. After harvesting the cells, they were homogenized for 10 sec with an electric homogenizer, pipetted into 1-mL vials, and then stored at −80° C. until binding experiments were conducted. The concentration of protein was determined using a BCA Protein Assay Kit from Pierce Biotechnology (Rockford, Ill.).

Radioligand Membrane Binding Studies.

Radioligand binding assays at $A_1$, $A_{2A}$, and $A_3ARs$ were performed according to the procedures described previously. Each tube in the binding assay contained 100 µL of membrane suspension (20 µg of protein), 50 pt of a stock solution of agonist radioligand, and 50 µL of increasing concentrations of the test ligands in Tris-HCl buffer (50 mM, pH 7.5) containing 10 mM $MgCl_2$. Nonspecific binding was determined using a final concentration of 10 µM NECA, a non-specific agonist, diluted with the buffer.

The mixtures were incubated at 25° C. for 60 min. Binding reactions were terminated by filtration through Whatman GF/B filters under a reduced pressure using a MT-24 cell harvester (Brandell, Gaithersburg, Md.). Filters were washed three times with 5 ml of 50 mM ice-cold Tris-HCl buffer (pH 7.5). The radioactive agonists [$^3$H]R-PIA and [$^3$H]CGS21680 were used for the $A_1$ and $A_{2A}AR$ assays, respectively, while [$^{125}$I]AB-MECA was used for the $A_3AR$ assay. All of the filters were washed 3 times with Tris-HCl, pH 7.5. Filters for $A_1$ and $A_{2A}AR$ binding were placed in scintillation vials containing 5 ml of Hydrofluor scintillation buffer and counted using a PerkinElmer Tricarb 2810TR Liquid Scintillation Analyzer. Filters for $A_3AR$ binding were counted using a PerkinElmer Cobra II γ-counter.

cAMP Accumulation Assay.

Intracellular cAMP levels were measured with a competitive protein binding method. CHO cells that expressed the recombinant $hA_3AR$ were harvested by trypsinization. After centrifugation and resuspended in medium, cells were planted in 24-well plates in 1.0 mL medium. After 24 h, the medium was removed and cells were washed three times with 1 mL DMEM, containing 50 mM HEPES, pH 7.4. Cells were then treated with the test agonist in the presence of rolipram (10 µM) and adenosine deaminase (3 units/mL). After 45 min forskolin (10 µM) was added to the medium, and incubation was continued for an additional 15 min. The reaction was terminated by removing the supernatant, and cells were lysed upon the addition of 200 µL of 0.1 M ice-cold HCl. The cell lysate was resuspended and stored at −20° C. For determination of cAMP production, 100 µl of the HCl solution was used in the Sigma Direct cAMP Enzyme Immunoassay following the instructions provided with the kit. The results were interpreted using a Bio-Tek Instruments ELx808 Ultra Microplate reader at 405 nm.

Data Analysis

Binding and functional parameters were calculated using Prism 5.0 software (GraphPAD, San Diego, Calif., USA). $IC_{50}$ values obtained from competition curves were converted to $K_i$ values using the Cheng-Prusoff equation. Data were expressed as mean±standard error.

EXAMPLE 7

This Example illustrates the pharmacological properties of compounds illustrated in Examples 4-5. The binding affinity or % inhibition of cyclic AMP data are set forth in Table 2.

TABLE 2

Potency of a series of truncated (N)-methanocarba adenosine derivatives at three subtypes of hARs and relative efficacy at $hA_1AR$.

106-128

Figure 11:
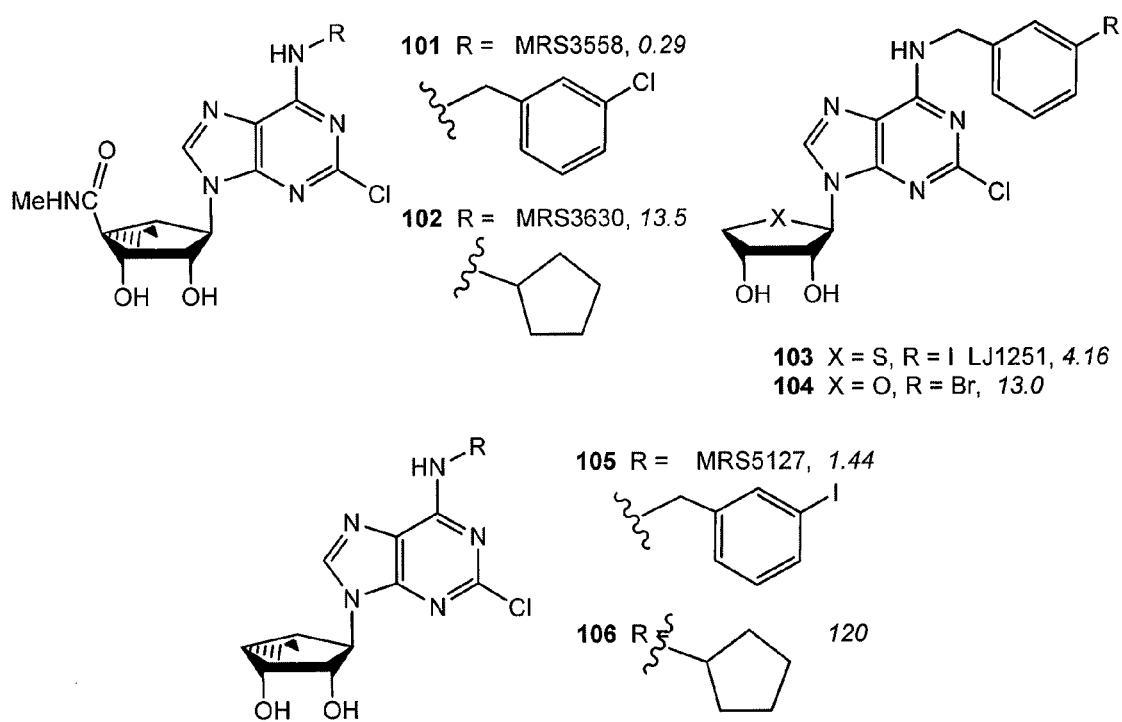
FIG. 11 depicts the structures of compounds 101-106.

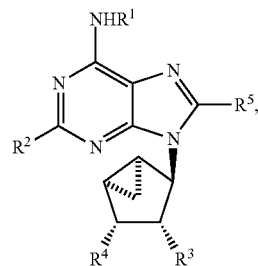

wherein $R^2$ is chloro, $R^3$ and $R^4$ are OH, and $R^5$ is H. Structures of compounds 101-106 are shown in FIG. 11

| | | Affinity $K_i$, nM or (% inhibition)[a] | | | % Inhibition, cyclic AMP[d] |
|---|---|---|---|---|---|
| Compd | $R^1$ = | $A_1$ | $A_{2A}$ | $A_3$ | $A_1$ |
| 101[b] | | 260 ± 60 | 2300 ± 100 | 0.29 ± 0.04 | |
| 102[b] | | 18.3 ± 6.3 | 3250 ± 300 | 13.1 ± 5.1 | |
| 105[b] | | 3040 ± 610 | 1080 ± 310 | 1.44 ± 0.60 | |
| 107 | H | 350 ± 90 | 3140 ± 450 | 160 ± 42 | 68.1 ± 4.4 |

TABLE 2-continued

Potency of a series of truncated (N)-methanocarba adenosine derivatives at three subtypes of hARs and relative efficacy at hA$_1$AR.

106-128

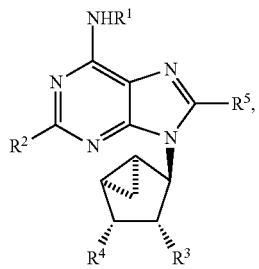

wherein R$^2$ is chloro, R$^3$ and R$^4$ are OH, and R$^5$ is H. Structures of compounds 101-106 are shown in FIG. 11

| Compd | R$^1$ = | Affinity K$_i$, nM or (% inhibition)$^a$ | | | % Inhibition, cyclic AMP$^d$ |
|---|---|---|---|---|---|
| | | A$_1$ | A$_{2A}$ | A$_3$ | A$_1$ |
| 108 | cyclopropyl | 210 ± 30 | 3700 ± 340 | 12.1 ± 3.4 | 79.0 ± 18.8 |
| 109 | cyclobutyl | 51.6 ± 12.6 | 3020 ± 90 | 5.9 ± 0.5 | 46.7 ± 2.1 |
| 106$^b$ | cyclopentyl | 109 ± 16 | 1640 ± 360 | 120 ± 31 | |
| 110 | cyclohexyl | 140 ± 10 | 2720 ± 450 | 500 ± 120 | 38.0 ± 17.6 |
| 111 | cycloheptyl | 230 ± 30 | 3930 ± 520 | 560 ± 90 | 48.1 ± 10.2 |
| 112 | cyclooctyl | 760 ± 110 | (43%) | 1530 ± 60 | 40.1 ± 9.0 |
| 113 | norbornyl | 82.6 ± 15.8 | 2450 ± 90 | 315 ± 48 | 62.1 ± 18.5 |
| 114 | norbornyl | 200 ± 30 | 4080 ± 170 | 236 ± 43 | 27.8 ± 6.2 |
| 115 | CH$_2$CH$_3$ | 930 ± 110 | (11%) | 6.6 ± 1.6 | |
| 116 | (CH$_2$)$_3$F | 72.7 ± 28.0 | (29%) | 32.4 ± 6.7 | 23.2 ± 2.6 |

TABLE 2-continued

Potency of a series of truncated (N)-methanocarba adenosine derivatives at three subtypes of hARs and relative efficacy at hA$_1$AR.

106-128

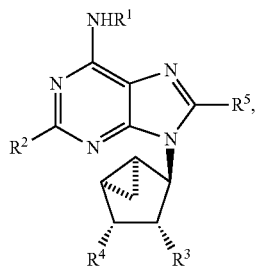

wherein R$^2$ is chloro, R$^3$ and R$^4$ are OH, and R$^5$ is H. Structures of compounds 101-106 are shown in FIG. 11

| Compd | R$^1$ = | Affinity K$_i$, nM or (% inhibition)$^a$ | | | % Inhibition, cyclic AMP$^d$ |
|---|---|---|---|---|---|
| | | A$_1$ | A$_{2A}$ | A$_3$ | A$_1$ |
| 117 | (isopropyl) | 72.2 ± 16.4 | (39%) | 12 ± 1 | 50.5 ± 6.4 |
| 118 | (sec-butyl) | 78.8 ± 15.6 | 3700 ± 300 | 52 ± 14 | 28.6 ± 3.8 |
| 119 | (cyclopropylmethyl) | 68.4 ± 8.9 | 4410 ± 1090 | 8.9 ± 1.9 | 81.0 ± 21.1 |
| 120$^c$ | (1-cyclopropylethyl) | 86.8 ± 23.7 | (41%) | 110 ± 17 | 45.5 ± 4.8 |
| 121 | (dicyclopropylmethyl) | 47.9 ± 10.5 | 3950 ± 410 | 470 ± 15 | 94.3 ± 5.3 |
| 122 | (2-fluorobenzyl) | 4790 ± 670 | (31%) | 41.5 ± 1.0 | |
| 123 | (2-(2-fluoroethoxy)benzyl) | (46%) | (32%) | 10.3 ± 1.5 | |

TABLE 2-continued

Potency of a series of truncated (N)-methanocarba adenosine derivatives at three subtypes of hARs and relative efficacy at hA$_1$AR.

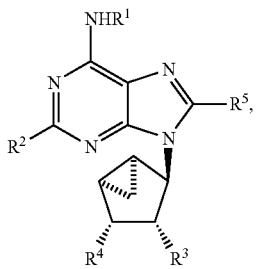

106-128 wherein R$^2$ is chloro, R$^3$ and R$^4$ are OH, and R$^5$ is H. Structures of compounds 101-106 are shown in FIG. 11

| Compd | R$^1$ = | Affinity K$_i$, nM or (% inhibition)$^a$ | | | % Inhibition, cyclic AMP$^d$ |
|---|---|---|---|---|---|
| | | A$_1$ | A$_{2A}$ | A$_3$ | A$_1$ |
| 124 | [2-ethoxybenzyl] | (34%) | (32%) | 15.2 ± 3.0 | |
| 125 | [3-(2-fluoroethoxy)benzyl] | 3580 ± 220 | (46%) | 114 ± 45 | |
| 126 | [2,5-difluorobenzyl] | 1260 ± 240 | (38%) | 16.5 ± 2.8 | |
| 127 | [2,3-difluoro-4-methoxybenzyl] | (41%) | (30%) | 83.2 ± 35.7 | |
| 128 | [4,5-difluoro-2-methoxybenzyl] | 1910 ± 310 | 7510 ± 690 | 40.4 ± 13.1 | |

$^a$Using CHO or HEK293 (A$_{2A}$ only) cells stably expressing a hAR; affinity was expressed as K$_i$ value (n = 3-5) or percent inhibition of radioligand binding at 10 μM.
$^b$Values from Tchilibon, S., et al., *J. Med. Chem.* 2005, 48, 1745-1758; Jacobson, K. A., et al., *J. Med. Chem.* 2005, 48, 8103-8107; and Tosh, D. K., et al., *J. Med. Chem.* 2009, 52, 7580-7592. Compounds 105 and 106 were prepared as reported previously; see Tosh, D. K., et al., *J. Med. Chem.* 2009, 52, 7580-7592.
$^c$120 is a diastereomeric mixture.
$^d$Maximal efficacy (at 10 μM) in an A$_1$AR functional assay, determined by inhibition of forskolin-stimulated cyclic AMP production in AR-transfected CHO cells, expressed as percent inhibition (mean ± standard error, n = 3-5) in comparison to effect (100%) of full agonist CPA 130 at 10 μM. The value for NECA was 100 ± 15.

The data set forth in Table 2 show that compounds 110-114 and 120-121 are selective to the A$_1$ AR compared to the A$_3$ AR.

Figure 12:
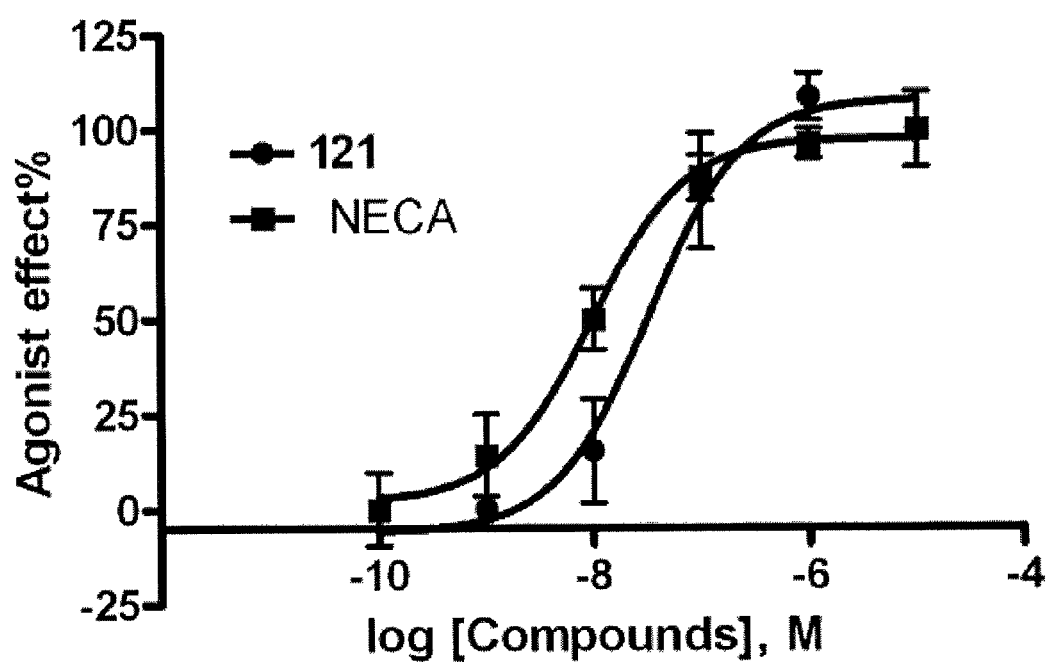
FIG. 12 depicts the concentration-response curve of compound 121 compared to full agonist NECA in the inhibition of cyclic AMP production at the $hA_1AR$ expressed in CHO cells.

FIG. 12 shows that compound 121 is a full agonist of the A$_1$ AR. The curve for NECA (5'-N-ethylcarboxamidoadenosine), a known full agonist, is provided for comparison. The C-log P of compound 121 is 1.41, with the optimal for small molecular pharmaceutical substances being typically 2-3. The comparable parameter for the related A$_1$ AR-selective riboside and prototypical agonist CPA is 0.14, which is less desirable. Also, the polar surface area (PSA) for 121 and CPA are calculated to be 92.8 and 122 Å, respectively. Most drug-like small molecules have a PSA smaller than 120 Å. Compound 121 has fewer hydroxyl groups than CPA, which would favor bioavailability. The molecular weight of 121 of 376 is comfortably within the preferred range. Therefore, by several criteria, the full agonist of the A$_1$ AR 121 is more drug-like than CPA.

EXAMPLE 8

Figure 13:
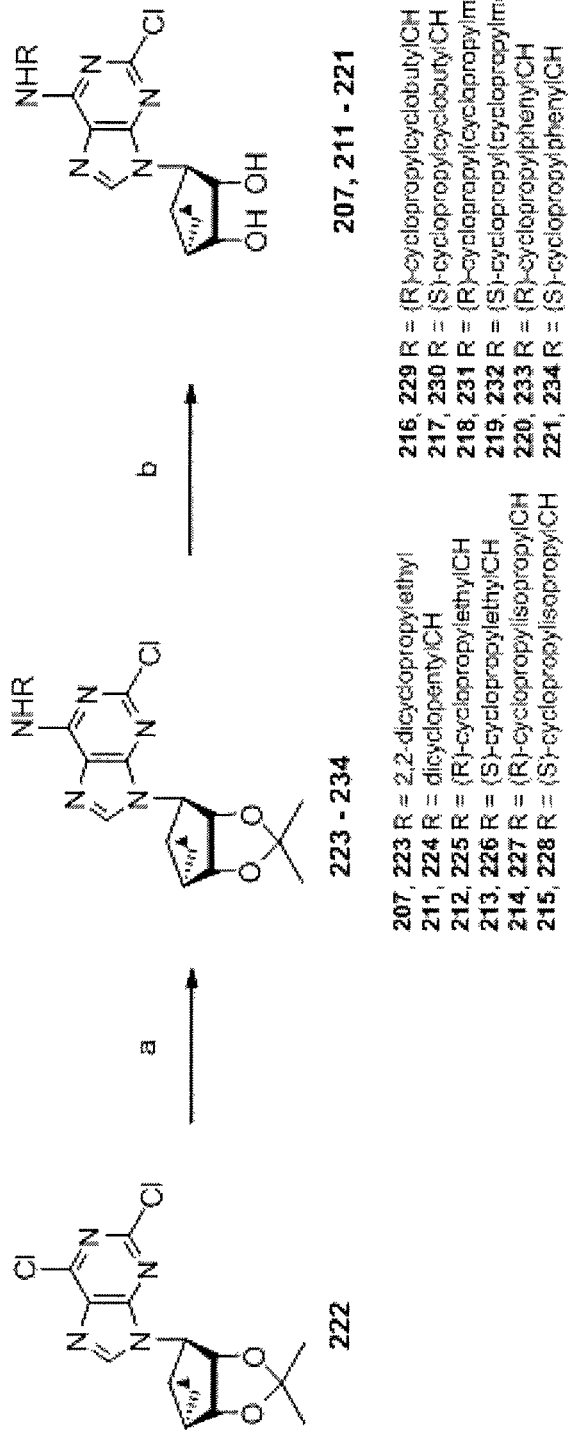
FIG. 13 depicts a reaction scheme to prepare compounds 207 and 211-221.

This Example illustrates a method of preparing further compounds in accordance with an embodiment of the invention. FIG. 13 shows a schematic of a preparative method. The synthetic route to the truncated derivatives involved nucleophilic displacement by the appropriate amine of a 6-chloroadenine group in a 2',3'-isopropylidene-protected precursor 222.

Examples of appropriate amines include:

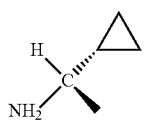
(S)-1-cyclopropylethanamine,

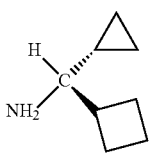
(R)-cyclobutyl(cyclopropyl)methanamine,

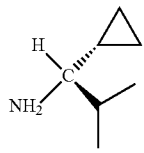
(S)-1-cyclopropyl-2-methylpropan-1-amine,

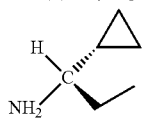
(S)-1-cyclopropylpropan-1-amine,

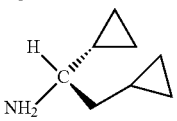
(S)-1,2-dicyclopropylethanamine,

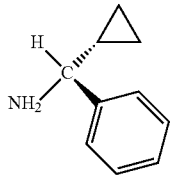
(R)-cyclopropyl(phenyl)methanamine, and dicyclopropylmethylamine.

All reagents and solvents (regular and anhydrous) were of analytical grade and obtained from commercial suppliers and used without further purification. All amines were purchased from Asiba Pharmatech (Edison, N.J.), except dicyclopropylethylamine, which was obtained from Ryan Scientific, Inc. (Mount Pleasant, S.C.). Reactions were conducted under an atmosphere of nitrogen whenever anhydrous solvents were used. All reactions were monitored by thin-layer chromatography (TLC) using silica gel coated plates with a fluorescence indicator which were visualized: (a) under UV light, (b) by dipping in a mixture of anisaldehyde (2.5 mL)/conc. $H_2SO_4$ (5 mL)/methanol (425 mL) or (c) by dipping the plate in a solution of ninhydrin (0.3 g in 100 mL EtOH, containing AcOH, 1.3 mL) followed by heating. Silica gel column chromatography was performed with silica gel ($SiO_2$, 200-400 mesh, 60 Å) using moderate air pressure. Evaporation of solvents was carried out under reduced pressure at a temperature below 50° C. After column chromatography, appropriate fractions were pooled, evaporated, and dried at high vacuum for at least 12 h to give the desired products in high purity. $^1$H NMR ascertained sample purity and spectra were recorded with a Bruker 400 MHz NMR spectrometer. Chemical shifts are reported in parts per million (ppm) relative to tetramethylsilane or using deuterated solvent as the internal standard (δH: CDCl$_3$ 7.26 ppm). ESI—High Resolution Mass Spectroscopic (HRMS) measurements were performed on a proteomics optimized Q-TOF-2 (Micromass-Waters) using external calibration with polyalanine. Observed mass accuracies are those expected on the basis of known performance of the instrument as well as the trends in masses of standard compounds observed at intervals during the series of measurements. Reported masses are observed masses uncorrected for this time-dependent drift in mass accuracy. TLC analysis was carried out on glass sheets precoated with silica gel F$_{254}$ (0.2 mm) from Aldrich. The purity of final nucleoside derivatives was checked using a Hewlett-Packard 1100 HPLC equipped with a Zorbax SB-Aq 5 µm analytical column (50×4.6 mm; Agilent Technologies Inc, Palo Alto, Calif.). Mobile phase: linear gradient solvent system: 5 mM TBAP (tetrabutylammonium dihydrogenphosphate)-CH$_3$CN from 80:20 to 0:100 in 13 min; the flow rate was 0.5 mL/min. Peaks were detected by UV absorption with a diode array detector at 230, 254, and 280 nm. All derivatives tested for biological activity showed >95% purity by HPLC analysis (detection at 254 nm).

(1R,2R,3S,4R,5S)-4-(2-Chloro-6-(2,2-dicyclopropylethylamino)-9H-purin-9-yl)-2,3-O-(isopropylidene)-bicyclo[3.1.0]hexane (223)

2,2-Dicyclopropyl ethylamine (38 mg, 0.30 mmol) and triethylamine (0.12 mL, 0.84 mmol) was added to a solution of compound 222 (20.91 mg, 0.061 mmol) in methanol (1.5 mL) and stirred at room temperature for overnight. The reaction mixture was evaporated under vacuum and the residue was purified on flash column chromatography (hexane:ethyl acetate=1:1) to give the desired product 223 (22 mg, 84%) as a syrup. $^1$H NMR (CD$_3$OD, 400 MHz) δ 8.14 (s, 1H), 5.36 (t, J=6.0 Hz, 1H), 4.97 (s, 1H), 4.69 (d, J=7.2 Hz, 1H), 3.73 (d, J=6.4 Hz, 2H), 2.09-2.03 (m, 1H), 1.76-1.71 (m, 1H), 1.52 (s, 3H), 1.25 (s, 3H), 0.95-0.90 (m, 2H), 0.75-0.72 (m, 2H), 0.51-0.42 (m, 5H), 0.28-0.17 (m, 4H). HRMS calculated for $C_{22}H_{29}ClN_5O_2$ (M+H)$^+$: 430.2010. found 430.2013.

(1R,2R,3S,4R,5S)-4-(2-Chloro-6-((R)-1-cyclopropylpropylamino)-9H-purin-9-yl)-2,3-O-(isopropylidene)-bicyclo[3.1.0]hexane (225)

Compound 225 (78%) was prepared from compound 222 following the same method for compound 223. $^1$H NMR (CD$_3$OD, 400 MHz) δ 8.13 (s, 1H), 5.36 (t, J=6.4 Hz, 1H), 4.96 (s, 1H), 4.69 (d, J=7.2 Hz, 1H), 3.66 (br s, 1H), 2.07-2.04 (m, 1H), 1.86-1.79 (m, 1H), 1.77-1.70 (m, 2H), 1.52 (s, 3H), 1.25 (s, 3H), 1.03-0.99 (m, 4H), 0.95-0.90 (m, 2H), 0.62-0.56 (m, 1H), 0.45-0.41 (m, 2H), 0.36-0.33 (m, 1H). HRMS calculated for $C_{20}H_{27}ClN_5O_2$ (M+H)$^+$: 404.1853. found 404.1855.

(1R,2R,3S,4R,5S)-4-(2-Chloro-6-((S)-1-cyclopropylpropylamino)-9H-purin-9-yl)-2,3-O-(isopropylidene)-bicyclo[3.1.0]hexane (226)

Compound 226 (80%) was prepared from compound 222 following the same method for compound 223. $^1$H NMR (CD$_3$OD, 400 MHz) δ 8.13 (s, 1H), 5.36 (t, J=6.4 Hz, 1H), 4.96 (s, 1H), 4.69 (d, J=7.2 Hz, 1H), 3.67 (br s, 1H), 2.09-2.03 (m, 1H), 1.88-1.79 (m, 1H), 1.77-1.72 (m, 2H), 1.52 (s, 3H), 1.25 (s, 3H), 1.03-0.99 (m, 4H), 0.96-0.89 (m, 2H), 0.61-0.56 (m, 1H), 0.47-0.41 (m, 2H), 0.36-0.30 (m, 1H). HRMS calculated for $C_{20}H_{27}ClN_5O_2$ (M+H)$^+$: 404.1853. found 404.1854.

(1R,2R,3S,4R,5S)-4-(2-Chloro-6-((R)-1-cyclopropyl-2-methyl-propylamino)-9H-purin-9-yl)-2,3-O-(isopropylidene)-bicyclo[3.1.0]hexane (227)

Compound 227 (75%) was prepared from compound 222 following the same method for compound 223. $^1$H NMR (CD$_3$OD, 400 MHz) δ 8.15 (s, 1H), 5.36 (t, J=6.0 Hz, 1H), 4.97 (s, 1H), 4.70 (d, J=6.4 Hz, 1H), 3.62 (t, J=7.2 Hz, 1H), 2.08-2.03 (m, 1H), 1.76-1.72 (m, 1H), 1.52 (s, 3H), 1.25 (m, 4H), 1.08-1.05 (m, 7H), 0.96-0.88 (m, 2H), 0.65-0.61 (m, 1H), 0.45-0.36 (m, 2H). HRMS calculated for $C_{21}H_{29}ClN_5O_2$ (M+H)$^+$: 418.2010. found 418.2004.

(1R,2R,3S,4R,5S)-4-(2-Chloro-6-((S)-1-cyclopropyl-2-methyl-propylamino)-9H-purin-9-yl)-2,3-O-(isopropylidene)-bicyclo[3.1.0]hexane (228)

Compound 228 (78%) was prepared from compound 222 following the same method for compound 223. $^1$H NMR (CD$_3$OD, 400 MHz) δ 8.15 (s, 1H), 5.36 (t, J=6.0 Hz, 1H), 4.97 (s, 1H), 4.71 (d, J=6.4 Hz, 1H), 3.61 (t, J=7.2 Hz, 1H), 2.08-2.04 (m, 1H), 1.76-1.71 (m, 1H), 1.51 (s, 3H), 1.25 (m, 4H), 1.08-1.05 (m, 7H), 0.96-0.88 (m, 2H), 0.65-0.61 (m, 1H), 0.45-0.36 (m, 2H). HRMS calculated for $C_{21}H_{29}ClN_5O_2$ (M+H)$^+$: 418.2010. found 418.2017.

(1R,2R,3S,4R,5S)-4-(2-Chloro-6-((R)-cyclopropyl-cyclobutylmethylamino)-9H-purin-9-yl)-2,3-O-(isopropylidene)-bicyclo[3.1.0]hexane (229)

Compound 229 (83%) was prepared from compound 222 following the same method for compound 223.11-1 NMR (CD$_3$OD, 400 MHz) δ 8.15 (s, 1H), 5.36 (t, J=6.0 Hz, 1H), 4.96 (s, 1H), 4.69 (d, J=7.2 Hz, 1H), 3.85 (br s, 1H), 2.72-2.67 (m, 1H), 2.10-2.89 (m, 6H), 1.87-1.71 (m, 2H), 1.52 (s, 3H), 1.25 (s, 3H), 0.96-0.89 (m, 3H), 0.58-0.53 (m, 1H), 0.39-0.36 (m, 3H). HRMS calculated for $C_{22}H_{29}ClN_5O_2$ (M+H)$^+$: 430.2010. found 430.2018.

(1R,2R,3S,4R,5S)-4-(2-Chloro-6-((S)-cyclopropyl-cyclobutylmethylamino)-9H-purin-9-yl)-2,3-O-(isopropylidene)-bicyclo[3.1.0]hexane (230)

Compound 230 (82%) was prepared from compound 222 following the same method for compound 223. $^1$H NMR (CD$_3$OD, 400 MHz) δ 8.13 (s, 1H), 5.36 (t, J=6.0 Hz, 1H), 4.96 (s, 1H), 4.69 (d, J=7.2 Hz, 1H), 3.84 (br s, 1H), 2.71-2.67 (m, 1H), 2.09-2.89 (m, 6H), 1.87-1.71 (m, 2H), 1.51 (s, 3H), 1.25 (s, 3H), 0.95-0.88 (m, 3H), 0.58-0.54 (m, 1H), 0.37-0.36 (m, 3H). HRMS calculated for $C_{22}H_{29}ClN_5O_2$ (M+H)$^+$: 430.2010. found 430.2008.

(1R,2R,3S,4R,5S)-4-(2-Chloro-6-((R)-1,2-dicyclopropylethylamino)-9H-purin-9-yl)-2,3-O-(isopropylidene)-bicyclo[3.1.0]hexane (231)

Compound 231 (75%) was prepared from compound 222 following the same method for compound 223. $^1$H NMR (CD$_3$OD, 400 MHz) δ 8.13 (s, 1H), 5.36 (t, J=6.4 Hz, 1H), 4.96 (s, 1H), 4.69 (d, J=7.2 Hz, 1H), 3.80 (br s, 1H), 2.06-2.03 (m, 1H), 1.73-1.57 (m, 3H), 1.51 (s, 3H), 1.25 (s, 3H), 1.09-1.06 (m, 1H), 0.94-0.85 (m, 3H), 0.60-0.58 (m, 1H), 0.44-0.35 (m, 5H), 0.17-0.16 (m, 1H), 0.09-0.07 (m, 1H). HRMS calculated for $C_{22}H_{29}ClN_5O_2$ (M+H)$^+$: 430.2010. found 430.2025.

(1R,2R,3S,4R,5S)-4-(2-Chloro-6-((S)-1,2-dicyclopropylethylamino)-9H-purin-9-yl)-2,3-O-(isopropylidene)-bicyclo[3.1.0]hexane (232)

Compound 232 (77%) was prepared from compound 222 following the same method for compound 223. $^1$H NMR (CD$_3$OD, 400 MHz) δ 8.13 (s, 1H), 5.36 (t, J=6.4 Hz, 1H), 4.96 (s, 1H), 4.69 (d, J=7.2 Hz, 1H), 3.80 (br s, 1H), 2.07-2.03 (m, 1H), 1.74-1.58 (m, 3H), 1.51 (s, 3H), 1.25 (s, 3H), 1.09-1.05 (m, 1H), 0.95-0.84 (m, 3H), 0.60-0.58 (m, 1H), 0.44-0.35 (m, 5H), 0.17-0.15 (m, 1H), 0.09-0.07 (m, 1H). HRMS calculated for $C_{22}H_{29}ClN_5O_2$ (M+H)$^+$: 430.2010. found 430.2002.

(1R,2R,3S,4R,5S)-4-(2-Chloro-6-((R)-cyclopropylphenylmethylamino)-9H-purin-9-yl)-2,3-O-(isopropylidene)-bicyclo[3.1.0]hexane (233)

Compound 233 (81%) was prepared from compound 222 following the same method for compound 223. $^1$H NMR (CD$_3$OD, 400 MHz) δ 8.15 (s, 1H), 7.48 (d, J=7.6 Hz, 2H), 7.33 (t, J=7.6 Hz, 2H), 2.24 (t, J=7.2 Hz, 1H), 5.35 (t, J=6.0 Hz, 1H), 4.95 (s, 1H), 4.69 (d, J=7.2 Hz, 1H), 3.60 (br s, 1H), 2.06-2.03 (m, 1H), 1.74-1.71 (m, 1H), 1.51 (s, 3H), 1.43-1.37 (m, 1H), 1.24 (s, 3H), 0.94-0.89 (m, 2H), 0.65-0.63 (m, 2H), 0.53-0.46 (m, 2H). HRMS calculated for $C_{24}H_{27}ClN_5O_2$ (M+H)$^+$: 452.1853. found 452.1858.

(1R,2R,3S,4R,5S)-4-(2-Chloro-6-((S)-cyclopropylphenylmethylamino)-9H-purin-9-yl)-2,3-O-(isopropylidene)-bicyclo[3.1.0]hexane (234)

Compound 234 (82%) was prepared from compound 222 following the same method for compound 223. $^1$H NMR (CD$_3$OD, 400 MHz) δ 8.15 (s, 1H), 7.48 (d, J=7.2 Hz, 2H), 7.33 (t, J=7.6 Hz, 2H), 2.24 (t, J=7.2 Hz, 1H), 5.35 (t, J=6.8 Hz, 1H), 4.95 (s, 1H), 4.69 (d, J=7.2 Hz, 1H), 3.60 (br s, 1H), 2.06-2.03 (m, 1H), 1.75-1.71 (m, 1H), 1.51 (s, 3H), 1.42-1.37 (m, 1H), 1.24 (s, 3H), 0.96-0.88 (m, 2H), 0.66-0.62 (m, 2H), 0.54-0.43 (m, 2H). HRMS calculated for $C_{24}H_{27}ClN_5O_2$ (M+H)$^+$: 452.1853. found 452.1856.

(1R,2R,3S,4R,5S)-4-(2-Chloro-6-(2,2-dicyclopropylethylamino)-9H-purin-9-yl)bicyclo[3.1.0]hexane-2,3-diol (207)

Dowex 50 resin (8 mg) was added to a solution of compound 223 (12 mg, 0.027 mmol) in methanol (0.5 mL) and water (0.5 mL) and stirred at room temperature for overnight. Reaction mixture was filtered on a celite bed, filtrate was evaporated under vacuum and the residue was purified on flash silica gel column chromatography (CH$_2$Cl$_2$:MeOH=35:1) to give the desired compound 207 (8.2 mg, 74%) as a syrup. $^1$H NMR (CD$_3$OD, 400 MHz) δ 8.15 (s, 1H), 4.79 (s, 1H), 4.71 (t, J=5.6 Hz, 1H), 4.90 (d, J=6.8 Hz, 1H), 3.72 (d, J=6.4 Hz, 2H), 2.01-1.96 (m, 1H), 1.71-1.64 (m, 1H), 1.34-1.30 (m 2H), 0.78-0.72 (m, 2H), 0.51-0.42 (m, 5H), 0.28-0.17 (m, 4H). HRMS calculated for $C_{19}H_{25}ClN_5O_2$ (M+H)$^+$: 390.1697. found 390.1708.

(1R,2R,3S,4R,5S)-4-(2-Chloro-6-(dicyclopentylmethylamino)-9H-purin-9-yl)bicyclo[3.1.0]hexane-2,3-diol (211)

Dicyclopentylmethylamine (1.0 mg, 0.024 mmol) and triethylamine (0.1 mL, 0.16 mmol) was added to a solution of compound 222 (4.2 mg, 0.012 mmol) in methanol (0.8 mL) and stirred at room temperature for overnight. The reaction mixture was evaporated under vacuum and the residue was roughly purified on flash silica gel column chromatography. The resulting compound 224 was dissolved with methanol (0.6 mL) and water (0.3 mL), Dowex50 (4 mg) was added into the solution and stirred at room temperature for overnight. After completion of starting material, reaction mixture was filtered and the filtrate was evaporated under vacuum and residue was purified on flash silica gel column chromatography ($CH_2Cl_2$:MeOH=30:1) to give the desired compound 11 (3.4 mg, 64%) as a syrup. $^1$H NMR ($CD_3OD$, 400 MHz) δ 8.17 (s, 1H), 4.80 (s, 1H), 4.71 (t, J=6.0 Hz, 1H), 4.40 (t, J=6.8 Hz, 1H), 3.91 (d, J=6.4 Hz, 1H), 2.20-1.18 (m, 1H), 1.98-1.96 (m, 1H), 1.81-1.74 (m, 4H), 1.69-1.53 (m, 10H), 1.42-1.29 (m, 4H), 0.92-0.90 (m, 1H), 0.81-0.74 (m, 1H). HRMS calculated for $C_{19}H_{25}ClN_5O_2$ (M+H)$^+$: 390.1697. found 390.1708.

(1R,2R,3S,4R,5S)-4-(2-Chloro-6-((R)-1-cyclopropylpropylamino)-9H-purin-9-yl)bicyclo[3.1.0]hexane-2,3-diol (212)

Compound 212 (69%) was prepared from compound 225 following the same method for compound 207. $^1$H NMR ($CD_3OD$, 400 MHz) δ 8.15 (s, 1H), 4.79 (s, 1H), 4.71 (t, J=5.6 Hz, 1H), 3.89 (d, J=6.8 Hz, 1H), 3.66 (br s, 1H), 2.00-1.97 (m, 1H), 1.84-1.65 (m, 3H), 1.34-1.28 (m, 2H), 1.01 (t, J=7.6 Hz, 3H), 0.80-0.74 (m, 1H), 0.60-0.58 (m, 1H), 0.45-0.42 (m, 2H), 0.36-0.32 (m, 1H). HRMS calculated for $C_{17}H_{23}ClN_5O_2$ (M+H)$^+$: 364.1540. found 364.1538.

(1R,2R,3S,4R,5S)-4-(2-Chloro-6-((S)-1-cyclopropylpropylamino)-9H-purin-9-yl)bicyclo[3.1.0]hexane-2,3-diol (213)

Compound 213 (68%) was prepared from compound 226 following the same method for compound 207.111 NMR ($CD_3OD$, 400 MHz) δ 8.15 (s, 1H), 4.79 (s, 1H), 4.71 (t, J=5.6 Hz, 1H), 3.89 (d, J=6.8 Hz, 1H), 3.67 (br s, 1H), 2.02-1.98 (m, 1H), 1.86-1.59 (m, 3H), 1.32-1.24 (m, 2H), 1.01 (t, J=7.6 Hz, 3H), 0.78-0.76 (m, 1H), 0.59-0.57 (m, 1H), 0.45-0.42 (m, 2H), 0.34-0.32 (m, 1H). HRMS calculated for $C_{17}H_{23}ClN_5O_2$ (M+H)$^+$: 364.1540. found 364.1535.

(1R,2R,3S,4R,5S)-4-(2-Chloro-6-((R)-1-cyclopropyl-2-methyl-propylamino)-9H-purin-9-yl)bicyclo[3.1.0]hexane-2,3-diol (214)

Compound 214 (82%) was prepared from compound 227 following the same method for compound 207. $^1$H NMR ($CD_3OD$, 400 MHz) δ 8.17 (s, 1H), 4.79 (s, 1H), 4.71 (t, J=5.6 Hz, 1H), 3.89 (d, J=6.4 Hz, 1H), 3.62 (t, J=7.2 Hz, 1H), 2.07-1.97 (m, 2H), 1.88-1.64 (m, 1H), 1.36-1.31 (m, 1H), 1.08-1.05 (m, 8H), 0.80-0.74 (m, 1H), 0.66-0.61 (m, 1H), 0.45-0.36 (m, 2H). HRMS calculated for $C_{18}H_{25}ClN_5O_2$ (M+H)$^+$: 378.1697. found 378.1691.

(1R,2R,3S,4R,5S)-4-(2-Chloro-6-((S)-1-cyclopropyl-2-methyl-propylamino)-9H-purin-9-yl)bicyclo[3.1.0]hexane-2,3-diol (215)

Compound 215 (81%) was prepared from compound 228 following the same method for compound 207. $^1$H NMR ($CD_3OD$, 400 MHz) δ 8.17 (s, 1H), 4.79 (s, 1H), 4.71 (t, J=5.6 Hz, 1H), 3.89 (d, J=6.4 Hz, 1H), 3.63 (t, J=7.2 Hz, 1H), 2.09-1.96 (m, 2H), 1.86-1.64 (m, 1H), 1.34-1.30 (m, 1H), 1.08-1.05 (m, 8H), 0.80-0.74 (m, 1H), 0.65-0.61 (m, 1H), 0.45-0.36 (m, 2H). HRMS calculated for $C_{18}H_{25}ClN_5O_2$ (M+H)$^+$: 378.1697. found 378.1694.

(1R,2R,3S,4R,5S)-4-(2-Chloro-6-((R)-cyclopropylcyclobutylmethylamino)-9H-purin-9-yl)bicyclo[3.1.0]hexane-2,3-diol (216)

Compound 216 (74%) was prepared from compound 229 following the same method for compound 207. $^1$H NMR ($CD_3OD$, 400 MHz) δ 8.15 (s, 1H), 4.79 (s, 1H), 4.71 (t, J=5.6 Hz, 1H), 3.89 (d, J=6.4 Hz, 1H), 3.73 (br s, 1H), 2.69-2.64 (m, 1H), 2.10-2.07 (m, 1H), 2.01-1.91 (m, 4H), 1.89-1.80 (m, 1H), 1.69-1.65 (m, 1H), 1.34-1.30 (m, 3H), 0.95-0.91 (m, 1H), 0.78-0.74 (m, 1H), 0.56-0.53 (m, 1H), 0.40-0.36 (m, 2H). HRMS calculated for $C_{19}H_{25}ClN_5O_2$ (M+H)$^+$: 390.1697. found 390.1711.

(1R,2R,3S,4R,5S)-4-(2-Chloro-6-((S)-cyclopropylcyclobutylmethylamino)-9H-purin-9-yl)bicyclo[3.1.0]hexane-2,3-diol (217)

Compound 217 (74%) was prepared from compound 30 following the same method for compound 207. $^1$H NMR ($CD_3OD$, 400 MHz) δ 8.15 (s, 1H), 4.79 (s, 1H), 4.71 (t, J=5.6 Hz, 1H), 3.89 (d, J=6.4 Hz, 1H), 3.73 (br s, 1H), 2.69-2.62 (m, 1H), 2.12-2.07 (m, 1H), 2.03-1.88 (m, 4H), 1.89-1.80 (m, 1H), 1.69-1.65 (m, 1H), 1.34-1.31 (m, 3H), 0.95-0.91 (m, 1H), 0.78-0.76 (m, 1H), 0.56-0.53 (m, 1H), 0.40-0.36 (m, 2H). HRMS calculated for $C_{19}H_{25}ClN_5O_2$ (M+H)$^+$: 390.1697. found 390.1697.

(1R,2R,3S,4R,5S)-4-(2-Chloro-6-((R)-1,2-dicyclopropylethylamino)-9H-purin-9-yl)bicyclo[3.1.0]hexane-2,3-diol (218)

Compound 218 (78%) was prepared from compound 231 following the same method for compound 207. $^1$H NMR ($CD_3OD$, 400 MHz) δ 8.15 (s, 1H), 4.79 (s, 1H), 4.71 (t, J=5.6 Hz, 1H), 3.89 (d, J=6.8 Hz, 1H), 3.80 (br s, 1H), 2.02-1.97 (m, 1H), 1.70-1.61 (m, 2H), 1:34-1.30 (m, 3H), 1.10-1.08 (m, 1H), 0.91-0.76 (m, 2H), 0.62-0.58 (m, 1H), 0.47-0.36 (m, 4H), 0.17-0.07 (m, 2H). HRMS calculated for $C_{19}H_{25}ClN_5O_2$ (M+H)$^+$: 390.1697. found 390.1691.

(1R,2R,3S,4R,5S)-4-(2-Chloro-6-((S)-1,2-dicyclopropylethylamino)-9H-purin-9-yl)bicyclo[3.1.0]hexane-2,3-diol (219)

Compound 219 (76%) was prepared from compound 232 following the same method for compound 207. $^1$H NMR ($CD_3OD$, 400 MHz) δ 8.15 (s, 1H), 4.79 (s, 1H), 4.71 (t, J=5.6 Hz, 1H), 3.89 (d, J=6.8 Hz, 1H), 3.80 (br s, 1H), 2.00-1.97 (m, 1H), 1.69-1.61 (m, 2H), 1.34-1.30 (m, 3H), 1.10-1.08 (m, 1H), 0.89-0.75 (m, 2H), 0.60-0.59 (m, 1H), 0.47-0.36 (m, 4H), 0.17-0.07 (m, 2H). HRMS calculated for $C_{19}H_{25}ClN_5O_2$ (M+H)$^+$: 390.1697. found 390.1697.

(1R,2R,3S,4R,5S)-4-(2-Chloro-6-((R)-cyclopropylphenylmethylamino)-9H-purin-9-yl)bicyclo[3.1.0]hexane-2,3-diol (220)

Compound 220 (80%) was prepared from compound 233 following the same method for compound 207. $^1$H NMR (CD$_3$OD, 400 MHz) δ 8.16 (s, 1H), 7.48 (d, J=7.6 Hz, 2H), 7.33 (t, J=7.6 Hz, 2H), 7.26 (t, J=7.6 Hz, 1H), 4.78 (s, 2H), 4.69 (t, J=5.6 Hz, 1H), 3.88 (t, J=7.2 Hz, 1H), 2.01-1.95 (m, 1H), 1.68-1.63 (m, 1H), 1.42-1.30 (m, 2H), 0.79-0.73 (m, 1H), 0.65-0.62 (m, 2H), 0.54-0.51 (m, 2H). HRMS calculated for C$_{21}$H$_{23}$ClN$_5$O$_2$ (M+H)$^+$: 412.1540. found 412.1533.

(1R,2R,3S,4R,5S)-4-(2-Chloro-6-((S)-cyclopropylphenylmethylamino)-9H-purin-9-yl)bicyclo[3.1.0]hexane-2,3-diol (221)

Compound 221 (79%) was prepared from compound 234 following the same method for compound 207. $^1$H NMR (CD$_3$OD, 400 MHz) δ 8.17 (s, 1H), 7.48 (d, J=7.6 Hz, 2H), 7.33 (t, J=7.6 Hz, 2H), 7.24 (t, J=7.2 Hz, 1H), 4.78 (s, 2H), 4.71 (t, J=5.2 Hz, 1H), 3.88 (t, J=7.6 Hz, 1H), 2.02-1.95 (m, 1H), 1.68-1.65 (m, 1H), 1.43-1.30 (m, 2H), 0.79-0.73 (m, 1H), 0.65-0.60 (m, 2H), 0.54-0.47 (m, 2H). HRMS calculated for C$_{21}$H$_{23}$ClN$_5$O$_2$ (M+H)$^+$: 412.1540. found 412.1544.

EXAMPLE 9

This Example illustrates the pharmacological properties of compounds illustrated in Example 8. The binding affinity or % inhibition of cyclic AMP data, obtained as illustrated in Example 7, are set forth in Table 3.

TABLE 3

In vitro potency of a series of truncated (N)-methanocarba adenosine derivatives in binding to three subtypes of hARs and relative efficacy at hA$_1$AR.

203-207

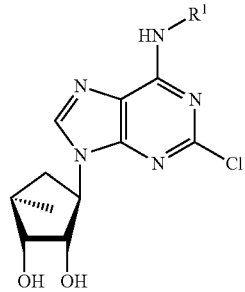

For compounds 208-221, R$^1$ = 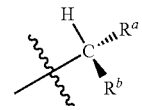

| Compd | R$^1$ = | Affinity K$_i$, nM or (% inhibition)$^a$ | | | % Inhibition, cyclic AMP$^d$ |
| --- | --- | --- | --- | --- | --- |
| | | A$_1$ | A$_{2A}$ | A$_3$ | A$_1$ |
| 203 | H | 350 ± 90 | 3140 ± 450 | 160 ± 42 | 68.1 ± 4.4 |
| 204 | CH$_2$CH$_3$ | 930 ± 110 | (11%) | 6.6 ± 1.6 | ND |
| 205 | cyclopropylmethyl | 68.4 ± 8.9 | 4410 ± 1090 | 8.9 ± 1.9 | 81.0 ± 21.1 |
| 206$^c$ | 1-cyclopropylethyl (R,S) | 86.8 ± 23.7 | (41%) | 110 ± 17 | 45.5 ± 4.8 |
| 207 MRS5721 | dicyclopropylmethyl | 780 ± 100 | (45 ± 3%) | 670 ± 10 | −9.0 ± 4.1 |
| | R$^a$ = | R$^b$ = | | | |
| 208$^d$ | CH$_3$ | CH$_3$ | 72.2 ± 16.4 | (39%) | 12 ± 1 | 50.5 ± 6.4 |
| 209$^d$ | C$_2$H$_5$ | C$_2$H$_5$ | 78.8 ± 15.6 | 3700 ± 300 | 52 ± 14 | 28.6 ± 3.8 |

TABLE 3-continued

| | | | | | | |
|---|---|---|---|---|---|---|
| 121[d] MRS 5474 | cyclopropyl | cyclopropyl | 47.9 ± 10.5 | 3950 ± 410 | 470 ± 15 | 94.3 ± 5.3 |
| 211 5629 | cyclopentyl | cyclopentyl | (34 ± 3%) | (13 ± 3%) | (48 ± 2%) | ND |
| 212 5722 (R) | cyclopropyl | C$_2$H$_5$ | 68.1 ± 5.0 | 3610 ± 500 | 150 ± 2 | 37.3 ± 4.3 |
| 213 5725 (S) | C$_2$H$_5$ | cyclopropyl | 150 ± 10 | 4910 ± 430 | 780 ± 70 | 57.9 ± 1.1 |
| 214 5719 (R) | cyclopropyl | isopropyl | 76.0 ± 8.0 | 1570 ± 180 | 780 ± 80 | 33.8 ± 2.3 |
| 215 5724 (S) | isopropyl | cyclopropyl | 150 ± 50 | 3650 ± 370 | 1720 ± 140 | 20.8 ± 6.1 |
| 216 5730 (R) | cyclobutyl | cyclopropyl | 270 ± 60 | 5470 ± 300 | 2930 ± 480 | 33.4 ± 5.2 |
| 217 5751 (S) | cyclopropyl | cyclobutyl | 120 ± 40 | 6450 ± 720 | 2790 ± 720 | 18.1 ± 6.8 |
| 218 5729 (R) | cyclopropyl | cyclopropylmethyl | 490 ± 90 | 4840 ± 400 | 1760 ± 210 | 18.4 ± 2.1 |
| 219 5732 (S) | cyclopropylmethyl | cyclopropyl | 170 ± 20 | 2550 ± 170 | 550 ± 50 | 24.0 ± 5.2 |
| 220 5718 (R) | Ph | cyclopropyl | 3000 ± 440 | (46 ± 4%) | 790 ± 100 | −7.4 ± 6.0 |
| 221 5731 (S) | cyclopropyl | Ph | (50 ± 5%) | (36 ± 4%) | 2200 ± 470 | −2.4 ± 3.7 |
| 235a CPA | [j] | | 1.8 ± 0.5[f] | 794[h] | 72 ± 12[e] | 100 ± 2.6 |
| 235b CCPA | [j] | | 0.83[g] | 2270[h] | 38 ± 6[e] | ND |
| 236 NECA | [j] | | 6.8 ± 2.4[f] | 20[h] | 35 ± 12[e] | 100 ± 15 |

TABLE 3-continued

| | | | | | |
|---|---|---|---|---|---|
| 237 ADAC | [j] | 10.4 ± 3.8[i] | 370 ± 100[i] | 12.4 ± 4.1[i] | ND |

Figure 14:
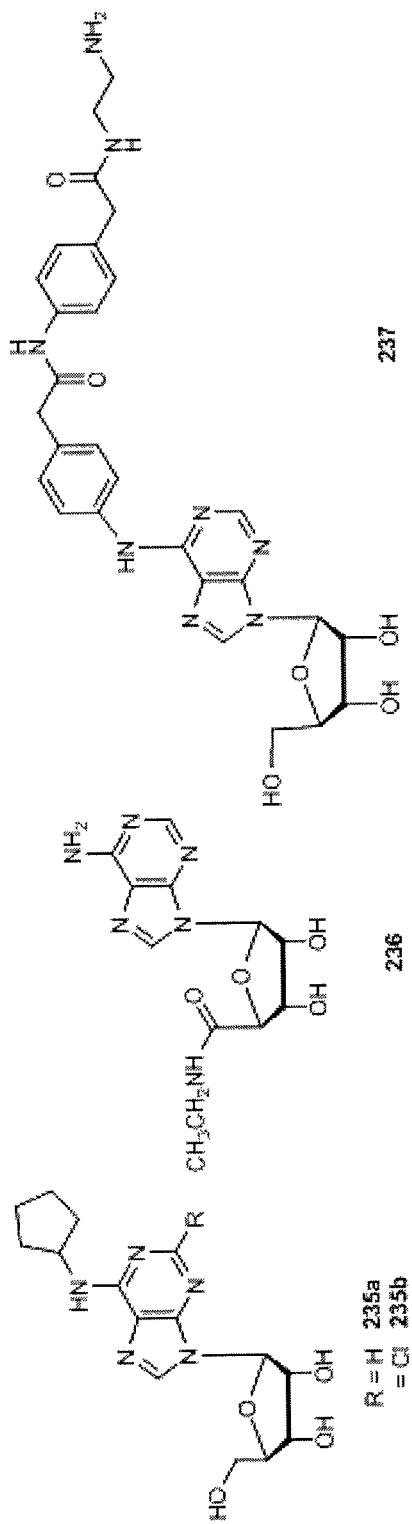
FIG. 14 depicts the structures of compounds 235a, 235b, 236, and 237.

[a]Using CHO or HEK293 ($A_{2A}$ only) cells stably expressing a hAR; affinity was expressed as $K_i$ value (n = 3-5) or percent inhibition of radioligand binding at 10 μM. The radioligands used were: ([$^3$H]N$^6$—R-phenylisopropyladenosine (R—PIA), [$^3$H]2-[p-(2-carboxyethyl)phenyl-ethylamino]-5'-N-ethylcarboxamidoadenosine (CGS21680), or [$^{125}$I]N$^6$-(4-amino-3-iodo-benzyl)adenosine-5'-N-methyl-uronamide (I—AB—MECA), respectively), unless noted.
[b]Values from refs. Tchilibon, S., et al,, supra; Jacobson, K. A., et al., supra; and Tosh, D. K., et al., supra. 203-206 and 208-209 and 121 were prepared as reported previously; see Tosh, D. K., et al., supra.
[c]206 is a diastereomeric mixture.
[d]Maximal efficacy (at 10 μM) in an ALAR functional assay, determined by inhibition of forskolin-stimulated cyclic AMP production in AR-transfected CHO cells, expressed as percent inhibition (mean ± standard error, n = 3 - 5) in comparison to effect (100%) of full agonist 235a at 10 μM. Compound 210 in Table 3 is the same as compound 121 in Table 2.
[e]Gao et al., Biochem.Pharmacol. 2003, 65, 1675-1684.
[f]Gao et al., Biochem. Pharmacol. 2004, 68, 1985-1993.
[g]Klotz et al., Naunyn-Schmiedeberg's Arch. Pharmacol. 1998, 357, 1-9.
[h]Müller and Jacobson, BBA Biomembranes 2011, 1808, 1290-1308.
[i]Klutz et al., J. Nanobiotechnol. 2008, 6, 12.
[j]The structures of compounds 235a, 235b, 236, and 237 are shown in FIG. 14.
ND = not determined.

Figure 15:
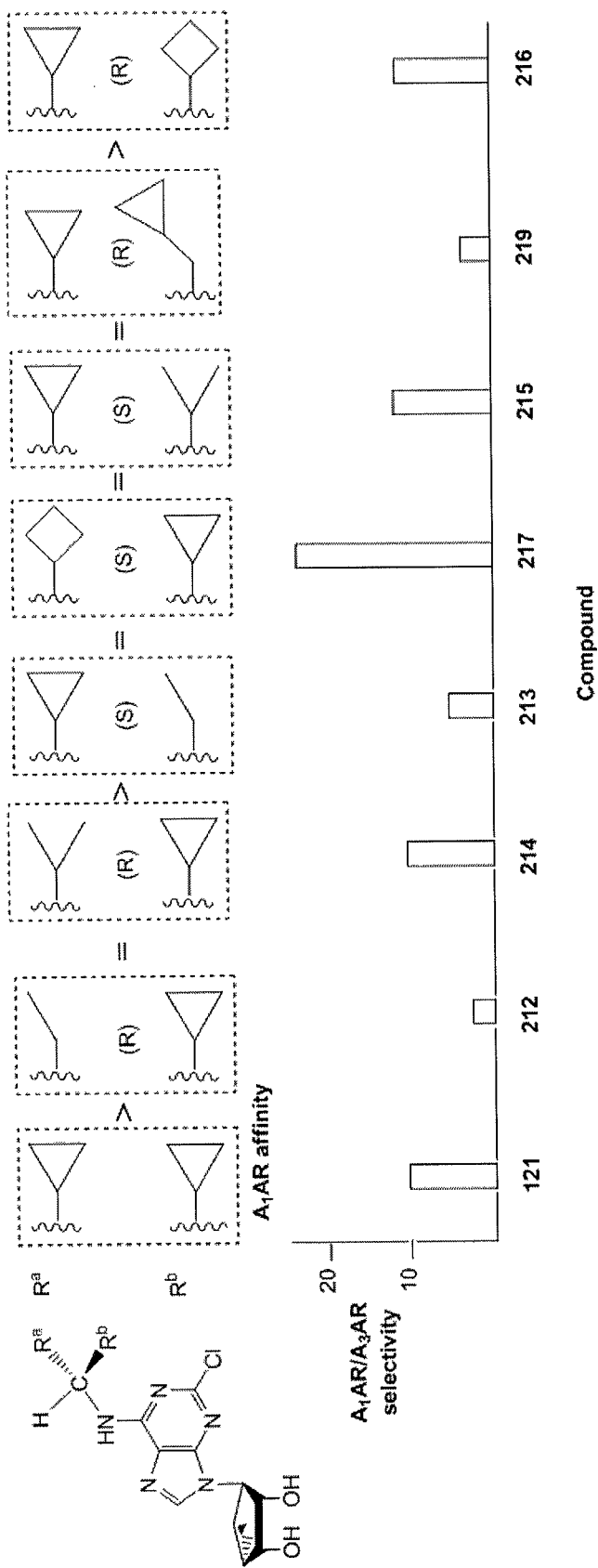
FIG. 15 depicts a graphical comparison of certain potent compounds of the invention by rank order of $hA_1AR$ binding affinity and illustrates the $hA_1AR/hA_3AR$ selectivity.

FIG. 15 depicts a graphical comparison of certain potent compounds of the invention by rank order of $hA_1AR$ binding affinity and illustrates the $hA_1AR/hA_3AR$ selectivity.

EXAMPLE 10

This Example illustrates the antiseizure and anticonvulsant properties of compounds illustrated in Example 9,
Animals and Test Substances Used for Seizure Testing Adult male CF No 1 albino mice (26-30 g, 6 Hz; 18-25 g all other tests), were obtained from Charles River, Portage, Mich. Animals were housed in an Association for Assessment and Accreditation of Laboratory Animal Care, International (AAALAC)-accredited temperature and humidity controlled facility and maintained on a standard 12 h: 12 h light-dark (lights on at 0600) cycle with free access to standard laboratory chow Prolab RMH 3000) and water ad libitum. All animal experiments were performed in accordance with the guidelines set by National Institute of Health and the University of Utah Institutional Animal Care and Use Committee (IACUC) committee. All animals were allowed free access to both food (and water except when they were removed from their cages for the experimental procedure. Except for the kindling studies, animals were used once. All animals were euthanized in accordance with the Institute of Laboratory Resources policies on the humane care of laboratory animals.
Anticonvulsant Tests In vivo anticonvulsant activity was established by both electrical and chemoconvulsant seizure tests which have been described previously. White, H. S., et al., Ital. J. Neurol. Sci. 1995, 16, 73-77; White, H. S. et al., Antiepileptic Drugs (Levy R H M, R. H.; Meldrum, B. S. ed), 1995, pp 99-110, Raven Press, New York.; and Smith, M., et al., Neurotherapeutics 2007, 4, 12-17.

The electrical tests used were the maximal electroshock (MES) seizure test, the 6 Hz minimal clonic seizure test, and the corneal kindled mouse test. The chemical test was the s.c. metrazol seizure tests. Time of peak effect (TPE) is deduced from data generated in initial qualitative test procedures. Five groups of 4 animals each are administered the test compound, and each group is tested at one of five different time intervals: ¼, ½, 1, 2 and 4 h. The time point at which the compound produces the most activity/toxicity was chosen as TPE.
MES Test and 6 Hz Test For the MES and 6 Hz tests, a drop of anesthetic/electrolyte solution (0.5% tetracaine hydrochloride in 0.9% saline) was applied to the eyes of each animal prior to placement of the corneal electrodes. The electrical stimulus in the MES test was 50 mA, 60 Hz, for mice. Abolition of the hindleg tonic extensor component of the seizure was used as the endpoint.

The ability of the test substance to prevent seizures induced by 6 Hz corneal stimulation (32 mA, 3 sec duration) in mice was evaluated at a convulsive current that evokes a seizure in 97% of the population tested ($CC_{97}$). Six Hz seizures are characterized by a minimal clonic phase that is followed by stereotyped, automatistic behaviors described originally as being similar to the aura of human patients with partial seizures. Toman, J. E. et al., Tex. Rep. Biol. Med. 1952, 10, 96-104; Barton, M. E. et al., Epilepsy Res. 2001, 47, 217-227.

Animals not displaying this behavior were considered protected.
Corneal-Kindled Mouse Model of Partial Seizures Mice were kindled according to the methods described by Matagne and Klitgaard; Epilepsy Res. 1998, 31, 59-71. Briefly, mice were stimulated twice daily with a corneal stimulation of 3 mA for 3 seconds for an average of 12 days. Prior to each stimulation, a drop of 0.9% saline containing 0.5% tetracaine hydrochloride (Sigma-Aldrich, St. Louis, Mo.) was applied to the cornea to ensure local anesthesia and good electrical conductivity. Stimulations were at least four hours apart. Animals were considered kindled when they displayed five consecutive stage five seizures according to the Racine scale. See Racine, R., Electroencephalogr. Clin. Neurophysiol. 1972, pp. 281-294.

At the completion of the kindling acquisition, mice were permitted at least a 3-day stimulation-free period prior to any drug testing. Mice were stimulated once the day before drug testing to ensure they had achieved and maintained a kindled state. On the day of the drug study, corneal kindled mice (n=4, or 8) received a single i.p. dose of test compound. Mice were challenged with the corneal kindling stimulus of 3 mA for 3 seconds at TPE after test compound administration. Mice were scored as protected (seizure score of ≤3) or not protected, (seizure score ≥4) based on the Racine scoring.
Minimal Behavioral Toxicity Tests Minimal behavioral toxicity was identified in mice by the rotorod procedure. Dunham, M. S., et al., J. Amer. Pharm. Ass. Sci. Ed. 1957, 46, 208-209. When a mouse is placed on a 1-inch knurled rod that rotates at a speed of 6 r.p.m., the animal can maintain its equilibrium for long periods of time. The animal was considered toxic if it fell off this rotating rod three times during a 1-min period.
Determination of Median Effective ($ED_{50}$) or Behavioral Toxic Dose ($TD_{50}$)

All quantitative in vivo anticonvulsant/toxicity studies were conducted at the previously determined TPE. Groups of at least eight mice were tested with various doses of the candidate drug until at least two points were established between the limits of 100% protection or minimal toxicity and 0% protection or minimal toxicity. The dose of drug required to produce the desired endpoint in 50% of animals ($ED_{50}$ or $TD_{50}$) in each test, the 95% confidence interval, the slope of the regression line, and the S.E.M. of the slope were then calculated by a computer program based on the method described by Finney in *Methods Inf. Med.* 1971, 10, 237-245. Compound Administration.

The test compound was administered at a concentration that permitted optimal accuracy of dosing without the volume contributing excessively to total body fluid. Thus, test compounds are administered to mice in a volume of 0.01 ml/g of body weight. Compound 121 or other AR agonist was initially dissolved in DMSO (10 mg/ml) as a stock solution. To prepare the formulation for testing, an appropriate amount of stock solution was first diluted in DMSO to achieve 10% DMSO (v/v) in the final volume. Then, to the aqueous DMSO solution, 30% PEG400 (J. T. Baker) was gradually was added to make the final formulation.

TABLE 4

Anticonvulsant activity of $A_1AR$ agonists.

| Compound[a] | Behavioral toxicity $TD_{50}$ (mg/kg) | 6 Hz model $ED_{50}$ (mg/kg) | MES model[b] (dose) | scMET model[b] (dose) |
|---|---|---|---|---|
| 121 | >10 | 2.74[c] | 1 out of 4 (3 mg/kg) | No protection (3 mg/kg) |
| 235b | 0.84[c] | 0.12[c] | 1 out of 4 at (1 mg/kg) | 1 out of 4 (1 mg/kg) |
| 237 | 0.14[d] | 0.03[c] | 4 out of 8 (2 mg/kg) | 5 out of 8 (1 mg/kg) |

[a]administered i.p.
[b]qualitative results, expressed as number of animals protected from convulsions.
[c]measured at 1 h (time of peak of effect) post injection.
[d]measured at 4 h (time of peak of effect) post injection.

In the minimal behavioral toxicity test using the rotarod, no toxicity was observed for compound 121 for up to 10 mg/kg in contrast to compound 235b, which showed 0.84 mg/kg 1 hour post injection as it showed in the 6 Hz model (0.12 mg/kg) and at the same time point. Thus, compound 121 is superior to compound 235b. Compound 121 was also tested in the corneal kindled mouse model to examine its effect on focal seizures. In a qualitative test, all animals (n=4) were protected at a dose of 3 mg/kg at 1 hour post injection. The unique profile of compound 121 makes it an attractive candidate to treat drug-resistant epilepsy. On the basis for the lack of peripheral side effects of compound 121, it is contemplated as follows. Both 235b and 121 evidently enter the blood stream and pass the BBB into the brain. Although in in vitro binding, 121 is ~40 times less potent at the $A_1AR$ compared to 235b, it has better physicochemical properties (c Log P, tPSA, HBD, etc.), so it likely penetrates the BBB better than 235b. Its $ED_{50}$ in antiseizure models is only about 20 times less potent. There is two-fold enhancement in entry through the BBB. The bioavailability of peripherally administered 121 in the brain, i.e. whether it altered physicochemical properties may facilitate its passage across the BBB, is undetermined. Normally a drug travels from the blood stream into brain, such that when the $A_1AR$ in brain is activated, the $A_1AR$ in heart should be activated within the same dose range as with 235. For 121, the fact that no adverse effects were observed even at 10 mg/kg (three times the $ED_{50}$) suggests that the free concentration of 121 in plasma would be lower than that in brain. One plausible explanation of this difference is due to plasma protein binding, which is correlated with increased log D. Compound 121 potentially has higher plasma protein binding due to its increased log D, and therefore its free concentration in plasma could be lower than that in brain. Although the free drug concentration in blood is lower, its ability to cross BBB through diffusion or active transporter is not affected or even increased. This phenomenon has been observed in a number of CNS drugs.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:
1. A compound of formula (I)

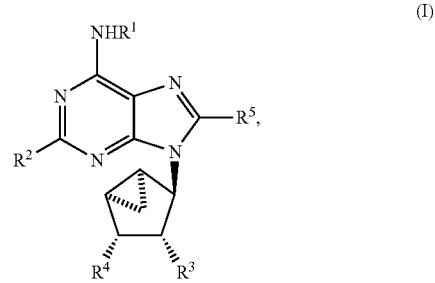

wherein
$R^1$ is selected from the group consisting of hydrogen, $C_1$-$C_6$ alkyl, $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, —CH($R^a$)($R^b$), $C_6$-$C_{14}$ aryl, $C_6$-$C_{14}$ aryl $C_1$-$C_6$ alkyl, $C_6$-$C_{14}$ diaryl $C_1$-$C_6$ alkyl, and $C_6$-$C_{14}$ aryl $C_1$-$C_6$ alkoxy, wherein $R^a$ and $R^b$ are independently selected from the group consisting of $C_1$-$C_6$ alkyl, $C_3$-$C_8$ cycloalkyl, and $C_6$-$C_{14}$ aryl, wherein the aryl portion of $R^1$ is optionally substituted with one or more substituents selected from the group consisting of halo, amino, hydroxyl, carboxy, $C_1$-$C_6$ alkoxycarbonyl, aminocarbonyl, $C_1$-$C_6$ alkylaminocarbonyl, $C_1$-$C_6$ dialkyl aminocarbonyl, $C_1$-$C_6$ alkyl, $C_2$-$C_6$ alkenyl, $C_2$-$C_6$ alkynyl, $C_1$-$C_6$ alkoxy, halo $C_1$-$C_6$ alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, carboxy $C_1$-$C_6$ alkyl, carboxy $C_2$-$C_6$ alkenyl, carboxy $C_2$-$C_6$ alkynyl, aminocarbonyl $C_1$-$C_6$ alkyl, aminocarbonyl $C_2$-$C_6$ alkenyl, aminocarbonyl $C_2$-$C_6$ alkynyl, and $C\equiv C$—$(CH_2)_n$—$COR^7$, wherein $R^7$ is selected from the group consisting of OH, $OR^8$, and $NR^9R^{10}$, wherein $R^8$ is selected from the group consisting of $C_1$-$C_6$ alkyl, $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, and $C_6$-$C_{14}$ diaryl $C_1$-$C_6$ alkyl;

and wherein $R^9$ and $R^{10}$ are independently selected from the group consisting of hydrogen, $C_1$-$C_6$ alkyl, and $(CH_2)_n R^{11}$ wherein $R^{11}$ is $NR^{12}R^{13}$, wherein $R^{12}$ and $R^{13}$ are independently selected from the group consisting of hydrogen, $C_1$-$C_6$ alkyl, and $COR^{14}$, wherein $R^{14}$ is hydrogen or $C_1$-$C_6$ alkyl; wherein n is an integer from 1 to 10; and the alkyl or cycloalkyl portion of $R^1$ is optionally substituted with one or more substituents selected from the group consisting of halo, amino, $C_1$-$C_6$ alkyl, $C_1$-$C_6$ alkoxy, $C_6$-$C_{14}$ aryloxy, $C_1$-$C_6$ hydroxyalkyl, $C_2$-$C_6$ hydroxyalkenyl, $C_2$-$C_6$ hydroxy alkynyl, aminocarbonyl $C_1$-$C_6$ alkoxy, and $C_6$-$C_{14}$ aryl $C_1$-$C_6$ alkoxy;

$R^2$ is selected from the group consisting of hydrogen, halo, amino, hydrazido, mercapto, $C_1$-$C_{20}$ alkylamino, $C_6$-$C_{14}$ aryl amino, $C_6$-$C_{14}$ aryloxy, $C_1$-$C_{20}$ alkyl, $C_1$-$C_{20}$ alkoxy, $C_1$-$C_{20}$ thioalkoxy, pyridylthio, heterocyclyl, $C_7$-$C_{12}$ cycloalkyl $C_1$-$C_{20}$ alkyl, $C_7$-$C_{12}$ bicycloalkyl $C_1$-$C_{20}$ alkyl, $C_7$-$C_{12}$ bicycloalkenyl $C_1$-$C_{20}$ alkyl, $C_6$-$C_{14}$ aryl $C_1$-$C_{20}$ alkyl, $C_2$-$C_{20}$ alkenyl, $C_7$-$C_{12}$ cycloalkyl $C_2$-$C_{20}$ alkenyl, $C_7$-$C_{12}$ bicycloalkyl $C_2$-$C_{20}$ alkenyl, $C_7$-$C_{12}$ bicycloalkenyl $C_2$-$C_{20}$ alkenyl, $C_6$-$C_{14}$ aryl $C_2$-$C_{20}$ alkenyl, $C_2$-$C_{20}$ alkynyl, carboxy $C_2$-$C_{20}$ alkynyl, —$C\equiv C$—$(CH_2)_m$—$C(=O)$—$O$—$C_1$-$C_6$ alkyl, —$C\equiv C$—$(CH_2)_m$—$C(=O)$—$NH$—$(CH_2)_n$—$NH_2$, —$C\equiv C$—$(CH_2)_m$—$C_1$-$C_6$ alkyl, —$C\equiv C$—$(CH_2)_m$-aryl, wherein m and n are independently 1 to 10, $C_7$-$C_{12}$ cycloalkyl $C_2$-$C_{20}$ alkynyl, $C_7$-$C_{12}$ bicycloalkyl $C_2$-$C_{20}$ alkynyl, $C_7$-$C_{12}$ bicycloalkenyl $C_2$-$C_{20}$ alkynyl, $C_6$-$C_{14}$ aryl $C_2$-$C_{20}$ alkynyl, and the alkyl, cycloalkyl, heterocyclyl, or aryl portion of $R^2$ is optionally substituted with one or more substituents selected from the group consisting of halo, hydroxyl, amino, alkylamino, dialkylamino, sulfur, carboxy, alkoxycarbonyl, aminocarbonyl, alkylaminocarbonyl, dialkyl aminocarbonyl, aminoalkyl aminocarbonyl, pyridyl, alkyl pyridyl, haloalkyl pyridyl, trihaloalkyl pyridyl, carboxy pyridyl, pyrazinyl, quinolinyl, quinazolinyl, and trialkylsilyl, or wherein the heterocyclyl is optionally substituted with an optionally substituted alkyl, optionally substituted aryl, optionally substituted heteroaryl, carboxyl, sulfonyl, —$C(O)OR^e$, —$CH(OH)R^e$, or $C(O)NR^eR^f$, wherein $R^e$ or $R^f$ is hydrogen, optionally substituted alkyl, optionally substituted cycloalkyl, optionally substituted aralkyl, optionally substituted aryl, or optionally substituted heteroaryl;

$R^3$ and $R^4$ are independently selected from the group consisting of hydroxyl, amino, thiol, ureido, $C_1$-$C_6$ alkyl carbonylamino, hydroxy $C_1$-$C_6$ alkyl, and hydrazinyl; and $R^5$ is selected from the group consisting of hydrogen, $C_1$-$C_6$ alkyl, $C_2$-$C_6$ alkenyl, $C_2$-$C_6$ alkynyl, heteroaryl, and $C_1$-$C_6$ aminoalkyl;

or a pharmaceutically acceptable salt thereof.

2. The compound or salt of claim 1, wherein $R^1$ is selected from the group consisting of hydrogen, $C_1$-$C_6$ alkyl, $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{14}$ tricycloalkyl $C_1$-$C_6$ alkyl, —$CH(R^a)(R^b)$, and $C_6$-$C_{14}$ aryl $C_1$-$C_6$ alkyl, wherein $R^a$ and $R^b$ are independently selected from the group consisting of $C_1$-$C_6$ alkyl, $C_3$-$C_8$ cycloalkyl, and $C_6$-$C_{14}$ aryl, wherein the aryl portion of $R^1$ is optionally substituted with one or more substituents selected from the group consisting of halo, $C_1$-$C_6$ alkoxy, and halo $C_1$-$C_6$ alkoxy.

3. The compound or salt of claim 1, wherein $R^2$ is halo.

4. The compound or salt of claim 1, wherein $R^3$ and $R^4$ are hydroxyl.

5. The compound or salt of claim 1, wherein $R^5$ is hydrogen.

6. The compound or salt of claim 1, wherein $R^2$ is chloro.

7. The compound or salt of claim 1, wherein $R^1$ is:

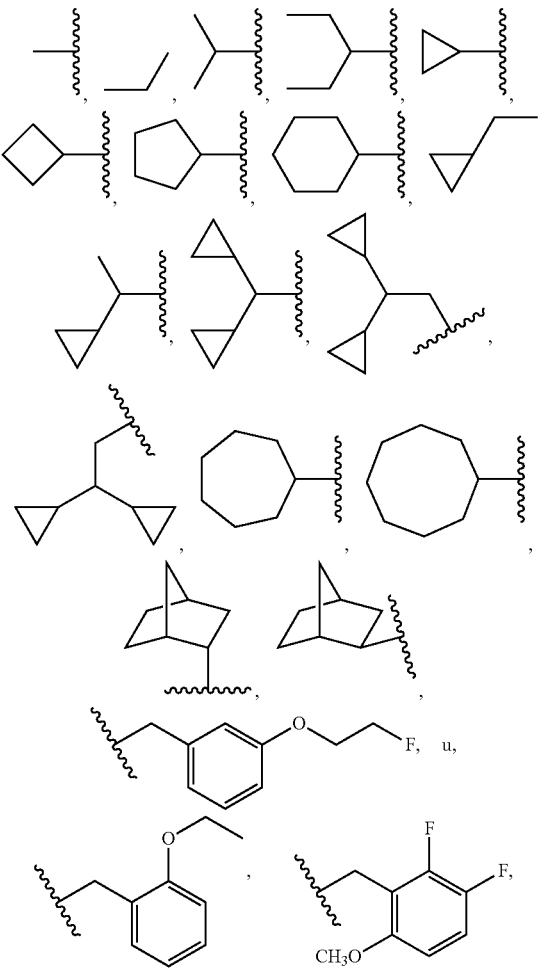

-continued

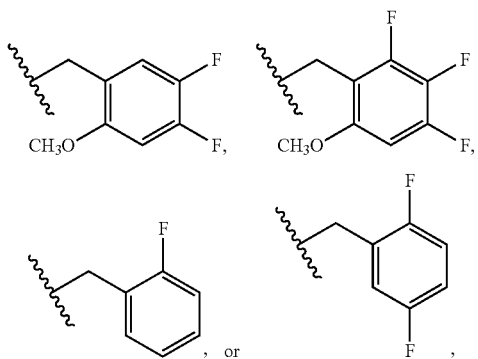

$R^2$ is chloro, $R^3$ and $R^4$ are hydroxyl, and $R^5$ is hydrogen.

8. The compound or salt of claim 1, wherein the compound is of the formula (Ia):

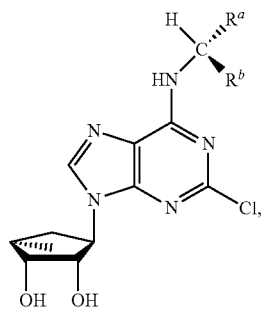

(Ia)

wherein:

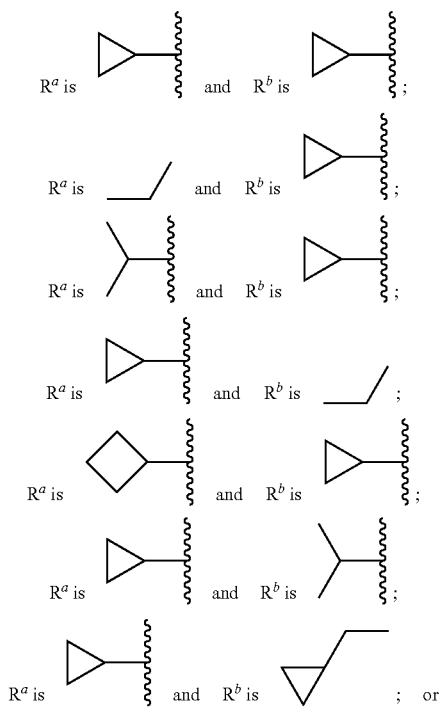

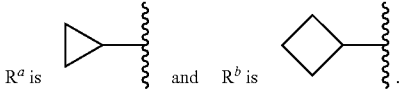

9. A pharmaceutical composition comprising a compound or salt of claim 1 and a pharmaceutically acceptable carrier.

10. A method of treating a disease in a mammal comprising administering to the mammal an effective amount of a compound of formula (I):

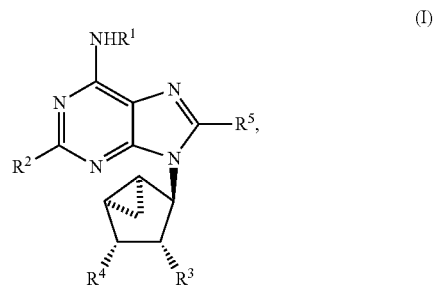

(I)

wherein $R^1$ is selected from the group consisting of hydrogen, $C_1$-$C_6$ alkyl, $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, —CH($R^a$)($R^b$), $C_6$-$C_{14}$ aryl, $C_6$-$C_{14}$ aryl $C_1$-$C_6$ alkyl, $C_6$-$C_{14}$ diaryl $C_1$-$C_6$ alkyl, and $C_6$-$C_{14}$ aryl $C_1$-$C_6$ alkoxy, wherein $R^a$ and $R^b$ are independently selected from the group consisting of $C_1$-$C_6$ alkyl, $C_3$-$C_8$ cycloalkyl, and $C_6$-$C_{14}$ aryl, wherein the aryl portion of $R^1$ is optionally substituted with one or more substituents selected from the group consisting of halo, amino, hydroxyl, carboxy, $C_1$-$C_6$ alkoxycarbonyl, aminocarbonyl, $C_1$-$C_6$ alkylaminocarbonyl, $C_1$-$C_6$ dialkyl aminocarbonyl, $C_1$-$C_6$ alkyl, $C_2$-$C_6$ alkenyl, $C_2$-$C_6$ alkynyl, $C_1$-$C_6$ alkoxy, halo $C_1$-$C_6$ alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkenyl, carboxy $C_1$-$C_6$ alkyl, carboxy $C_2$-$C_6$ alkenyl, carboxy $C_2$-$C_6$ alkynyl, aminocarbonyl $C_1$-$C_6$ alkyl, aminocarbonyl $C_2$-$C_6$ alkenyl, aminocarbonyl $C_2$-$C_6$ alkynyl, and C≡C—(CH$_2$)$_n$—COR$^7$, wherein $R^7$ is selected from the group consisting of OH, OR$^8$, and NR$^9$R$^{10}$, wherein $R^8$ is selected from the group consisting of $C_1$-$C_6$ alkyl, $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, and $C_6$-$C_{14}$ diaryl $C_1$-$C_6$ alkyl;

and wherein $R^9$ and $R^{10}$ are independently selected from the group consisting of hydrogen, $C_1$-$C_6$ alkyl, and (CH$_2$)$_n$R$^{11}$ wherein R$^{11}$ is NR$^{12}$R$^{13}$, wherein $R^{12}$ and $R^{13}$ are independently selected from the group consisting of hydrogen, $C_1$-$C_6$ alkyl, and COR$^{14}$, wherein $R^{14}$ is hydrogen or $C_1$-$C_6$ alkyl; wherein n is an integer from 1 to 10; and the alkyl or cycloalkyl portion of $R^1$ is optionally substituted with one or more substituents selected from the group consisting of halo, amino, $C_1$-$C_6$ alkyl, $C_1$-$C_6$ alkoxy, $C_6$-$C_{14}$ aryloxy, $C_1$-$C_6$ hydroxyalkyl, $C_2$-$C_6$ hydroxyalkenyl, $C_2$-$C_6$ hydroxyalkynyl, aminocarbonyl $C_1$-$C_6$ alkoxy, and $C_6$-$C_{14}$ aryl $C_1$-$C_6$ alkoxy;

$R^2$ is selected from the group consisting of hydrogen, halo, amino, hydrazido, mercapto, $C_1$-$C_{20}$ alkylamino, $C_6$-$C_{14}$ aryl amino, $C_6$-$C_{14}$ aryloxy, $C_1$-$C_{20}$ alkyl, $C_1$-$C_{20}$ alkoxy, $C_1$-$C_{20}$ thioalkoxy, pyridylthio, heterocyclyl, $C_7$-$C_{12}$ cycloalkyl $C_1$-$C_{20}$ alkyl, $C_7$-$C_{12}$ bicycloalkyl $C_1$-$C_{20}$ alkyl, $C_7$-$C_{12}$ bicycloalkenyl $C_1$-$C_{20}$ alkyl, $C_6$-$C_{14}$ aryl $C_1$-$C_{20}$ alkyl, $C_2$-$C_{20}$ alkenyl, $C_7$-$C_{12}$ cycloalkyl $C_2$-$C_{20}$ alkenyl, $C_7$-$C_{12}$ bicycloalkyl $C_2$-$C_{20}$ alkenyl, $C_7$-$C_{12}$ bicycloalkenyl $C_2$-$C_{20}$ alkenyl, $C_6$-$C_{14}$ aryl $C_2$-$C_{20}$ alkenyl, $C_2$-$C_{20}$ alkynyl, carboxy alkyl $C_2$-$C_{20}$ alkynyl, —C≡C—$(CH_2)_m$—C(=O)—O—$C_1$-$C_6$ alkyl, —C≡C—$(CH_2)_m$—C(=O)—NH—$(CH_2)_n$—$NH_2$, —C≡C—$(CH_2)_m$—$C_1$-$C_6$ alkyl, —C≡C—$(CH_2)_m$-aryl, wherein m and n are independently 1 to 10, $C_7$-$C_{12}$ cycloalkyl $C_2$-$C_{20}$ alkynyl, $C_7$-$C_{12}$ bicycloalkyl $C_2$-$C_{20}$ alkynyl, $C_7$-$C_{12}$ bicycloalkenyl $C_2$-$C_{20}$ alkynyl, $C_6$-$C_{14}$ aryl $C_2$-$C_{20}$ alkynyl, and the alkyl, cycloalkyl, heterocyclyl, or aryl portion of $R^2$ is optionally substituted with one or more substituents selected from the group consisting of halo, hydroxyl, amino, alkylamino, dialkylamino, sulfur, carboxy, alkoxycarbonyl, aminocarbonyl, alkylaminocarbonyl, dialkyl aminocarbonyl, aminoalkyl aminocarbonyl, pyridyl, alkyl pyridyl, haloalkyl pyridyl, trihaloalkyl pyridyl, carboxy pyridyl, pyrazinyl, quinolinyl, quinazolinyl, and trialkylsilyl, or wherein the heterocyclyl is optionally substituted with an optionally substituted alkyl, optionally substituted aryl, optionally substituted heteroaryl, carboxyl, sulfonyl, —C(O)$OR^e$, —CH(OH)$R^e$, or C(O)$NR^eR^f$, wherein $R^e$ or $R^f$ is hydrogen, optionally substituted alkyl, optionally substituted cycloalkyl, optionally substituted aralkyl, optionally substituted aryl, or optionally substituted heteroaryl;

$R^3$ and $R^4$ are independently selected from the group consisting of hydroxyl, amino, thiol, ureido, $C_1$-$C_6$ alkyl carbonylamino, hydroxy $C_1$-$C_6$ alkyl, and hydrazinyl; and $R^5$ is selected from the group consisting of hydrogen, $C_1$-$C_6$ alkyl, $C_2$-$C_6$ alkenyl, $C_2$-$C_6$ alkynyl, heteroaryl, and $C_1$-$C_6$ aminoalkyl;

or a pharmaceutically acceptable salt thereof, wherein the disease is selected from the group consisting of seizures, convulsion, stroke, diabetes, pain, arrhythmias, and anxiety.

11. A method of cardioprotecting or neuroprotecting a mammal in need thereof comprising administering to the mammal an effective amount of a compound of claim 1 or a pharmaceutically acceptable salt thereof, wherein in the cardioprotection is in ischemia and the neuroprotection is in ischemia, seizure, or epilepsy.

12. A method for partially or fully activating an $A_1$ adenosine receptor in a mammal in need thereof comprising administering to the mammal an effective amount of a compound of claim 1 or a pharmaceutically acceptable salt thereof.

* * * * *